US008124419B2

(12) United States Patent
Brahim et al.

(10) Patent No.: US 8,124,419 B2
(45) Date of Patent: Feb. 28, 2012

(54) GAS SENSOR DEVICES COMPRISING ORGANIZED CARBON AND NON-CARBON ASSEMBLY

(75) Inventors: Sean Imtiaz Brahim, Camarillo, CA (US); Leonid Grigorian, Camarillo, CA (US); Steven G. Colbern, Fillmore, CA (US); Robert L. Gump, Camarillo, CA (US); Fikret Nuri Kirkbir, Studio City, CA (US)

(73) Assignee: Yazaki Corporation, Tokyo (JP)

( * ) Notice: Subject to any disclaimer, the term of this patent is extended or adjusted under 35 U.S.C. 154(b) by 0 days.

(21) Appl. No.: 12/762,976

(22) Filed: Apr. 19, 2010

(65) Prior Publication Data

US 2010/0200430 A1  Aug. 12, 2010

Related U.S. Application Data

(63) Continuation of application No. 12/114,625, filed on May 2, 2008, now abandoned.

(60) Provisional application No. 60/916,104, filed on May 4, 2007, provisional application No. 60/981,412, filed on Oct. 19, 2007, provisional application No. 60/986,167, filed on Nov. 7, 2007, provisional application No. 61/032,333, filed on Feb. 28, 2008, provisional application No. 61/033,630, filed on Mar. 4, 2008, provisional application No. 61/035,306, filed on Mar. 10, 2008.

(51) Int. Cl.
*G01N 33/00* (2006.01)

(52) U.S. Cl. ......................... 436/132; 977/953

(58) Field of Classification Search .................. 436/132; 977/734, 742, 744, 745, 748, 840, 841, 846, 977/953
See application file for complete search history.

(56) References Cited

U.S. PATENT DOCUMENTS

| 3,992,267 | A | * | 11/1976 | Oswin et al. | ................... | 205/781 |
| 4,242,303 | A | * | 12/1980 | Takahashi et al. | .............. | 422/98 |
| 7,438,885 | B1 | * | 10/2008 | Seal et al. | .................. | 423/447.1 |
| 2003/0058114 | A1 | | 3/2003 | Miller et al. | | |
| 2006/0000259 | A1 | | 1/2006 | Rothschild et al. | | |
| 2006/0034731 | A1 | | 2/2006 | Lewis et al. | | |

FOREIGN PATENT DOCUMENTS

| DE | 10118200 | | 10/2002 |
| JP | 2003227806 | A2 | 8/2003 |
| JP | 2006112819 | A2 | 4/2006 |
| WO | WO 2007/096635 | | 8/2007 |

OTHER PUBLICATIONS

U. Ackelid et al., Ethanol Sensitivity of Palladium-Gate Metal-Oxide-Semiconductor Structures, EDL-7 IEEE Electron Device Lett. 353-355 (1986).*
Palladium Doped Semiconductor Alcohol Sensor, 34 Platinum Metals Rev. 130 (1990).*
J. Kong et al., Nanotube Molecular Wires as Chemical Sensors, 287 Science 622-625 (2000).*
Ionescu, R. et al., "Novel hybrid materials for gas sensing applications made of metal-decorated MWCNTs dispersed on nano-particle metal oxides," Sensors and Actuators B, vol. 131, pp. 174-182 (2008).
Penza, M. et al., "Effect of Growth Catalysts on Gas Sensitivity in Carbon Nanotube Film Based Chemiresistive Sensors," Applied Physics Letters, 90, 103101 (2007).
Penza, M. et al., "Enhancement of Sensitivity in Gas Chemirestistors Based on Carbon Nanotube Surface Functionalized With Noble Metal (Au, Pt) Nanoclusters," Applied Physics Letters, 90, 173123 (2007).
Kong, Jing et al., "Functionalized Carbon Nanotubes for Molecular Hydrogen Sensors," Advanced Materials, vol. 13, No. 18, pp. 1384-1386 (Sep. 14, 2001).
Peng, Shu et al., "Ab Initio Study of Doped Carbon Nanotube Sensors," Nano Letters, vol. 3, No. 4, pp. 513-517 (2003).
Qi, Pengfei et al., "Toward Large Arrays of Multiplex Functionalized Cabon Nanotube Sensors for Highly Sensitive Selective Molecular Detection," Nano Letters, vol. 3, No. 3, pp. 347-351 (2003).
Wong, Y.M. et al., "A Novel Microelectronic Gas Sensor Utilizing Carbon Nanotubes for Hydrogen Gas Detection," Sensors and Actuators B, vol. 93, pp. 327-332 (2003).
Lu, Yijiang et al., "Room Temperature Methane Detection Using Palladium Loaded Single-Walled Carbon Nanotube Sensors," Chemical Physical Letters, vol. 391, pp. 344-348 (2004).
Sayago, I. et al., "Hydrogen Sensors Based on Carbon Nanotubes Thin Films," Synthetic Metals, vol. 148, pp. 15-19 (2005).
Snow, E.S. et al., "Chemical Detection With a Single-Walled Carbon Nanotube Capacitor," Science, vol. 307, pp. 1942-1945 (2005).
Chen, Yujin et al., "The Enhanced Ethanol Sensing Properties of Multi-Walled Carbon Nanotubes/$SnO_2$ Core/Shell Nanostructures," Nanotechnology, vol. 17, pp. 3012-3017 (2006).
Kumar, M. Krishna et al., Nanostructured Pt Functionalized Multiwalled Carbon Nanotube Based Hydrogen Sensor, J. Phys. Chem. B., vol. 110, pp. 11291-11298 (2006).
Lu, Yijiang et al., "A Carbon Nanotube Sensor Array for Sensitive Gas Discrimination Using Principal Component Analysis," Journal of Electroanalytical Chemistry, vol. 593, pp. 105-110 (2006).
Suehiro, Junya et al., "Schottky-Type Response of Carbon Nanotube $NO_2$ Gas Sensor Fabricated Onto Aluminum Electrodes by Dielectrophoresis," Sensors and Actuators B, vol. 114, pp. 943-949 (2006).

(Continued)

*Primary Examiner* — Randy Boyer
(74) *Attorney, Agent, or Firm* — Perkins Coie LLP; Viola T. Kung

(57) ABSTRACT

This invention relates generally to gas sensors comprising organized assemblies of carbon and non-carbon compounds. The invention also relates to devices containing such gas sensors and analysis units. In preferred embodiments, the organized assemblies of the instant invention take the form of nanorods or their aggregate forms. More preferably, a nanorod is made up of a carbon nanotube filled, coated, or both filled and coated by a non-carbon material.

24 Claims, 48 Drawing Sheets

OTHER PUBLICATIONS

Liu, Yan-Li et al., "Gas Sensing Properties of Tin Dioxide Coated Onto Multi-Walled Carbon Nanotubes," Thin Solid Films, vol. 497, pp. 355-360 (2006).

Cava, Carlos et al., "Iron- and Iron Oxide-Filled Multi-Walled Carbon Nanotubes: Electrical and Memory Devices," Chemical Physics Letters, vol. 444, p. 304-308 (2007).

Espinosa, E.H. et al., "Metal-Decorated Multi-Walled Carbon Nanotubes for Low Temperature Gas Sensing," Thin Solid Films, vol. 515, pp. 8322-8327 (2007).

Espinosa, E.H. et al., "Highly Selective NO2 Gas Sensors Made of MWCNTs and WO3 Hybrid Layers," Journal of the Electrochemical Society, vol. 154(5), pp. J141-J149 (2007).

Varghese, O.K. et al., "Gas Sensing Characteristics of Multi-Wall Carbon Nanotubes," Sensors and Actuators B, vol. 81, No. 1, pp. 32-41 (2001).

Guerret-Piecourt, C. et al., "Relation Between Metal Electronic Structure and Morphology of Metal Compounds Inside Carbon Nanotubes," Nature, vol. 372, pp. 761-765 (2002).

Sloan, Jeremy et al., "Integral Atomic Layer Architectures of 1D Crystals Inserted Into Single Walled Carbon Nanotubes," Chemical Communications, No. 13, pp. 1319-1332 (2002).

Nguyen et al., "Behavior of Single-Walled Carbon Nanotube-Based Gas Sensors At Various Temperatures of Treatment and Operation," Sensors and Actuators B, vol. 117, No. 2. pp. 426-430 (2006).

Sloan, J. et al., "The Opening and Filling of Single Walled Carbon Nanotubes (SWTs)," Chemical Communications pp. 347-348 (Jan. 1, 1998).

Int'l Search Report, PCT/US2008/062562, mailed Jul. 31, 2008.

Bao, J. et al., "Synthesis and Magnetic Behavior of an Array of Nickel-Filled Carbon Nanotubes", 81 Appl. Phys. Lett. pp. 4592-4594 (2002).

Lu, Y. et al., "Room Temperature Methane Detection Using Palladium Loaded Single-Walled Carbon Nanotube Sensors", 391 Chem. Phys. Lett. pp. 344-348 (2004).

\* cited by examiner

GAS SENSOR DEVICES COMPRISING ORGANIZED CARBON AND NON-CARBON ASSEMBLY

This application is a continuation of U.S. patent application Ser. No. 12/114,625, filed May 2, 2008 now abandoned; which claims the benefit of U.S. Provisional Patent Application Nos. 60/916,104, filed May 4, 2007; 60/981,412, filed Oct. 19, 2007; 60/986,167, filed Nov. 7, 2007; 61/032,333, filed Feb. 28, 2008; 61/033,630, filed Mar. 4, 2008; and 61/035,306 filed Mar. 10, 2008. The contents of the above-identified applications are incorporated herein by reference in their entirety.

TECHNICAL FIELD

This invention relates generally to devices for detecting analyte gases. The devices comprise gas sensors comprising organized assemblies of carbon and non-carbon compounds. In preferred embodiments, the organized structures of the instant invention are made up of nanorods or their aggregate forms.

BACKGROUND OF THE INVENTION

There are many applications of carbon nanotubes (CNTs) because of their unique mechanical, physical, electrical, chemical and biological properties. For example, ultra low resistance conductors, semiconductors, highly efficient electron emitters, ultra-strong lightweight fibers for structural applications, and lasers can all be manufactured by using CNTs. For reviews of CNT technology, properties and applications, see Baughman et al., "Carbon Nanotubes—the Route Toward Applications", Science, volume 297, pages 787-792 (2002); Michael J. O'Connell (Editor) "Carbon Nanotubes—Properties and Applications", CRC Taylor & Francis, New York (2006); and Yury Gogotsi (Editor) "Nanomaterials Handbook", CRC Taylor & Francis, New York (2006).

A great deal of research effort has been directed toward the development of small dimensional inexpensive gas sensing devices for applications including monitoring and controlling environmental pollution; providing small, low-power, rapid and sensitive tools for process and quality control in industrial applications; and implementing or improving detection and quantification of harmful gases.

In many industries, gases have become increasingly important as raw materials and it has thereby become very important to develop highly sensitive gas detectors. Such devices should allow continuous monitoring of the concentration of particular gases in the environment in a quantitative and selective way. However, many of these efforts have not yet reached commercial viability because of problems associated with the sensor technologies applied to gas-sensing microsystems. Inaccuracies and inherent characteristics of the sensors themselves have made it difficult to produce fast, reliable and low-maintenance sensing systems comparable to other micro-sensor technologies that have grown into widespread use commercially.

The practical application of environmental monitoring requires developing sensing devices that are smaller and cheaper than the analytical instruments currently used. Much of the research on gas sensors to date has been carried out using either thick-film or thin-film metal oxide semiconductor sensors. Development of such sensors may have resulted in devices with reasonable sensitivities. For environmental purposes, however, greater sensitivities are required.

Among the gaseous species to be observed in air as contaminants (polluting gases) are nitrous oxide (NO), nitrogen dioxide ($NO_2$), carbon monoxide (CO), carbon dioxide ($CO_2$), hydrogen ($H_2$), hydrogen sulfide ($H_2S$), sulfur dioxide ($SO_2$), ozone ($O_3$), ammonia ($NH_3$), and organic gases such as methane ($CH_4$), propane ($C_3H_8$), liquid petroleum gas (LPG) organic vapors (ethanol, formaldehyde) and the like.

For detection and quantification of carbon dioxide in gas mixtures, there are two types of conventional sensors, i.e. infrared spectroscopy (IR) based sensors and electrical resistance based metal oxide semiconductor (MOS) sensors. The IR sensors take advantage of the large IR stretching band for C=O functionality at 2349 $cm^{-1}$. Although commercially available portable IR sensors exist, this approach is still limited by its power consumption, size and cost. The MOS sensors utilize the change of electrical resistance of a semiconductor film in the presence of carbon dioxide. These sensors are also commercially available. However, since such sensors operate at high temperatures, they increase the power consumption.

There is a need for new or improved sensors that can be used for fuel cell equipment in monitoring the hydrogen concentration in the fuel stream (thereby its purity) and detection of equipment leakages.

Detection and quantification of ethanol is also becoming important for a variety of purposes including ethanol production, chemical processing, fuel processing and use, societal applications, and physiological research on alcoholism. A large number of commercial ethanol measurement systems are available for several of these applications. However, in general, these systems are designed exclusively for vapor-phase measurements, operate at relatively high power levels, are bulky, and possess functionality that is more limited than required for a number of applications. For the most precise measurements, high performance liquid chromatography (HPLC) and infrared spectroscopy (IR) can be used for ethanol concentration measurements. However, these are expensive and involve large equipment. For portable detection, smaller handheld devices such as breathalyzers are used for measurements that are proportional to blood alcohol concentration (BAC). Breathalyzer devices acquire ethanol from exhaled breath and require direct and intimate exhalation into the apparatus. Different versions of these devices have been integrated into some models of various commercial vehicles. The driver is required to breathe into a special mouthpiece to measure the level of alcohol in the breath, and a computer decides whether or not to allow the engine to start. In all these cases the measured breath alcohol is indiscreet and can be difficult to correlate to the blood alcohol concentration, since there can be a lot of variation in the breath collection method. Moreover, while semiconductor metal oxides such as $SnO_2$ and ZnO have typically been employed for alcohol sensing, these materials operate at elevated temperatures (>150° C.) and are sensitive to adsorption of other gaseous species apart from ethanol such as gasoline, CO, hydrocarbons and hydrogen which interfere with the alcohol measurements.

With the increasing demand for superior but inexpensive gas sensors of higher sensitivity and greater selectivity, intense efforts are being made to find more suitable materials with the required surface and bulk properties for use in gas sensors.

The carbon nanotubes (CNTs) are investigated as materials suitable for manufacturing such sensors. For example, Robinson et al. in "Improved Chemical Detection Using Single-Walled Carbon Nanotube Network Capacitors" Sensors and Actuators A, volume 135, pages 309 to 314 (2007); Varghese et al. in "Gas Sensing Characteristics of Multi-wall Carbon Nanotubes" Sensors and Actuators B, volume 81, pages 32 to 41 (2001); Valentini et al. in "Highly Sensitive and Selective Sensors Based on Carbon Nanotubes Thin Films for Molecular Detection" Diamond and Related Materials, volume 13, pages 1301 to 1305 (2004); Snow et al. in "Chemical Vapor Detection Using Single-Walled Carbon Nanotubes" Chemical Society Reviews, volume 35, pages 790 to 798 (2006); and Star et al. in "Gas Sensor Array Based on Metal-Decorated Carbon Nanotubes" Journal Physical Chemistry B, volume 110, pages 21014 to 21020 (2006) have described the detection and quantification of gaseous species in gas mixtures by sensors manufactured by using CNTs.

Sensors arrays have also been proposed for detection or determination of concentration of more than one analyte, e.g. by Lu et al., in "A carbon nanotube sensor array for sensitive gas discrimination using principal component analysis", J. Electrochem. Chem., volume 593, pages 105 to 110 (2006); by Qi et al. in "Toward Large Arrays of Multiplex Functionalized Carbon Nanotube Sensors for Highly Sensitive and Selective Molecular Detection", Nano Lett., volume 3, pages 347 to 351 (2003); and by Graf et al., in "Smart single-chip CMOS microhotplate array for metal-oxide-based gas sensors" 12th International Conference on Transducers, Solid-State Sensors, Actuators and Microsystems, volume 1, pages 123 to 126 (2003).

Methods of preparation of variety of sensors and sensor arrays have also been proposed, for example, by Eranna et al., in "Oxide Materials for Development of Integrated Gas Sensors—A Comprehensive Review", Critical Reviews in Solid State and Materials Sciences, volume 29, pages 111 to 188 (2004); and by Sabate et al., in "Multisensor Chip for Gas Concentration Monitoring in a Flowing Gas Mixture", Sensors and Actuators B, volume 107, pages 688 to 684 (2005).

In summary, in all these applications, there is a high demand for improved sensitivity, accuracy, reliability, selectivity and stability beyond what is currently offered by commercially available sensors. There exists a need for new or improved sensor devices for detecting analyte gas.

SUMMARY OF THE INVENTION

Figure 1:
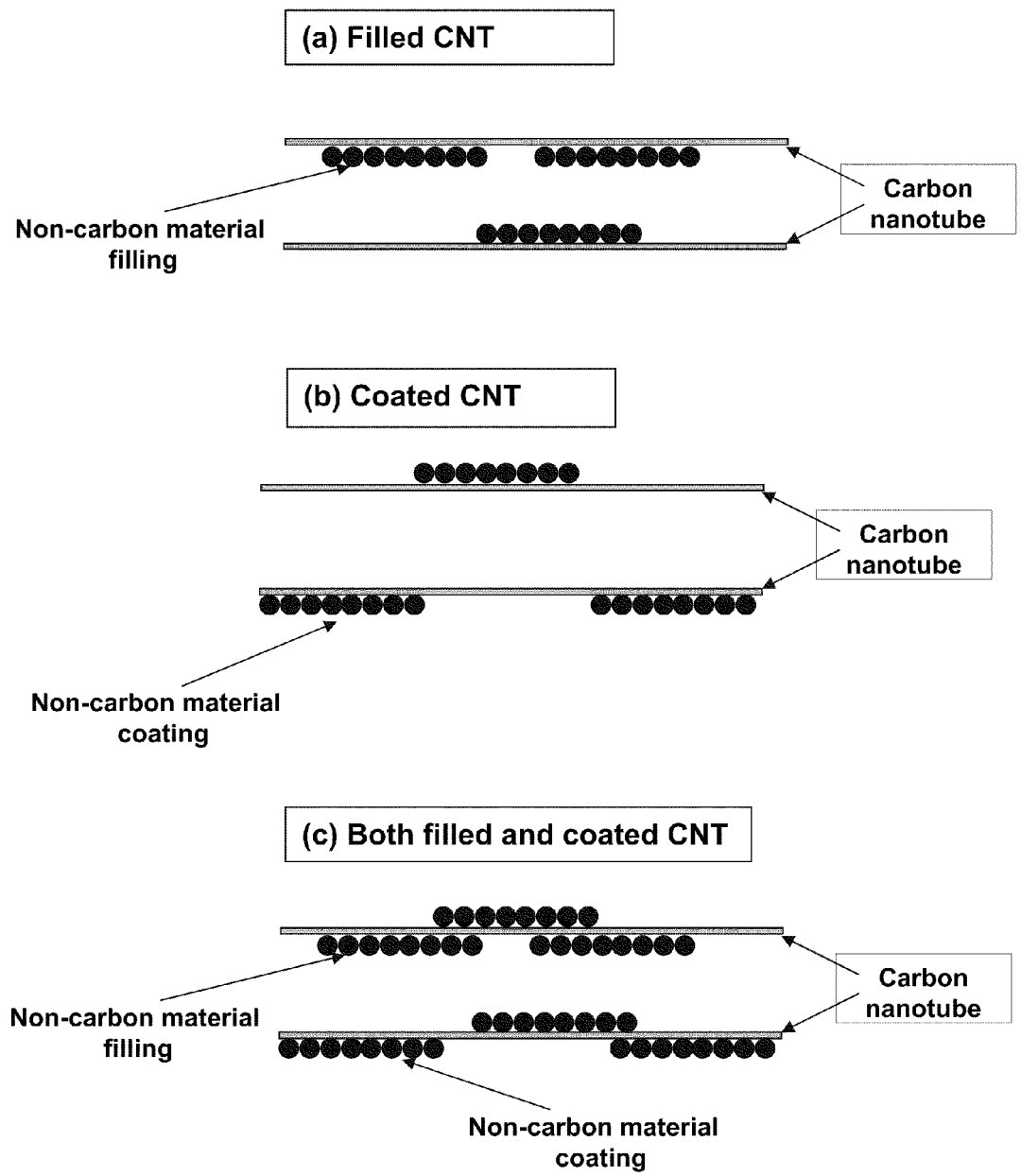
FIG. 1 is a schematic diagram of the types of the organized carbon and non-carbon assembly of the instant invention.

The present invention is directed to a device for detecting an analyte gas. The device is comprises (a) a sensor comprising a carbon nanotube filled with one or more non-carbon materials comprising a titanium compound, zirconium, zirconium hydride, hafnium, hafnium hydride, vanadium, vanadium hydride, a manganese compound, iron, iron hydride, cobalt, cobalt hydride, nickel, nickel hydride, palladium, palladium hydride, platinum, platinum hydride, copper, copper hydride, zinc, zinc hydride, or the combination thereof; and (b) an analysis unit connected to the sensor, the analysis unit detects or determines the concentration of the analyte gas in a background gas by measuring the Electronic Property Response of the sensor due to the analyte gas; wherein the sensor and the analysis unit are designed in such way that the average Electronic Property Response is $\geq 1\%$ when the analyte gas has a concentration of 10, 25, 50, 75, and 100 ppm.

The carbon nanotube of the sensor is a single wall carbon nanotube or a multi wall carbon nanotube. Preferably, the carbon nanotube is a single wall carbon nanotube with an outer diameter varying in the range of 1.0 nm to 1.8 nm. The Electronic Property Response that the analysis unit measures includes, but is not limited to, Resistive Response, Resistive Response derived from Circuit, or Capacitive Response derived from Circuit.

The present invention is also directed to an array sensor device, which comprises the above-described device and one or more sensors each comprising a carbon nanotube or a filled carbon nanotube.

The devices of the present invention also comprise carbon nanotubes further coated with a second non-carbon material comprising a second titanium compound, zirconium, zirconium hydride, hafnium, hafnium hydride, vanadium, vanadium hydride, a second manganese compound, iron, iron hydride, cobalt, cobalt hydride, nickel, nickel hydride, palladium, palladium hydride, platinum, platinum hydride, copper, copper hydride, zinc, zinc hydride, or the combination thereof.

The device of the present invention is suitable for detection or quantification of analyte gases such as nitrogen oxide, ethanol vapor, hydrogen, carbon dioxide, or oxygen.

DETAILED DESCRIPTION OF THE INVENTION

Definitions

In order to provide a clear and consistent understanding of the specification and claims, including the scope given to such terms, the following definitions are provided:

An "Electronic Property Response" as used herein, refers to a normalized electronic property variation of a sensor due to the presence of an analyte gas. It is calculated as:

Electronic Property Response (%)=$100 \times \Delta E/E_b$ $E_b$ is an electronic property of the background gas. $E_{mix}$ is the electronic property of the mixture gas that contains the analyte gas and the background gas. $\Delta E = E_{mix} - E_b$, which is the variation of the electronic property of the sensor (i.e. the sensor response) due to the analyte gas.

An Electronic Property Response includes, but is not limited to, Resistive Response, Resistive Response derived from Circuit, or Capacitive Response derived from Circuit.

An "enhancement factor," as used herein, quantifies the degree of improvement or attenuation in the sensor's response to an analyte gas due to incorporation of one or more non-carbon materials into a carbon nanotube over a range of various concentrations. An enhancement factor can be determined by dividing the sensitivity of a sensor comprising filled or filled and coated carbon nanotube by that of a sensor comprising the starting carbon nanotube.

The "minimum detection limit" of a sensor, as used herein, is calculated by using the Nyquist plots as follows.

Minimum Detection Limit=the lowest resistive resolution of the analyzer in ohms×10 ppm/$\Delta Z'$ where $\Delta Z' = Z'_b - Z'_{mix}$, and $Z'_b$ and $Z'_{mix}$ are the real (resistive) parts of the impedance curves for the background gas and for the 10 ppm analyte gas (in background gas) respectively in ohms. The calculation of Minimum Detection Limit is illustrated in Example 12.

The "sensitivity of a sensor" as used herein, is calculated from the slope of the Electronic Property Response vs. the analyte gas concentration curve, for example, by using the following formulae:

Resistive Sensitivity(Circuit)=$\Delta$Resistive Response (Circuit)/$\Delta$ppm of analyte gas Capacitive Sensitivity(Circuit)=$\Delta$Capacitive Response (Circuit)/$\Delta$ppm of analyte gas A "sensor" as used herein, refers to a solid material that has one or more electronic properties that are affected by the surrounding gas.

This invention is directed to a sensor device for detecting one or more analyte gases. The device comprises a sensor and an analysis unit. The sensor comprises organized assemblies of carbon and non-carbon materials. The sensor preferably comprises a carbon nanotube filled with one or more non-carbon materials. The analysis unit is connected to the sensor, and detects or determines the concentration of the analyte gas in a background gas by measuring the Electronic Property Response of the sensor due to the analyte gas. In the present invention, the sensor and the analysis unit are designed such that the average Electronic Property Response is ≧1% when the analyte gas has concentrations of 1-100 ppm, for example, 10, 25, 50, 75, and 100 ppm.

Organized Assemblies

These organized assemblies are made up of one or more types of a repeating unit and may adopt different shapes, such as a rod, spherical, semi-spherical, or egg shape. At least one dimension of the repeating unit is typically smaller than 1000 nm, preferably smaller than 100 nm, or more preferably smaller than 10 nm. A cross-section of a repeating unit may resemble a circular, oval, or rectangular shape. Typically, individual repeating units (or different types of repeating units) aggregate to nanometer size fragments. In a preferred embodiment, a repeating unit of this invention may be a nanorod comprising nanocarbon and non-carbon materials.

Many forms of carbon are suitable for the sensor of this invention. These forms of carbon include for example amorphous carbon, graphite, MWCNTs, SWCNTs, or a mixture thereof. In preferred embodiments of this invention, the carbon may be a MWCNT, a SWCNT, or a mixture thereof. In another preferred embodiment of this invention, the carbon may be a SWCNT. In yet another preferred embodiment, the carbon may be a SWCNT that has an external diameter varying in the range of 1 nanometer to 1.8 nanometers.

Many non-carbon materials are suitable for incorporation into the carbon nanotubes of this invention. Non-carbon materials may comprise a metal (or a metal compound) or a non-metal material. For example, a non-carbon material may comprise a metal, metal like compound, metal nitride, metal oxide, metal hydride, metal boride, mixture, or alloy thereof.

Some examples of a non-carbon material include magnesium (Mg), magnesium hydride, magnesium diboride ($MgB_2$), magnesium nitride ($Mg_3N_2$), magnesium oxide (MgO), strontium (Sr), scandium (Sc), scandium nitride (ScN), yttrium (Y), titanium (Ti), titanium hydride, titanium nitride (TiN), titanium diboride ($TiB_2$), titanium oxide ($TiO_2$), zirconium (Zr), zirconium diboride ($ZrB_2$), zirconium nitride (ZrN), hafnium (Hf), hafnium nitride (HfN), vanadium (V), vanadium diboride ($VB_2$), niobium (Nb), niobium diboride ($NbB_2$), niobium nitride (NbN), tantalum (Ta), chromium (Cr), chromium diboride ($CrB_2$), manganese (Mn), iron (Fe), cobalt (Co), nickel (Ni), palladium (Pd), platinum (Pt), boron (B), boron hydrides, boron nitride (BN), boron oxide ($B_2O_3$), and a mixture (or alloy) thereof. Non-stoichiometric compounds of the non-carbon material are also within the scope of this invention. In addition, the non-carbon material may be amorphous or crystalline. The crystalline form could be distorted, for example by having deficiencies in the crystal structure. In the instant invention, the non-carbon material does not comprise a halogen and/or a halogenated compound.

In one embodiment of this invention, the non-carbon material comprises a titanium compound. A titanium compound, as used herein, refers to a compound that contains titanium. For example, a titanium compound may be titanium, a titanium hydride, a titanium boride, a titanium nitride, a titanium oxide, or a mixture thereof. In particular, a titanium compound may be abbreviated with a formula $TiH_wB_xN_yO_z$, where w varies in the range of 0 to 2, x varies in the range of 0 to 2, y varies in the range of 0 to 1, and z varies in the range of 0 to 2. Non-stoichiometric titanium compounds are also within the scope of this invention. For example, the titanium compound may be $TiO_{1.354}$.

In another embodiment of this invention, the non-carbon material comprises a manganese compound. A manganese compound, as used herein, refers to a compound that contains manganese. For example, a manganese compound may be manganese, a manganese hydride, a manganese nitride, a manganese oxide, or a mixture thereof. In particular, a manganese compound may be abbreviated with a formula $MnH_{w'}B_{x'}N_{y'}O_{z'w'}$, Where w' varies in the range of 0 to 4, x' varies in the range of 0 to 2, y' varies in the range of 0 to 1, and z' varies in the range of 0 to 2. Non-stoichiometric manganese compounds are also within the scope of this invention. For example, the manganese compound may be $MnO_{1.782}$.

The non-carbon material may also comprise limited amount of metal carbides, such as titanium carbide, silicon carbide, vanadium carbide, tantalum carbide, or a mixture thereof, with an amount preferably less than 10 volume percent.

As a repeating unit, the non-carbon material may fill, coat, or both fill and coat the carbon nanotube (CNT). These three cases are schematically shown in FIG. 1 (a) to (c). In the first case shown in FIG. 1(a), the non-carbon material fills the core of the CNT. The articles of the first case are abbreviated hereafter as "non-carbon material filled carbon," for example, as Ti filled SWCNTs. In the second case shown in FIG. 1(b), the non-carbon material coats the CNT. The articles of this case are hereafter abbreviated as "non-carbon material coated carbon," for example, as Ti coated SWCNTs. In the third case shown in FIG. 1(c), the non-carbon material both fills and coats the CNT. The articles of this case are hereafter abbreviated as "non-carbon material filled and coated carbon," for example, as Ti filled and coated SWCNTs. The sensor of the present invention preferably comprises carbon nanotubes filled with one or more non-carbon materials. The filled nanotubes are optionally coated with one or more non-carbon materials.

The repeating unit may be partially hollow. For example, the core of a SWCNT, may be partially empty. The empty portion of the core may be in less than 95, 75, 50, 25, or 10 volume percent. The coating, filling, or coating and filling by the non-carbon material may have a continuous or non-continuous form. For example, they may be in the form of a continuous film deposited on the outer or inner surface of a SWCNT, islands deposited on the outer or inner surface of a SWCNT, beads deposited on the surface of a SWCNT, or particulates deposited in the core of a SWCNT.

Method for Preparing an Organized Assembly

The organized assembly of carbon and non-carbon materials of the present invention is prepared by the following method.

The method comprises the steps of reacting a carbon precursor with a halogenated precursor to generate a halogenated intermediate and removing halogen from the halogenated intermediate to obtain the organized assembly of the carbon and the non-carbon materials (hereinafter "the halide method"). If the non-carbon material includes a hydride, nitride, oxide, or a mixture thereof, the method may further comprise the step of hydrogenation, nitrogenation, and/or oxidation after the halogen removal step to obtain a composition comprising (1) carbon and (2) a non-carbon hydride, boride, nitride, oxide, or a mixture thereof. In the instant invention, the non-carbon material is not a halogen.

Many forms of the carbon precursor are suitable for the halide method. In a preferred embodiment, these forms of carbon precursors comprise a MWCNT, a SWCNT, or a mixture thereof. These carbon precursors are hereafter referred as "carbon nanotubes" or "starting carbon nanotubes", for example, a carbon nanotube, MWCNTs, starting MWCNTs, SWCNTs, or starting SWCNTs.

A SWCNT or MWCNT precursor suitable for this invention may be prepared by any synthesis method. Such methods may include, but are not limited to, carbon arc, laser vaporization, chemical vapor deposition (CVD), high pressure carbon monoxide process (HiPco), cobalt-molybdenum catalyst process (CoMoCat). A SWCNT precursor may be a mixture of SWCNT precursors prepared by more than one synthesis method.

In one preferred embodiment of this invention, the carbon precursor may comprise a SWCNT. In another preferred embodiment, the carbon precursor may comprise a SWCNT that has an external diameter varying in the range of 1 nanometer to 1.8 nanometers.

In one embodiment of the halide method, the SWCNT precursor may be used as purchased. In another embodiment, amorphous carbons and/or catalysts may be removed from the as-purchased SWCNTs before the application of the disclosed method. The amorphous carbon and/or the catalyst removal may be complete or partial. Thus, a SWCNT precursor may contain any level of amorphous carbon and/or catalyst. The invention is not limited to any particular method of removing the amorphous carbon and/or the catalyst from the starting SWCNTs. As an example, the method disclosed by Delzeit et al. in U.S. Pat. No. 6,972,056 may be used for this removal.

A halogenated precursor may comprise a halogenated compound and a halogen. Examples of the halogenated compound include magnesium iodide ($MgI_2$), scandium iodide ($ScI_3$), scandium bromide ($ScBr_3$), yttrium iodide ($YI_3$), titanium iodide ($TiI_4$), titanium bromide ($TiBr_4$), vanadium iodide ($VI_3$), vanadium bromide ($VBr_3$), molybdenum iodide ($MoI_3$), manganese iodide ($MnI_2$), iron iodide ($FeI_2$), cobalt iodide ($CoI_2$), nickel iodide ($NiI_e$), palladium iodide ($PdI_2$), platinum iodide ($PtI_2$), boron iodide ($BiI_3$), lead iodide ($PbI_2$), bismuth iodide ($BiI_3$) or a mixture thereof. Examples of the halogen include iodine, bromine, an interhalogen compound (such as IBr, $ICl_3$, $BrF_3$) or a mixture thereof.

Ends of the as-purchased carbon nanotubes are typically closed, i.e. they are end-capped. The end-caps may prevent direct filling of cores of the as-purchased carbon nanotubes with the non-carbon materials. In some previously disclosed filling methods, the end-caps are removed prior to the filling step by using acids such as nitric acid or by controlled oxidation at elevated temperatures. Such end-cap removal methods may cause partial or excessive removal of carbon and formation of defects, thereby degrading the useful properties of the carbon nanotubes.

The presence of the halogen in the halogenated precursor may aid in filling of the carbon nanotubes with the non-carbon materials without necessitating a separate end-cap removal step prior to the filling, thereby simplifying the process. Also, such filling may be achieved without any degradation of useful properties of the carbon nanotubes. The presence of halogen may also increase the amount of filling of carbon nanotubes by non-carbon materials, thereby improving the yield and desired properties of the organized assembly. Furthermore, the presence of halogen may decrease the viscosity of the halogenated precursor, thereby promoting better infiltration and shorter process duration.

Some halogenated compounds may have impractically high melting points (e.g., 587° C. for $FeI_2$, 780-797° C. for $NiI_2$, 613-638° C. for $MnI_2$), and if the reaction is carried out at such high temperatures, the carbon nanotubes may irreversibly be damaged, diminishing the useful properties of the organized assembly. However, incorporating halogens such as bromine with a melting point of −7.3° C. or iodine with a melting point of 113.6° C. into the halogenated precursor may substantially reduce the reaction temperature and prevent any property degradation.

Thus, there are several advantages of incorporating a halogen into the halogenated precursor, including achieving filling with no end-cap removal prior to the filling, increasing the filling yield, and reducing the reaction temperature and time.

The amount of the halogenated compound in a halogenated precursor may be at least 0.001 weight %. In other embodiments, the amount of the halogenated compound in a halogenated precursor may be at least 0.01 weight %, 0.1 weight %, 1 weight %, 10 weight %, 50 weight %, or 80 weight %. The amount of halogen in a halogenated precursor may be at least 0.001 weight %. In other embodiments, the amount of halogen in a halogenated precursor may be at least 0.01 weight %, 0.1 weight %, 1 weight %, 10 weight %, 50 weight %, or 80 weight %.

The amount of non-carbon material present in the halogenated precursor controls the amount of non-carbon material incorporated into the assembly. Thus, by varying the ratio of the non-carbon material amount to the carbon precursor, the non-carbon material content of the final composition can be varied. The ratio of non-carbon material present in the halogenated precursor to carbon present in the carbon precursor may be at least 0.01 weight %. In other embodiments, the ratio of non-carbon material present in the halogenated precursor to carbon present in the carbon precursor may be at least 1 weight %, 10 weight %, or 25 weight %.

As a first process step, a carbon precursor is reacted with a halogenated precursor. This reaction results in the incorporation of the carbon precursor with the halogenated precursor to form a halogenated intermediate. This incorporation may be in any form. For example, the halogen may be incorporated on the outer or inner surface or into the chemical structure of the carbon precursor. This incorporation may be through chemical or physical bonding.

The reaction between the carbon precursor and the halogenated precursor may occur at a temperature at which the halogenated precursor is a liquid. Typically, it is at or above the melting temperature of the halogenated precursor. In one embodiment, the carbon precursor and the halogenated precursor may be reacted at a temperature above 20° C., 100° C., 150° C., or 200° C. for a period longer than 1 minute, 10 minutes, or 20 minutes.

In an optional process step, the carbon precursor may be heated above room temperature to remove volatile compounds, such as water, before the step of reacting the carbon precursor with the halogenated precursor. The volatile compound removal may be achieved by heating the carbon precursor above 100° C. or 200° C. for a period longer than 10 minutes.

After the reaction between the carbon precursor and the halogenated precursor, a halogenated intermediate is produced.

As a second process step, the halogen is removed from the halogenated intermediate. It is expected that, during the reaction, the halogenated precursor may open the end caps of the carbon nanotubes and fill their cores, coat the carbon nanotube, or both fill (i.e., intercalate) and coat the carbon nanotube. As a result, the halogenated intermediate may contain halogen, in a free form, such as iodine, and/or in a form incorporated with the non-carbon compound, such as $TiI_4$. The presence of the halogen in the final assembly in high quantities may deteriorate its properties as compared to the halogen free assembly. It may be necessary to reduce the halogen level, for example, below 10 weight %, to obtain a commercially viable product.

The halogen removal may be achieved by sublimation, evaporation, or thermal degradation. The halogen removal may also be achieved by reacting the halogenated intermediate with a suitable reactant, for example, hydrogen.

In particular, the halogen removal step may comprise heating the halogenated intermediate at a temperature for a period sufficient enough to reduce the halogen content of the intermediate below 10 weight %. For example, the halogen removal step may be carried out at a temperature above 200° C., 300° C., 500° C., or 800° C. for a period longer than 5 minutes, 10 minutes, 30 minutes, or 1 hour. This heating may be carried out below 1 atmosphere pressure. In one embodiment, this heating may be carried out in a gas mixture comprising hydrogen at a temperature for a period sufficient enough to reduce the halogen content of the intermediate below 10 weight %. For example, the halogen removal step may be carried out in a gas mixture comprising at least 0.01 volume % or 1 volume % hydrogen at a temperature above 200° C., 300° C., 500° C., or 800° C. for a period longer than 5 minutes, 10 minutes, 30 minutes, or 1 hour. The heating may be carried out below 1 atmosphere pressure. By adjusting these halogen removal conditions, the level of hydride formation can be controlled and as a result essentially hydride-free or partially or fully hydrogenated forms of the non-carbon material may be obtained.

After the halogen removal step, an organized assembly comprising a carbon and a non-carbon material (such as metal, metal like compound, metal boride, or a mixture thereof) is obtained. Specific examples of such non-carbon material include magnesium (Mg), magnesium diboride ($MgB_2$), strontium (Sr), scandium (Sc), yttrium (Y), titanium (Ti), titanium diboride ($TiB_2$), zirconium (Zr), zirconium diboride ($ZrB_2$), hafnium (Hf), hafnium nitride (HfN), vanadium (V), vanadium diboride ($VB_2$), niobium (Nb), niobium diboride ($NbB_2$), tantalum (Ta), chromium (Cr), chromium diboride ($CrB_2$), manganese (Mn), iron (Fe), cobalt (Co), nickel (Ni), palladium (Pd), platinum (Pt), boron (B), boron nitride (BN), and a mixture thereof.

For an organized assembly comprising (1) a carbon and (2) a non-carbon hydride, boride, nitride, oxide, or a mixture thereof, the method may further include hydrogenation, reaction with boron compounds, nitrogenation, and/or oxidation of the product after the halogen removal step. This is an optional step for some hydrides and borides. For example, if the halogen removal step is carried out in a gas mixture comprising hydrogen, the non-carbon hydrides may readily be obtained after the halogen removal without necessitating this additional step. Also, if the halogenated precursor includes a boron compound, the borides may also readily be obtained after the halogen removal step without necessitating this additional step. The hydrogenation may be carried out above room temperature in a gas mixture containing hydrogen, ammonia, or hydrazine. A preferable hydrogenation temperature is below 500° C. In one embodiment of this invention, a hydrogenation temperature in the range of 100° C. to 300° C. may also be applied. The reaction with boron compounds may be carried out by reacting the product with boron hydrides, for example $B_2H_6$, $B_5H_{11}$. The nitrogenation may be carried out above room temperature in a gas mixture containing nitrogen, ammonia, hydrazine, or a mixture thereof. The oxidation may be carried out at room temperature or above in a gas mixture containing oxygen. As a result of hydrogenation, reaction with boron compounds, nitrogenation, and/or oxidation, the assembly comprising (1) a carbon and (2) a non-carbon (such as metal) hydride, boride, nitride, oxide, or a mixture thereof is formed. Some examples of such non-carbon material include magnesium hydride ($MgH_2$), magnesium nitride ($Mg_3N_2$), magnesium oxide (MgO), scandium nitride (ScN), titanium hydride ($TiH_2$), titanium nitride (TiN), titanium oxide ($TiO_2$), zirconium nitride (ZrN), hafnium nitride (HfN), niobium nitride (NbN), boron hydrides, boron nitride (BN), boron oxide ($B_2O_3$), and a mixture thereof.

In one embodiment of the halide method, the organized assembly comprising non-carbon material filled and coated carbon, such as Ti filled and coated SWCNT may be prepared by both filling and coating the carbon nanotube by the halogenated compound. To achieve the filling, the size of the core should be larger than the size of the halogenated compound. For example, a halogenated compound, $TiI_4$ has a size of about 1 nm. During the halogenation reaction, this compound can fill the cores of SWCNTs that have inner diameters larger than 1 nm. Thus, for example, since the SWCNTs prepared by the carbon arc process have inner diameters larger than 1 nm, these carbon precursors may be both filled and coated with $TiI_4$ and after the removal of iodine, Ti filled and coated SWCNTs are generated.

In another embodiment of the halide method, the non-carbon material coated carbon, such as Ti coated SWCNTs may be prepared by coating the carbon nanotube by the halogenated compound. To achieve the coating but not filling, the size of the core should be smaller than the size of the halogenated compound. For example, a halogenated compound $TiI_4$ has a size of about 1 nm and the SWCNTs prepared by CoMoCat process have inner diameters smaller than 1 nm. Then, it is expected that during the halogenation reaction, $TiI_4$ can coat but not fill the cores of these SWCNTs. As a result, after the iodine removal, Ti coated SWCNTs may be produced.

In yet another embodiment of the halide method, the non-carbon material filled carbon, such as Ti filled SWCNTs may be prepared by washing the halogenated compound coated and filled carbon nanotubes with a suitable solvent, such as ethanol. This washing may remove the halogenated compound coating, but not the filling at the carbon nanotube core. Then, after the halogen removal, Ti filled SWCNTs are produced. This washing may completely remove the halogenated compound coating if a suitable solvent is used and/or if the solvent washing step is repeated several times. This washing may also partially remove the halogenated coating, for example, thereby incorporating a coating that has a particulate form to the carbon. The amount of the coating then may be varied by controlling the solvent type, solvent amount, and number of repetition of washing steps.

Thus, by choosing the core size of the carbon nanotube or incorporating a solvent wash step when the core size is larger than size of the halogenated compound, the form of non-carbon material incorporation may be controlled to prepare non-carbon filled, coated, both filled and coated carbon assemblies, or their mixtures.

In one embodiment of the invention, the method comprises first filling the carbon nanotube and then further filling and/or coating the filled carbon nanotube with a second non-carbon material. The further filling and/or coating with the second non-carbon may be achieved by following the method disclosed above.

Sensor Device

This invention is particularly directed to a sensor device comprising a sensor and an analysis unit. A "sensor," as used herein, refers to a solid material that has one or more electronic properties that are affected by the surrounding gas(es). The sensor comprises a carbon nanotube filled with one or more non-carbon materials. The analysis unit measures electronic properties of the sensor. The device detects or quantifies an analyte gas by measuring variation of an electronic property of the sensor as explained below.

The sensors of this invention are used for detection or quantification of analyte gases (or vapors) such as $NO_2$, ethanol, hydrogen, carbon dioxide and oxygen that may be present in the environment surrounding the sensor. In a preferred embodiment of this invention, the sensor comprises a carbon nanotube filled with one or more non-carbon materials comprising a titanium compound, zirconium, zirconium hydride, hafnium, hafnium hydride, vanadium, vanadium hydride, a manganese compound, iron, iron hydride, cobalt, cobalt hydride, nickel, nickel hydride, palladium, palladium hydride, platinum, platinum hydride, copper, copper hydride, zinc, zinc hydride, or the combination thereof.

These sensors may have any structure suitable for detection or quantification of an analyte gas. In one embodiment of this invention, the sensor comprises a repeating unit of the organized carbon and non-carbon assembly. For example, the sensor comprises a Ti filled SWCNT. A single repeating unit of the organized assembly may also work as a sensor and thereby it is within the scope of this invention. For example, the sensor may be one Ti filled SWCNT. The repeating unit may also be combined with other materials, for example with polymers, metals or metal oxides to form the sensors of this invention. A coating comprising the repeating unit of the organized assembly on a suitable substrate (for example, a glass slide) may also form the sensor. There may be many more forms of the sensor. All of them are within the scope of this invention.

The sensors of this invention may be prepared by any method suitable for the present invention. The sensor can be prepared by depositing the sensing material (e.g., the filled carbon nanotube) over electrodes by sputtering, printing or dropping methods. One method of preparation of a sensor is illustrated in Example 10 below and schematically shown in FIG. 2. There may be many more methods for preparation of the sensors of this invention. All of them are within the scope of this invention.

Analysis Unit

The sensors of this invention detect or quantify an analyte gas by using an analysis unit that measures the variation of an electronic property of the sensor caused by the presence of the analyte gas. First, an electronic property of the background gas, i.e. $E_b$ is measured. Then, the electronic property of the gas that contains the analyte gas and the background gas, i.e. $E_{mix}$ is measured. The difference between these two measurements, i.e. $\Delta E = E_{mix} - E_b$ is the variation of the electronic property of the sensor (i.e. the sensor response). The variation might be negative or positive, depending on the electronic property measured. Both variations are within the scope of this invention. The absolute value of the variation is used hereafter.

This is explained in a simplified example as follows. A sensor has an electronic property of electrical resistance. To measure the concentration of an analyte gas ($NO_2$) in a background (nitrogen) gas, an analysis unit first measures the electrical resistance of this sensor in nitrogen as 100 ohm. The analysis unit then measures the electrical resistance of the sensor in $NO_2$-nitrogen gas as 101 ohm. Then, the analysis unit determines the variation of the electric resistance by subtracting 100 ohm from 101 ohm, which equals to 1 ohm. This 1 ohm variation is due to the presence of $NO_2$.

The normalized sensor response is defined as:

$$\text{Electronic Property Response}(\%) = 100 \times \Delta E / E_b$$

There may be many electronic property variations that can be measured by the analysis unit. In one embodiment of this invention, the detection or quantification is determined by measuring the variation of electrical resistance of the sensor. This variation is hereafter abbreviated as "Resistive Response".

Figure 3:
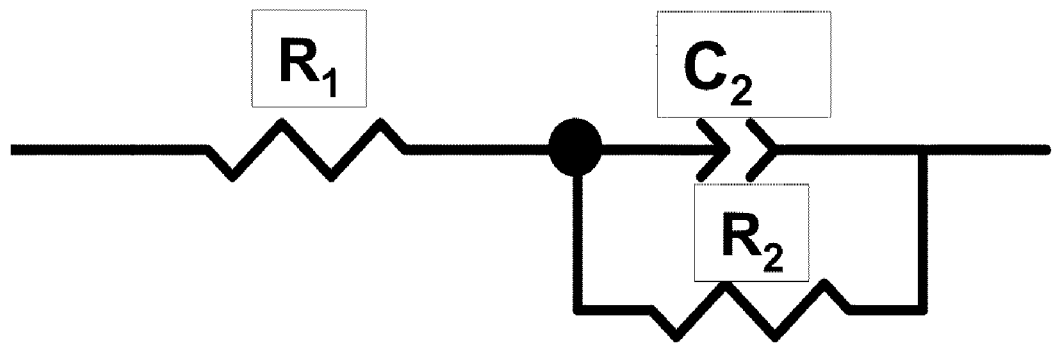
FIG. 3 schematically shows the model electrical circuit used to analyze the responses of various sensors comprising the organized carbon and non-carbon assemblies.

In another embodiment, the detection or quantification is determined by measuring the variation of resistive and capacitive properties derived from a model electrical circuit. One example of such model electrical circuit, shown in FIG. 3, is formed by a resistor $R_1$, another resistor $R_2$, and a non-Debye capacitor $C_2$. The values of $R_1$, $R_2$ and $C_2$ for each sensor in response to each analyte and analyte concentration are obtained by first resolving the total impedance (Z) into a real part (Z') and an imaginary part (Z"), then plotting the imaginary part against the real part (i.e. Nyquist plot), and finally fitting this plot to the model electrical circuit by using a suitable software.

The variations measured by using this method are hereafter abbreviated as "Resistive Response (Circuit)" and "Capacitive Response (Circuit)". There may be many such equivalent circuits that can be used for the electronic property variation measurement. All these circuits are within the scope of this invention.

There may be many more electronic property variations that can be measured by the analysis unit. All these electronic property variations that can be used to detect or quantify the analyte gas are within the scope of this invention.

In the present invention, the sensor and the analysis unit are designed in such a way that the average Electronic Property Response is ≧1% when the analyte gas has concentrations of 1-100 ppm. This limitation ensures that the device of the present invention detects a sufficient normalized variation of the electronic property above the background noise due to a particular analyte gas, such that the result is accurate and reliable. The average Electronic Property Response is determined by averaging the Electronic Property Responses when the analyte gas concentrations are between 1-100 ppm; preferably, determined by averaging at least 3, 4, or 5 analyte gas concentrations throughout the entire range, for example, at 10, 25, 50, 75, and 100 ppm.

When a sensor has a particular average Electronic Property Response of less than 1% averaged in the analyte concentration range of 1 ppm to 100 ppm (e.g., 10, 25, 50, 75, and 100 ppm), this variation is negligible above the background noise and thereby the device is not sufficient for detection or quantification of the analyte gas. Therefore, a sensor device comprising only one such sensor and an analysis unit that measures the variation of this particular electronic property is not within the scope of this invention. For example, as disclosed below in Example 12, a manganese filled and coated SWCNT sensor had Capacitive Responses (Circuit) of 0.034%, 0.102%, 0.135%, 0.237%, and 0.270% at $NO_2$ concentrations of 10, 25, 50, 75, and 100 ppm respectively. Thus, the average Capacitive Response (Circuit) for this sensor was 0.156% at the $NO_2$ concentrations ranging from 1 to 100 ppm. Therefore, the sensor device comprising one manganese filled and coated SWCNT sensor and an analysis unit that measures the Capacitive Response (Circuit) can not detect or quantify $NO_2$. This sensor device is thereby not within the scope of this invention.

However, such sensor can be used together with other analysis units that measure variation of other electronic properties. Such devices are within the scope of this invention. For example, as disclosed below in Example 12, a manganese filled and coated SWCNT sensor had an average Resistive Response (Circuit) higher than 1% at $NO_2$ concentrations 10, 25, 50, 75, and 100 ppm. The sensor device comprising one manganese filled and coated SWCNT sensor and an analysis unit that measures the Resistive Response (Circuit) may detect or quantify $NO_2$. This sensor device is thereby within the scope of this invention.

Furthermore, such sensors can also be used together with other types of sensors in a sensor array to detect or quantify gas mixtures comprising more than one analyte. This embodiment of this invention is explained by way of example in Example 21 in detail.

As explained below, it was found that most of the sensors comprising the organized assemblies of this invention had Electronic Property Responses improved over the sensors comprising as purchased SWCNTs (i.e. starting SWCNTs). For example, the Resistive Response (Circuit) of the starting SWCNTs is very low, less than 2% to ethanol vapor, less than 1.5% to hydrogen, less than 2.5% to carbon dioxide, less than 2.6% to oxygen in the analyte concentration range of 1 ppm and 100 ppm. Most of the sensors comprising the organized assemblies had higher Resistive Responses (Circuit) to these analytes, as explained in detail in Examples below.

Therefore, in one preferred embodiment of this invention, the device of the present invention comprises a sensor that comprises a carbon nanotube filled, or filled and coated with one or more non-carbon materials; the sensor yields an electronic variation (i.e. Electronic Property Response) higher than that of a sensor comprising only carbon nanotubes that do not contain non-carbon material (i.e. the starting carbon nanotube). This preferred sensor of the present invention, for example, has Resistive Responses, Resistive Responses (Circuit) and/or Capacitive Responses (Circuit) higher than those of the sensor comprising only carbon nanotubes. This preferred sensor of the present invention also has sensitivities higher than those of the sensor comprising only carbon nanotubes. This preferred sensor of the present invention has enhancement factors higher than 1.00.

As also explained below, the Starting SWCNT sensors sometimes had Electronic Property Responses better than those of a few sensors comprising the organized assemblies of this invention. However, such sensors comprising the organized assemblies of this invention may have better sensitivities at certain analyte concentrations as compared to the Starting SWCNT sensors. Therefore, such sensors are also within the scope of this invention.

The device determines the analyte concentration by calibrating the analysis unit. For example, the device may determine the analyte concentration by measuring the electrical resistance of the sensor as follows. First, the analysis unit measures electrical resistance $R_b$ of the sensor in a gas that does not contain an analyte gas (i.e. a background gas). This gas may be a single component gas or multi-component gas such as air. Next, a known amount of analyte gas is introduced into the background gas and the resistance of the sensor in this gas mixture $R_{mix}$ is measured. The difference between the two resistance values, $\Delta R = R_{mix} - R_b$ is caused by an increase in concentration of the known amount of analyte gas, which is hereafter abbreviated as $\Delta$ppm. The absolute Resistive Response of the sensor caused by the known amount of analyte concentration increase is:

$$\text{Resistive Response (calibration) (\%)} = 100 \times \Delta R / R_b$$

The ratio $\Delta$Resistive Response (calibration)/$\Delta$ppm is the Resistive Sensitivity of the sensor derived from electrical resistance measurements of the known amount of analyte concentrations. The Resistive Sensitivity value is used to determine unknown analyte concentration by simply dividing the Resistive Response of the sensor in the background gas that contains unknown amount of analyte concentration with the Resistive Sensitivity:

$$\text{Unknown Analyte Concentration(ppm)} = \text{Resistive Response(\%)/Resistive Sensitivity}$$

The sensitivity of each sensor may vary with varying analyte concentration and analyte type. This variation might be linear or non-linear. Therefore, the sensitivity variation for each analyte is determined for each sensor at a wide analyte concentration range before determination of the unknown concentration. The sensitivity vs. analyte concentration (i.e. calibration plots) thereby obtained may be used to determine the unknown concentration.

Sensor Device for Detection or Quantification of $NO_x$ Gas

In one embodiment, the devices of the instant invention are for detection or quantification of nitrogen oxide ($NO_x$) gases, such as nitric oxide (NO), nitrogen dioxide ($NO_2$), nitrous oxide ($N_2O$), dinitrogen trioxide ($N_2O_3$), dinitrogen tetraoxide ($N_2O_4$), dinitrogen pentoxide ($N_2O_5$), or mixtures thereof. In another embodiment, the $NO_x$ sensor device of this invention is suitable for detection or quantification of $NO_2$. In another embodiment, the $NO_x$ sensor device is suitable for detection or quantification of $NO_2$ in air.

These $NO_x$ sensor devices comprise a sensor and an analysis unit, and the sensor comprises a carbon nanotube filled with one or more non-carbon materials, as discussed above.

However, as disclosed below in Example 12 in detail, it was found that the contribution of $R_1$ to the Resistive Response (Circuit) was less than 0.03% when the response was averaged in the $NO_2$ concentration range of 1 ppm to 100 ppm. It was thereby concluded that the device comprising only one $NO_x$ sensor of this invention and the analysis unit that measures the Electronic Property Response $R_1$ is not within the scope of this invention. This device may be used together with other devices in an array device to detect or quantify gas mixtures comprising more than one analyte.

It was also found that a manganese filled and coated SWCNT sensor had a Capacitive Response (Circuit) less than 0.27% at the $NO_2$ concentrations ranging from 1 ppm to 100 ppm. Therefore, the sensor device comprising one manganese filled and coated SWCNT sensor and the Capacitive Response (Circuit) analysis unit is not within the scope of this invention. This device may be used together with other devices in an array device to detect or quantify gas mixtures comprising more than one analyte.

Sensor Device for Detection or Quantification of Ethanol Vapor

In one embodiment, the devices of the instant invention are for detection or quantification of ethanol vapor mixed with a background gas. These ethanol vapor sensor devices comprise a sensor and an analysis unit, and the sensor comprises a carbon nanotube filled with one or more non-carbon materials, as discussed above.

However, as disclosed below in Example 14 in detail, it was found that the contribution of $R_1$ to the Resistive Response (Circuit) was less than 0.03% when the response was averaged in the ethanol vapor concentrations ranging from 1 to 100 ppm. Likewise, the Capacitive Response (Circuit) $C_2$, was less than 1% when this response was averaged for this concentration range. It was thereby concluded that the device comprising only one ethanol vapor sensor of this invention and the analysis unit that measures the Electronic Property Response $R_1$ or the Capacitive Response (Circuit) is not within the scope of this invention. This device may be used together with other devices to detect or quantify gas mixtures comprising more than one analyte.

It was also found that a nickel filled and coated SWCNT sensor had a Resistive Response (Circuit) less than 0.53% at the ethanol vapor concentrations ranging from 1 to 100 ppm. Therefore the sensor device comprising one nickel filled and coated SWCNT sensor and the Resistive Response (Circuit) analysis unit is not within the scope of this invention. This device may be used together with other devices in an array device to detect or quantify gas mixtures comprising more than one analyte.

Sensor Device for Detection or Quantification of Hydrogen

In one embodiment, the devices of the instant invention are for detection or quantification of hydrogen mixed with a background gas. These hydrogen sensor devices comprise a sensor and an analysis unit, and the sensor comprises a carbon nanotube filled with one or more non-carbon materials, as discussed above.

However, as disclosed below in Example 15 in detail, it was found that the contribution of $R_1$ to the Resistive Response (Circuit) was less than 0.03% when the response was averaged in the hydrogen concentrations ranging from 1 to 100 ppm. Likewise, the Capacitive Response (Circuit) $C_2$, was less than 1% when this response was averaged for this concentration range. It was thereby concluded that the device comprising only one hydrogen sensor of this invention and the analysis unit that measures the Electronic Property Response $R_1$ or the Capacitive Response (Circuit) is not within the scope of this invention. This device may be used together with other devices to detect or quantify gas mixtures comprising more than one analyte.

It was also found that manganese filled and coated SWCNT sensor had a Resistive Response (Circuit) less than 0.8% at the hydrogen concentrations ranging from 1 to 100 ppm. Therefore the sensor device comprising one manganese filled and coated SWCNT sensor and the Resistive Response (Circuit) analysis unit is not within the scope of this invention. This device may be used together with other devices to detect or quantify gas mixtures comprising more than one analyte.

Sensor Device for Detection or Quantification of Carbon Dioxide

In one embodiment, the devices of the instant invention are for detection or quantification of carbon dioxide mixed with a background gas. These carbon dioxide sensor devices comprise a sensor and an analysis unit, and the sensor comprises a carbon material filled with one or more non-carbon materials, as discussed above.

However, as disclosed below in Example 18 in detail, it was found that the contribution of $R_1$ to the Resistive Response (Circuit) was less than 0.03% when the response was averaged in the carbon dioxide concentrations ranging from 1 to 100 ppm.

Likewise, the Capacitive Response (Circuit) $C_2$, was less than 1% when this response was averaged for this concentration range, except for the titanium filled and coated SWCNT sensor. It was thereby concluded that the device comprising only one carbon dioxide sensor of this invention and the analysis unit that measures the Electronic Property Response $R_1$ is not within the scope of this invention. It was further concluded that the device comprising only one carbon dioxide sensor of this invention and the analysis unit that measures the Capacitive Response (Circuit) is not within the scope of this invention, except the device comprising titanium filled SWCNT sensor. These devices may be used together with other devices to detect or quantify gas mixtures comprising more than one analyte.

It was found that the device comprising titanium filled and coated SWCNT sensor had a Capacitive Response (Circuit) higher than 1% in the carbon dioxide concentrations ranging from 1 to 100 ppm. Therefore, the device comprising the titanium filled and coated SWCNT sensor and the Capacitive Response (Circuit) analysis unit is within the scope of this invention.

Sensor Device for Detection or Quantification of Oxygen

In one embodiment, the devices of the instant invention are for detection or quantification of oxygen mixed with a background gas. These oxygen sensor devices comprise a sensor and an analysis unit, and the sensor comprises a carbon material filled with one or more non-carbon materials, as discussed above.

However, as disclosed below in Example 20 in detail, it was found that the contribution of $R_1$ to the Resistive Response (Circuit) was less than 0.03% when the response was averaged in the oxygen concentration ranging from 1 to 100 ppm. It was thereby concluded that the device comprising only one oxygen sensor of this invention and the analysis unit that measures the Electronic Property Response $R_1$ is not within the scope of this invention. This device may be used together with other devices in an array device to detect or quantify gas mixtures comprising more than one analyte.

Sensor Device for Detection or Quantification of a Gas Mixture Comprising at Least Two Analytes In one embodiment of this invention, the device is for detection or quantification of a gas mixture comprising at least two analytes. This type of device is hereafter abbreviated as "array device". The array device comprises at least two sensors and at least one analysis unit for each sensor. Each sensor and its analysis unit form a device subunit. Each subunit provides an Electronic Property Response that is different than the other. One of the sensors of the array device is a sensor comprising a carbon nanotube filled with one or more non-carbon materials as discussed above. The additional sensor or sensors comprise a carbon nanotube or a carbon nanotube filled with a non-carbon material as discussed above. Each carbon nanotube or filled nanotube is optionally coated with one or more non-carbon materials. The sensors of the array device comprise different carbon nanotubes or filled carbon nanotubes from each other.

Some of the sensors of the array device may comprise an organized assembly that yields negligible Electronic Property Responses to some analyte gases. For example, the subunit comprising nickel filled and coated SWCNT sensor and the Resistive Response (Circuit) analysis unit has negligible response to the ethanol vapor. However, this unit responds to the $NO_x$ gases. Therefore, in a gas mixture comprising an $NO_x$ gas and ethanol gas, the array device comprising this subunit may detect or quantify the $NO_x$ gas.

Some of the sensors of the array device may comprise a carbon nanotube. As explained above, such sensors may have very low or negligible electronic responses to some analyte gases as compared to most of the sensors comprising the organized assemblies of this invention. However, the negligible response can be utilized in a sensor array, for example, as a reference sensor.

The invention is illustrated further by the following further examples that are not to be construed as limiting the invention in scope to the specific procedures or products described in them.

EXAMPLES

Example 1

Ti Filled SWCNT Article

In this example, the single-wall carbon nanotubes (SWCNTs) were filled with titanium (Ti). This experiment was conducted with minimal exposure to the external environment. SWCNTs were purchased from Carbon Solutions Inc. (Riverside, Calif.) with a catalog number P2-SWNT. They are manufactured by using the arc process and have external diameters varying in the range of 1 nanometer and 1.8 nanometers. These SWCNTs are designated as "starting SWCNT."

The starting SWCNTs were processed as follows. The SWCNTs, weighed about 82 mg, were placed in a 50 ml three-necked round bottom Pyrex flask, which was equipped with a heating mantle, a thermocouple, and an addition arm. The flask was connected to a vacuum system through a liquid nitrogen trap.

The titanium iodide crystals ($TiI_4$) used in this Example were purchased from Aldrich with a catalog number 41, 359-3. The iodine crystals ($I_2$) were purchased from Aldrich with a catalog number 20, 777-2. $TiI_4$ (about 1.8 gram) was mixed with $I_2$ (about 1.8 gram) in a nitrogen-filled glove box and placed in the flask addition arm. The end of the addition arm was covered to protect the mixture from atmospheric moisture. The addition arm was then taken out of the glove box and connected to the reaction flask. Thus, the SWCNTs and the $TiI_4/I_2$ mixture initially were kept in separate locations in the flask.

After the connection, the flask was immediately evacuated to a pressure below 1 Torr. The contents of the flask were then heated to about 150° C. in vacuum for about 15 minutes to remove volatile species from the SWCNTs. After this heating, the vacuum valve was closed and the $TiI_4/I_2$ mixture was poured on the SWCNTs by tipping the addition arm. The heating was continued in order to melt the $TiI_4/I_2$ mixture and soak the SWCNTs in the melt as follows. First, after the mixture was poured, the flask was heated to about 200° C. within about 6 minutes. Then, it was further heated to about 275° C. within about 12 minutes. Upon reaching about 275° C., the vacuum valve was opened to remove some un-reacted $TiI_4/I_2$ by evaporation into the cold trap. The heating was continued in vacuum at about 275° C. for about 1 hour. The contents of the flask were then cooled to room temperature by cutting power to the heating mantle. At this step, the nanorods comprised $TiI_4/I_2$ coated and filled SWCNTs.

This article was processed to remove $TiI_4$ and $I_2$ coating by an ethanol washing step as follows.

After the cooling, the flask was transferred to the glove box filled with nitrogen, and the article was washed with ethanol (Aldrich, catalog number 45, 984-4) to further remove un-reacted $TiI_4/I_2$ mixture. The nanorods were first mixed with about 25 ml ethanol to prepare a suspension. This suspension was then centrifuged at a centrifugal force of about 10,000 g for about 15 minutes to obtain a supernatant phase and a precipitate phase. The supernatant phase was carefully removed by using a pipette and discarded. This washing step was repeated once. The precipitate phase was then transferred back to the glove box and it was dried at about 25° C. to remove residual ethanol. The precipitate phase was characterized by 633 nm Raman spectroscopy. In the ethanol washing step, the centrifugation step may be replaced with a filtration step to recover the nanorods from the suspension. At this step, the nanorods comprised $TiI_4/I_2$ filled SWCNTs.

The $TiI_4/I_2$ filled SWCNTs were processed to remove iodine by a heat treatment step as follows.

The precipitate phase was then placed in a quartz tube, which was inserted in a tube furnace. The tube was sealed, connected to a vacuum system and evacuated to about 30 mTorr pressure. The furnace was then heated to about 500° C. within one hour. The heating was continued at about 500° C. for about 30 minutes.

After this heating period, a gas mixture consisting essentially of about 3% hydrogen and about 97% argon was introduced into the quartz tube and the pressure was raised to about 10 Torr. The heating was further continued at a furnace temperature of about 500° C. for about two hours at about 10 Torr in the flowing gas mixture, after which the furnace was cooled to room temperature. The Ti filled SWCNTs were thereby obtained.

Example 2

Ti Filled and Coated SWCNT Article

In this example, the SWCNTs were both filled and coated with titanium (Ti). This example was carried out in the same manner as described in Example 1, except that the contents of the reaction flask were heated at about 275° C. for about 15 to 20 minutes prior to opening the vacuum valve and that the ethanol washing step was not carried out after the preparation of the article comprising $TiI_4/I_2$ coated and filled SWCNTs. Thus, after the cooling of the flask, $TiI_4/I_2$ coated and filled SWCNTs were directly placed in a quartz tube, which was inserted in a tube furnace. The Ti filled and coated SWCNTs were thereby obtained.

Example 3

TiH$_w$ Filled SWCNT Article

In this example, TiH$_w$ filled SWCNTs were prepared, where w varies in the range of 0 to 2. First, Ti filled SWCNTs were prepared in the same manner as described in Example 1. Then, these nanorods were placed in an air-free chamber and heated to about 650° C. in vacuum for at least 2 hours to remove volatile compounds. After the removal of volatile compounds, the temperature was decreased to about 500° C. and the chamber was pressurized to about 500 Torr with hydrogen. The nanorods were hydrogenated by keeping them at this temperature for at least one hour. Finally, the hydrogenated nanorods were cooled to a room temperature. TiH$_w$ filled SWCNT articles were thereby prepared.

These nanorods were later heated to a temperature in the range of 400° C. to 650° C. to release the hydrogen from the nanorods. The hydrogen evolution was followed by using a mass spectrometer. The evolution started at about 200° C. and became considerable at about 400° C. The total amount of hydrogen evolved from the nanorods indicated that at least 80% TiH$_{0.800}$. This result demonstrated that Ti filled SWCNTs may be used in preparation of hydrogen storage devices and the hydrogen evolution may be achieved at temperatures as low as 200° C.

Example 4

Ni Filled and Coated SWCNT Article

This Example was carried out in the same manner as described in Example 1, except that 0.9 gram of nickel iodide and 1.1 grams of iodine were used instead of about 1.8 grams of TiI$_4$ and about 1.8 grams of I$_2$, that the annealing was carried out at about 500° C. for about 30 minutes, followed by about 600° C. for about 2 hours instead of about 500° C. for about 2 hours, and that during the cooling, a gas mixture consisting essentially of about 50 percent nitrogen, about 2.5 percent hydrogen and about 47.5 percent argon was flowed at a pressure of about 20 Torr, instead of the gas mixture consisting essentially of about 5 percent hydrogen and about 95 percent argon at a pressure of about 10 Torr. The article comprising Ni filled and coated SWCNTs was thereby prepared.

Example 5

Fe Filled and Coated SWCNT Article

This Example was carried out in the same manner as described in Example 1, except that about 0.9 gram of ferric iodide and about 1.8 grams of iodine were used instead of about 1.8 grams of TiI$_4$ and about 1.8 grams of I$_2$, that the annealing was carried out at about 500° C. for about 30 minutes, followed by about 600° C. for about 2 hours instead of about 500° C. for about 2 hours, and that during the cooling, a gas mixture consisting essentially of about 50 percent nitrogen, about 2.5 percent hydrogen and about 47.5 percent argon was flowed at a pressure of about 20 Torr, instead of the gas mixture consisting essentially of about 5 percent hydrogen and about 95 percent argon at a pressure of about 10 Torr. The article comprising Fe filled and coated SWCNTs was thereby prepared.

Examples 6 to 9

Metal Filled and Coated SWCNT Articles

In these examples, the starting SWCNTs were filled with various metals in the same manner as described in Example 5, except that iodides of Mn, Co, Pd or Pt were used instead of ferric iodide. The articles comprising Mn filled and coated SWCNTs, Co filled and coated SWCNTs, Pd filled and coated SWCNTs, or Pt filled and coated SWCNTs were thereby prepared.

Example 10

Preparation of a Sensor Comprising Ti Filled SWCNT Article

Figure 2:
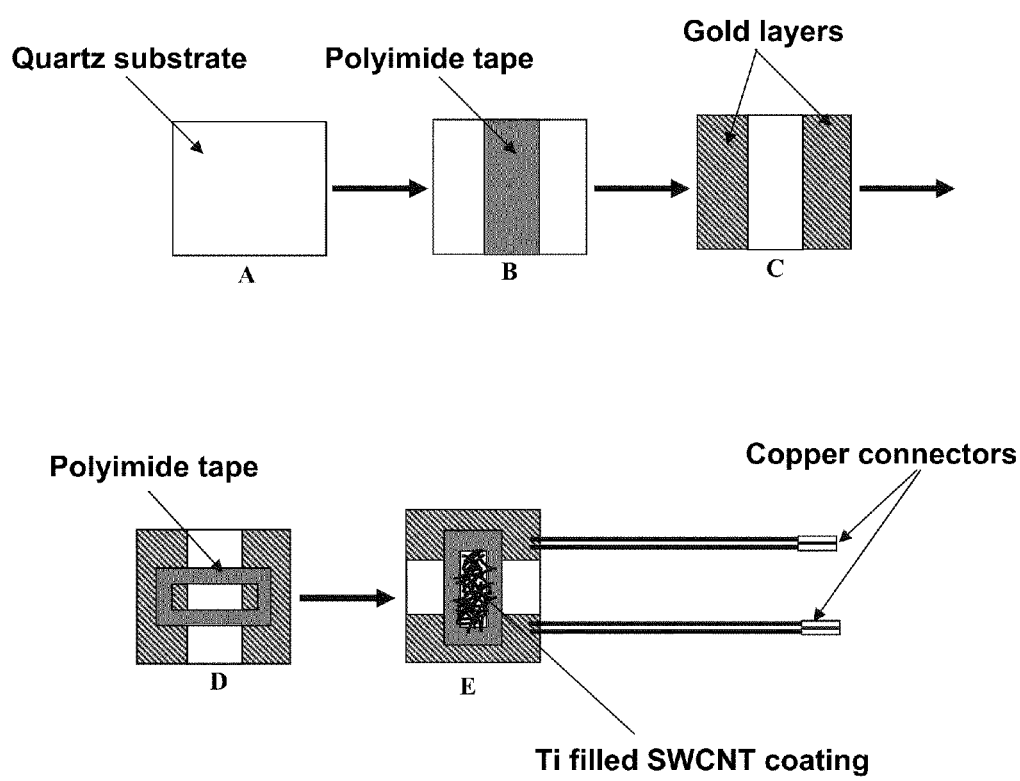
FIG. 2 schematically shows the preparation of a gas sensor comprising organized carbon and non-carbon assembly.

Preparation of a gas sensor is shown in FIG. 2. First, a quartz slide with a thickness of about 1.0 mm (Ted Pella, Inc. Prod. #26011) was cut into an about 1 cm× about 1 cm square substrate (FIG. 2A). These substrates were cleaned in two steps as follows. In a first cleaning step, the substrates were placed in a 4 to 5 weight percent detergent/water solution and sonicated for about 5 minutes. These substrates were then washed with deionized water for at least one minute and finally dried by blowing dry nitrogen gas. In a second cleaning step, a solution was prepared to contain deionized water, hydrogen peroxide and ammonium hydroxide with a volume ratio of about 5:1:1 respectively. The quartz substrates cleaned in the first step were placed in this solution and heated at about 80° C. for at least 20 minutes. These substrates were then washed with deionized water for at least one minute and finally dried by blowing dry nitrogen gas. About 2 mm×about 1 cm strip of polyimide tape was then placed at the center of the cleaned quartz substrate to function as a mask for subsequent evaporation and sputtering of chromium and gold respectively onto the top surface of the quartz substrates (FIG. 2B). The masked quartz substrate was then placed inside a sputter coater (Denton Vacuum DV-502A). A chromium layer of average thickness less than about 100 Å was first deposited on this substrate to act as an adhesion layer (not shown in FIG. 2). Then, a gold layer with an average thickness of about 2000 Å was deposited on this chromium layer and the mask was removed (FIG. 2C). The gold-deposited quartz substrate was then covered with a strip of polyimide tape, cut to provide a window of dimension about 4 mm× about 2 mm and placed onto the substrate so as to bridge the sputtered gold areas (FIG. 2D). Two pairs of shielded copper wire, each piece terminating in gold pins, were soldered onto each gold deposited area (FIG. 2E) to allow for four-point impedance measurement over the quartz surface.

The titanium filled SWCNT article prepared in Example 1 (about 1 mg) was mixed with about 5.0 milliliter of anhydrous dimethylformamide (DMF, Acros Cat. #61032-0010). This mixture was then sonicated using a horn sonicator (Sonics Materials, Model VC600) at about 600 W power and about 20 MHz frequency for about 5 minutes. This sonication step was repeated three times. A dispersion of the titanium filled SWCNT article was thereby obtained.

This dispersion was deposited drop by drop on the open area of the polyimide tape by using a syringe (3 mL capacity) equipped with a blunted needle (18G). This deposition was continued until all the open area was covered with a dispersion layer. The dispersant was first allowed to slowly evaporate from the dispersion layer by forced air flow at room temperature. Then, the quartz substrate was placed in a forced air convection oven at about 130° C. for about 30 minutes for further removal of the dispersant. After this drying, a coating of the titanium filled SWCNT article connecting the two gold layers was formed and a gas sensor was thereby prepared. This sensor is hereafter designated as the Ti$^f$-SWCNT sensor, where superscript "f" refers "filled".

Another sensor was prepared in the same manner described in this example, except that the starting SWCNTs purchased from Carbon Solutions Inc. with a catalog number P2-SWNT were used instead of the Ti filled SWCNT article. This sensor is hereafter designated as the Starting SWCNT sensor.

Example 11

Sensor Comprising Ti Filled SWCNT Article for Detection or Quantification of $NO_2$ Gas The variation of electrical properties of sensors prepared in Example 10 was analyzed as follows. First, the electrical connection between the two gold layers was tested by using a multimeter (Fluke Model 189) and measuring the resulting finite contact resistance. After it was ensured by this measurement that the electrical connection between the gold layers was formed by the coating of the titanium filled SWCNT article, the sensor was assembled into a gas chamber and connected to an impedance analyzer (Novocontrol Technologies Model Alpha A). The impedance analyzer was the analysis unit. The electrical connection was done through a 15-pin sub D type connector (MDC Inc. Part#D15-K200) mounted on an NW50 KF flange (MDC, Inc.) for use as the top plate assembly of the gas chamber. The D type connector allowed electrical connection between the impedance analyzer test interface and the sensor, while supporting the wired sensor inside the vacuum (test) side of the chamber.

As a pre-conditioning step, before the impedance measurement was carried out, the chamber was first evacuated to a pressure below 1 Torr at room temperature and kept at this pressure for about 4 hours by using a vacuum pump.

An interrogating sinusoidal voltage of about 50 mV. (about 70 mV$_{peak-to-peak}$) was applied to the sensor by varying the frequency in the range of 10 MHz to 10 mHz. Gas sensing experiments were carried out in the following sequence. For impedance measurements of the sensor in vacuum, all valves were closed to the atmosphere and the chamber was evacuated below 1 Torr pressure by using the vacuum pump. Then, the pump was switched off. After it was ensured that the pressure did not increase above 1 Torr within a predetermined period of time, the impedance measurements were started. For impedance measurements in air, the ultra-high purity (UHP) air line was opened and the chamber was filled with air until the pressure in the chamber reached about 760 Torr. Then a release valve was opened to an ambient atmosphere to allow a flow of the UHP air into the chamber, regulated at about 100 milliliter per minute by means of a mass flow controller. For impedance measurements in nitrogen, the release valve was closed and the chamber was evacuated to a pressure below 1 Torr. The UHP $N_2$ line was then opened and the chamber was filled with nitrogen until a pressure of about 760 Torr was reached and the release valve opened to an ambient atmosphere. The flow of UHP nitrogen into the chamber was regulated at about 100 milliliter per minute by means of a mass flow controller.

For sensor impedance measurements in a test gas such as $NO_2$, the parent $NO_2$ gas (about 1000 ppm in nitrogen) was diluted with the ultra-high purity $N_2$ to yield concentrations of $NO_2$ varying in the range of 0 ppm to 250 ppm. The flow rate of the diluted test gas was controlled at about 100 milliliter per minute by means of an MKS multi-gas controller (Model 647C). Each concentration of $NO_2$ gas mixture was allowed to flow over the assembled sensor for about 10 minutes prior to acquiring the frequency dependent impedance values.

Figure 4:
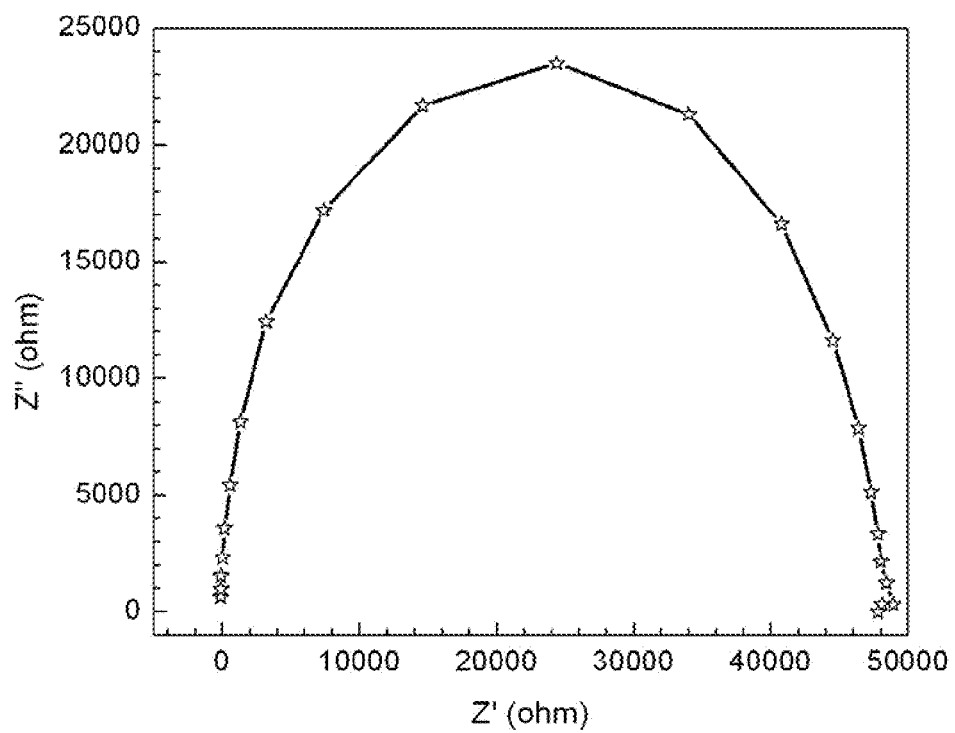
FIG. 4 shows the Nyquist plot for the $Ti^f$-SWCNT sensor responding to 10 ppm $NO_2$ gas at room temperature.
Figure 5:
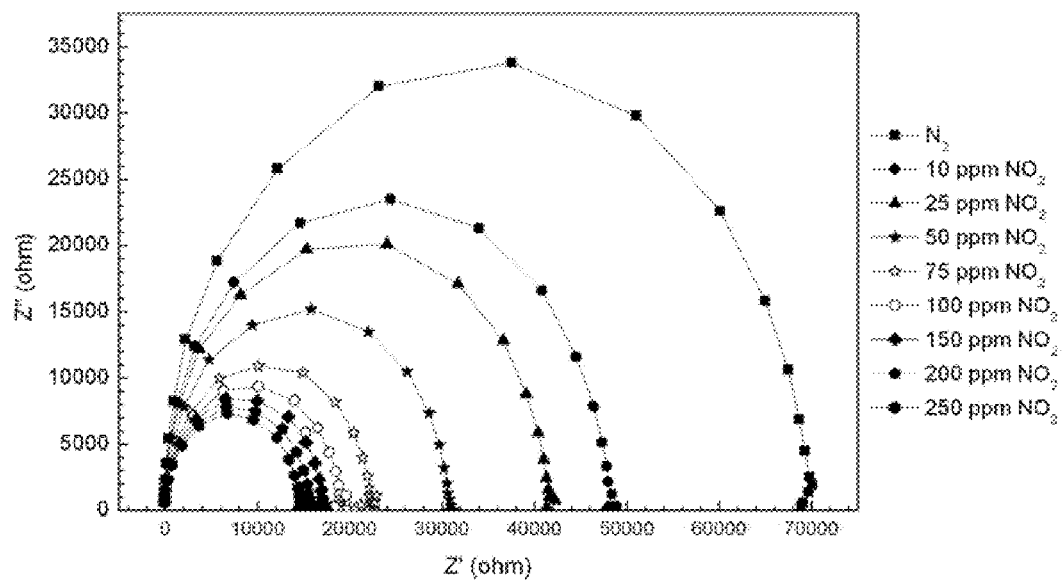
FIG. 5 shows the Nyquist plots of the $Ti^f$-SWCNT sensor as a function of $NO_2$ gas concentration.

The total impedance (Z) was resolved into a real part (Z') and an imaginary part (Z") and a semicircular Nyquist plot was obtained, which intersected the Z' axis at two points. The difference between these two intersection points yielded the real part of the resistance. For example, as shown in FIG. 4, the real resistance was about 48,900 ohms for the Ti$^f$-SWCNT sensor at about 10 ppm $NO_2$ concentration. Same measurements were repeated at various $NO_2$ concentrations to determine the sensor response as a function of the gas concentration. The same measurement was also repeated for UHP $N_2$ to determine the response of the sensor to the diluent (i.e. background) gas. The measurement results are shown in FIG. 5.

Figure 6:
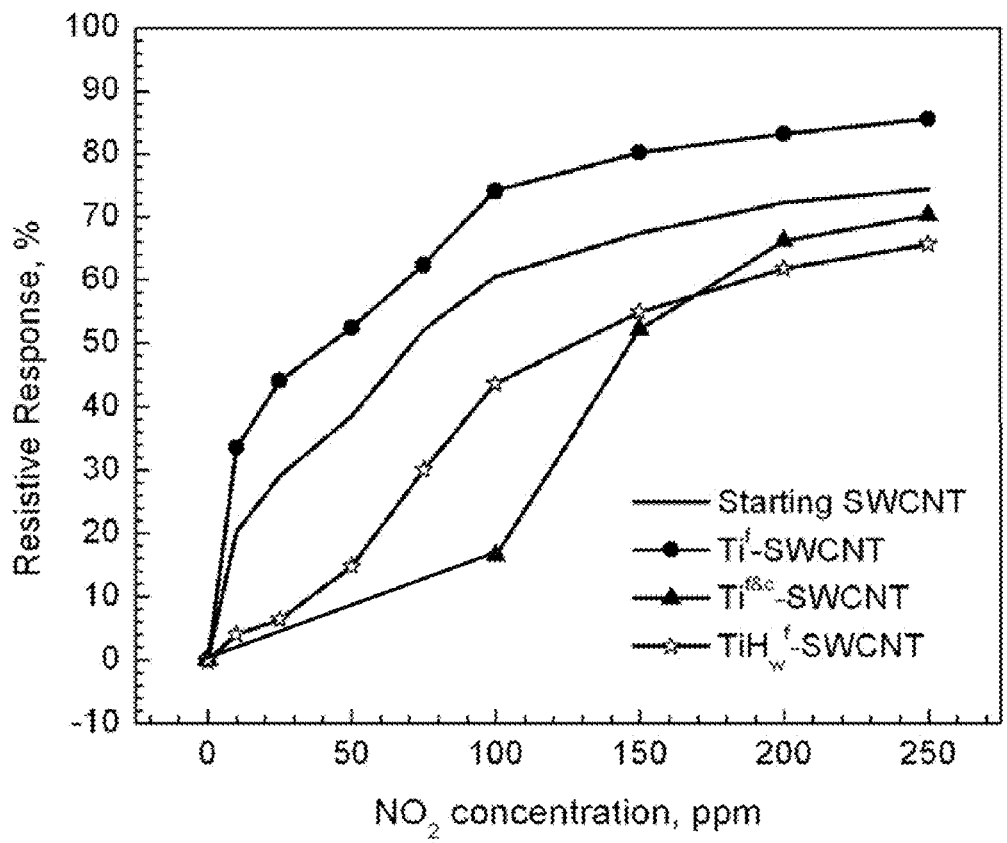
FIG. 6 shows the Resistive Response of the $Ti^f$-SWCNT, $Ti^{f\&c}$-SWCNT, $TiH_w^f$-SWCNT and the Starting SWCNT sensor as a function of $NO_2$ gas concentration.
Figure 7:
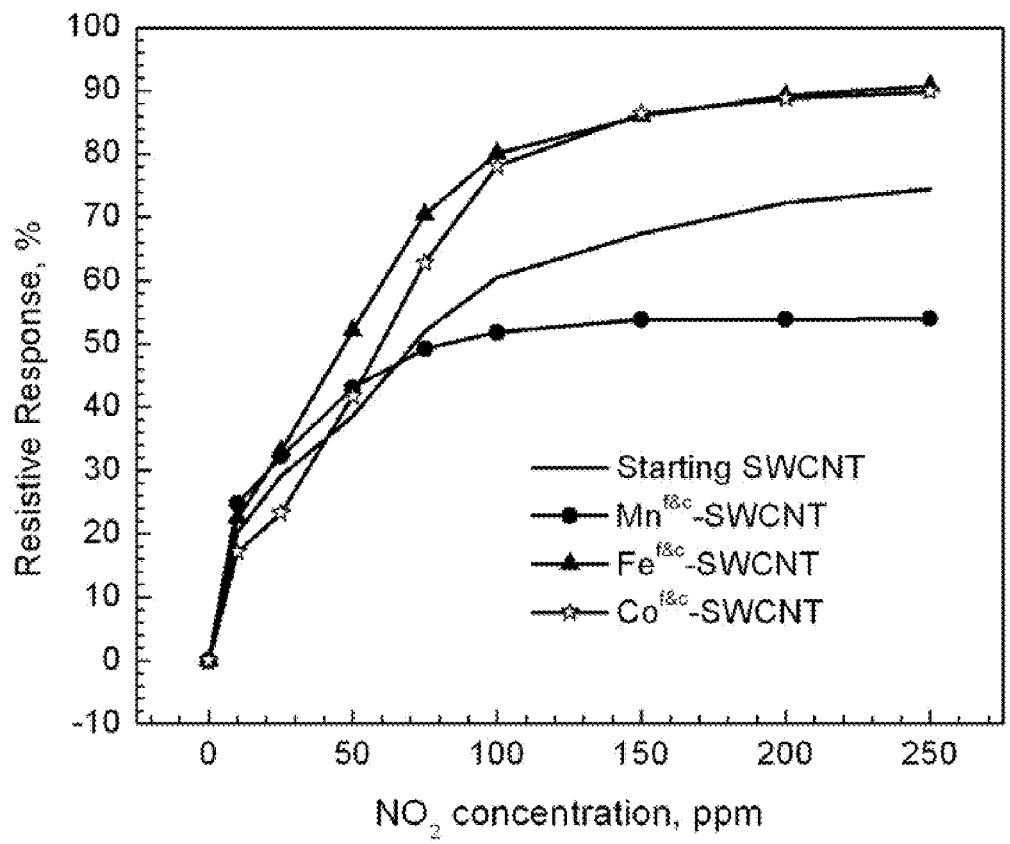
FIG. 7 shows the Resistive Response of the $Mn^{f\&c}$-SWCNT, $Fe^{f\&c}$-SWCNT, $Co^{f\&c}$-SWCNT and Starting SWCNT sensors as a function of $NO_2$ gas concentration.
Figure 8:
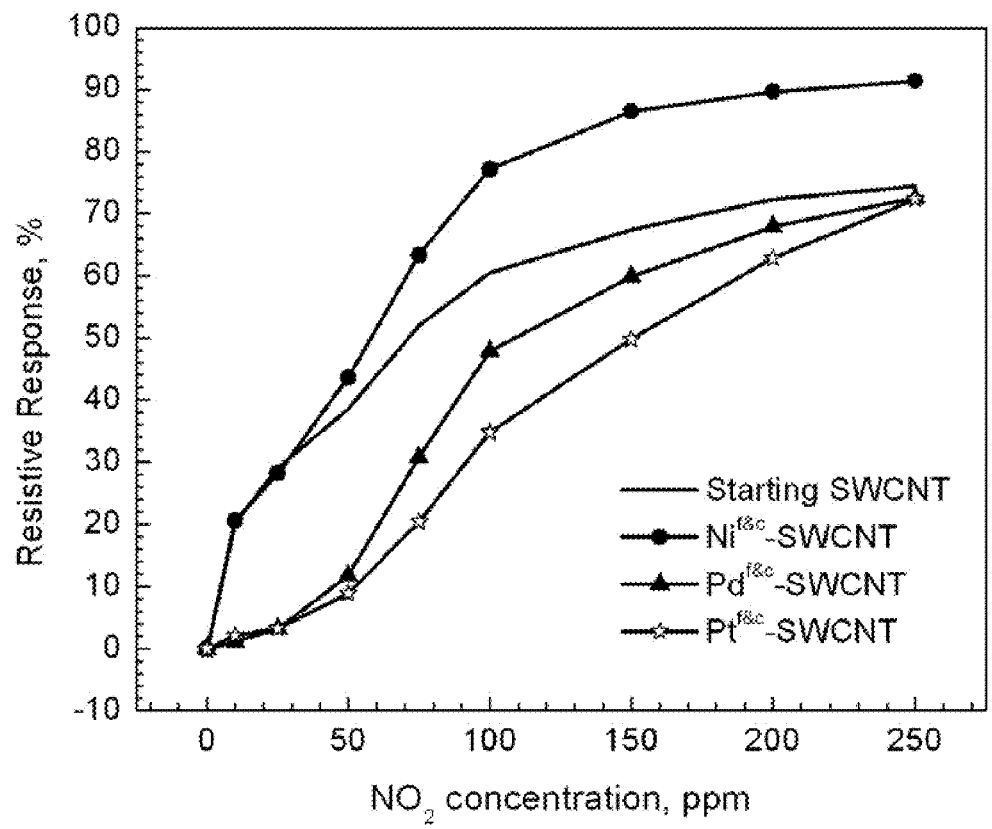
FIG. 8 shows the Resistive Response of the $Ni^{f\&c}$-SWCNT, $Pd^{f\&c}$-SWCNT, $Pt^{f\&c}$-SWCNT and Starting SWCNT sensors as a function of $NO_2$ gas concentration.

The normalized resistive response of the sensor was calculated by using the following formula:

$$\text{Resistive Response}(\%) = 100 \times (R_{N2} - R_{mix})/R_{N2}$$

where $R_{N2}$ and $R_{mix}$ are the real resistances of the sensor in nitrogen (i.e. background gas) and the $NO_2$—$N_2$ gas mixture respectively. The variation of the Resistive Response of the sensor as a function of $NO_2$ gas concentration is shown in FIG. 6. Same impedance measurements were repeated for the Starting SWCNT sensor. As shown in FIG. 6, the normalized resistive response of the Ti$^f$-SWCNT sensor was higher than that of the Starting SWCNT sensor for all $NO_2$ concentrations.

This sensor was further analyzed by modeling the impedance data in the Nyquist plot using an equivalent circuit method. This model electrical circuit, shown in FIG. 3, is formed by a resistor $R_1$, another resistor $R_2$, and a non-Debye capacitor $C_2$. The values of $R_1$, $R_2$ and $C_2$ for each sensor in response to each gas concentration were obtained by fitting the Nyquist plot to the model electrical circuit by using an electrochemical impedance spectroscopy measurement software manufactured by Scribner Associates (Southern Pines, N.C.).

It was found that $R_1$, the uncompensated ohmic resistance of the sensor did not show any dependence to the $NO_2$ concentration. That is, the contribution of $R_1$ to the Resistive Response (Circuit) was less than 0.03% when the Resistive Response was averaged in the $NO_2$ concentrations ranging from 1 to 100 ppm. It was thereby concluded that the Electronic Property Response $R_1$ is not suitable for detection or quantification of $NO_2$ with Ti$^f$-SWCNT sensor.

The other circuit parameters $R_2$ and $C_2$ decreased in the presence of $NO_2$. Same impedance measurements were repeated for the Starting SWCNT sensor.

Figure 9:
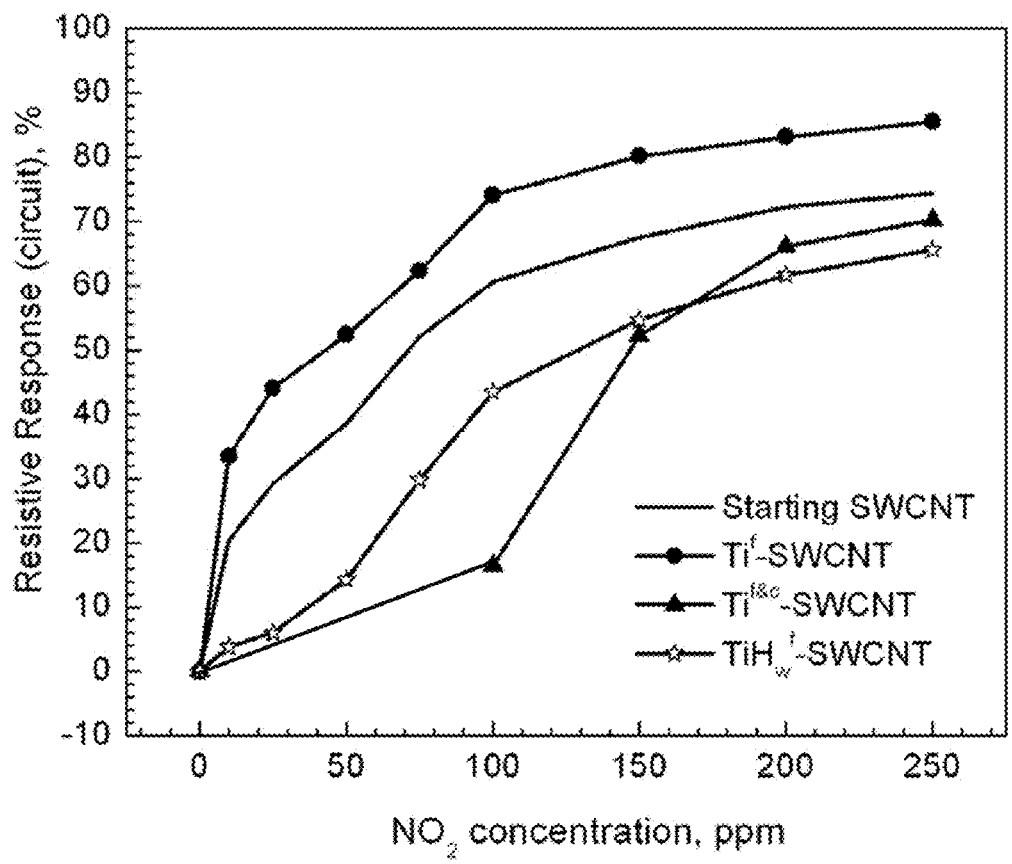
FIG. 9 shows the Resistive Response (Circuit) of the $Ti^f$-SWCNT, $Ti^{f\&c}$-SWCNT, $TiH_w^{f\&c}$-SWCNT and the Starting SWCNT sensor as a function of $NO_2$ gas concentration.
Figure 10:
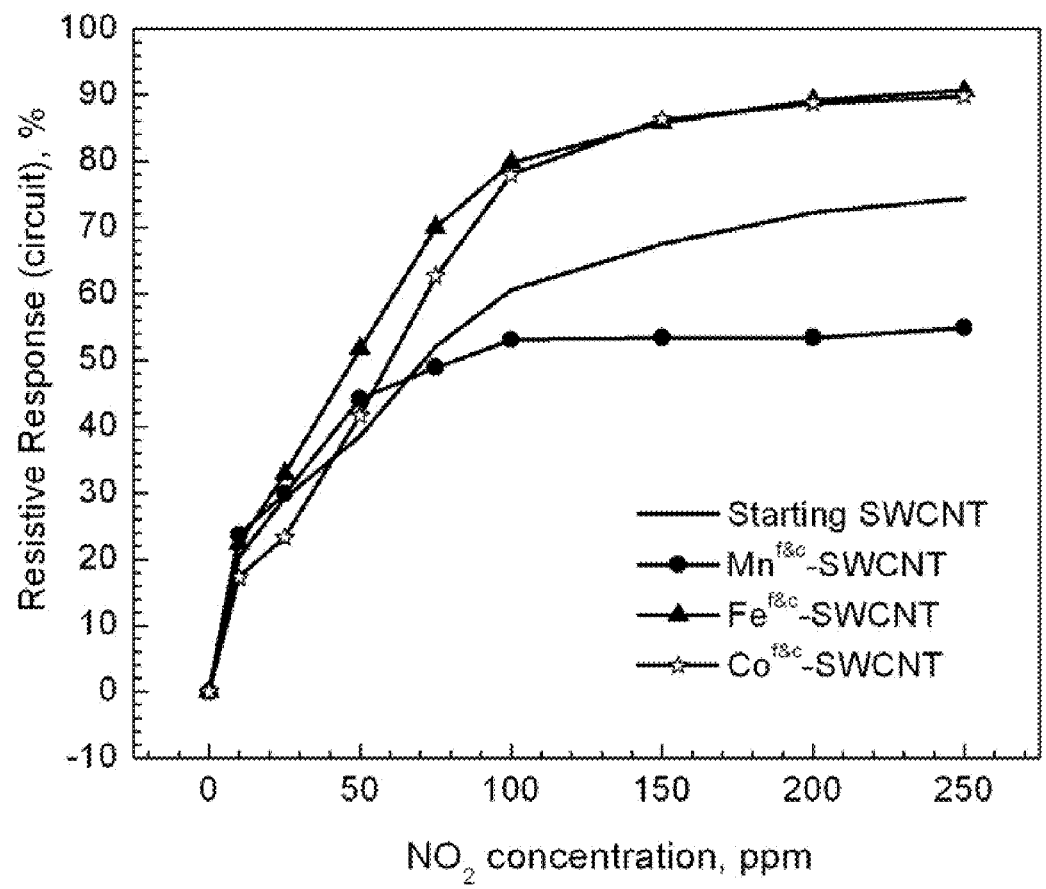
FIG. 10 shows the Resistive Response (Circuit) of the $Mn^{f\&c}$-SWCNT, $Fe^{f\&c}$-SWCNT, $Co^{f\&c}$-SWCNT and Starting SWCNT sensors as a function of $NO_2$ gas concentration.
Figure 11:
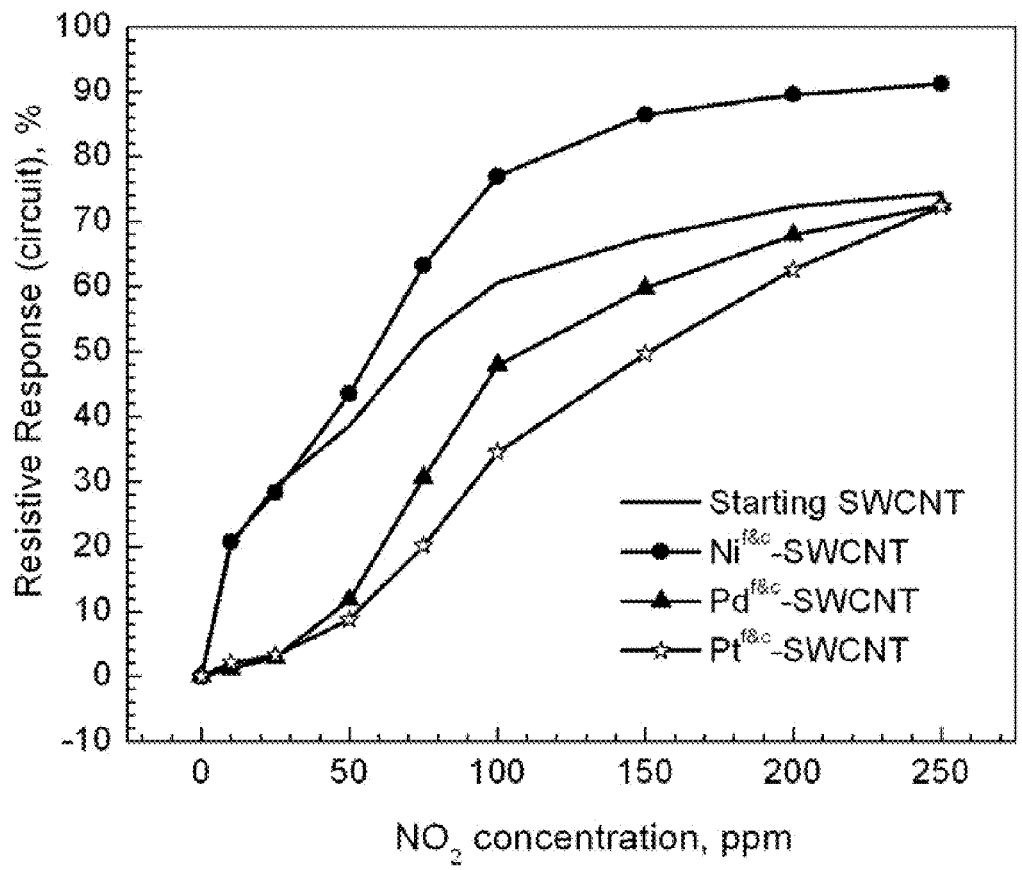
FIG. 11 shows the Resistive Response (Circuit) of the $Ni^{f\&c}$-SWCNT, $Pd^{f\&c}$-SWCNT, $Pt^{f\&c}$-SWCNT and Starting SWCNT sensors as a function of $NO_2$ gas concentration.

The normalized resistive and normalized capacitive responses of the sensor were calculated by using the formula:

$$\text{Resistive Response(Circuit)}(\%) = 100 \times (R'_{N2} - R'_{mix})/R'_{N2}$$

where $R'_{N2}$ and $R'_{mix}$ individually equal to the sum of their $R_1$ and $R_2$ components derived by using the model electrical circuit. As shown in FIG. 9, the Resistive Response (Circuit) of the Ti$^f$-SWCNT sensor was higher than that of the Starting SWCNT sensor for all $NO_2$ concentrations.

Figure 12:
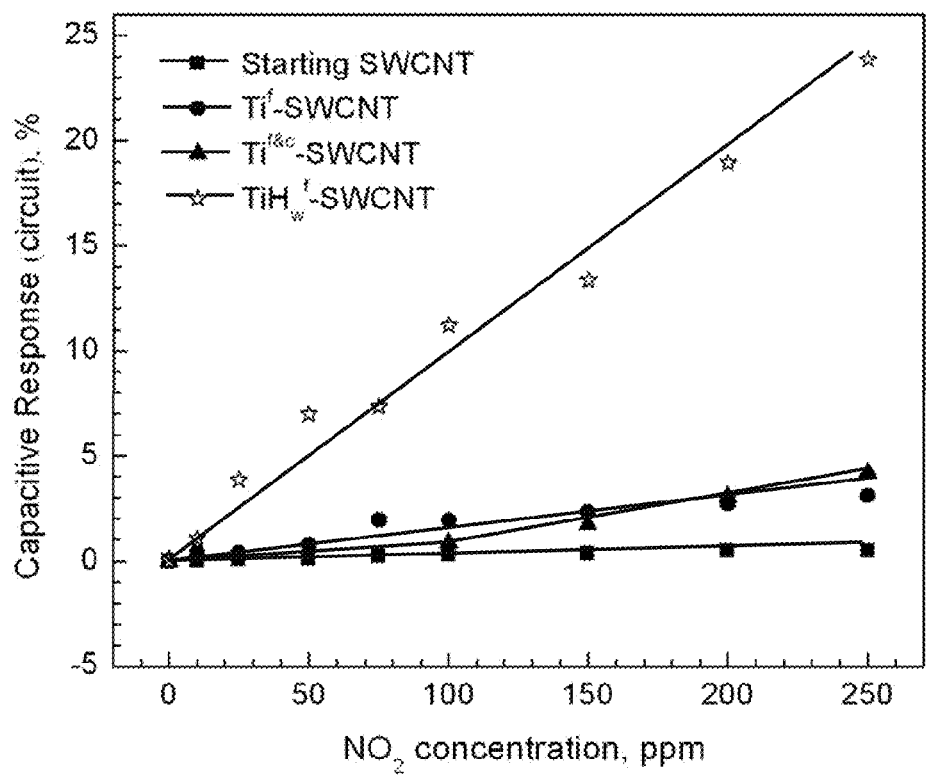
FIG. 12 shows the Capacitive Response (Circuit) of the $Ti^f$-SWCNT, $Ti^{f\&c}$-SWCNT, $TiH_w^f$-SWCNT and the Starting SWCNT sensor as a function of $NO_2$ gas concentration.

Likewise, the normalized capacitive response of the sensor was calculated by using the formula:

$$\text{Capacitive Response(Circuit)}(\%) = 100 \times (C_{2,N2} - C_{2,mix})/C_{2,N2}$$

where $C_{2,N2}$ and $C_{2,mix}$ are the capacitance of the sensor in nitrogen and the $NO_2$—$N_2$ gas mixture respectively, which is derived by using the model electrical circuit. As shown in FIG. 12, the Capacitive Response (Circuit) of the $Ti^f$-SWCNT sensor was higher than that of the Starting SWCNT sensor for all $NO_2$ concentrations.

All these results disclosed above indicated that the incorporation of non-carbon material into the carbon nanotubes improved the response of the sensor.

Example 12

Sensors for Detection and Quantification of $NO_2$ Gas

Various sensors were prepared and analyzed in the same manner as described in Example 11, except that the SWCNT articles prepared in Examples 2 to 9 were used instead of the Ti filled SWCNT article prepared in Example 1. The results are shown in FIGS. 6 to 16. If a sensor is prepared by using a non-carbon filled and coated SWCNT article, it is designated, for example, as $Fe^{f\&c}$-SWCNT sensor, where "f&c" refers "filled and coated".

It was found that $R_1$, the uncompensated ohmic resistance of these sensors did not show any dependence to the $NO_2$ concentration. That is, the contribution of $R_1$ to the Resistive Response (Circuit) was less than 0.03% when the response was averaged in the $NO_2$ concentration range of 1 ppm to 100 ppm. It was thereby concluded that the Electronic Property Response, $R_1$ is not suitable for detection or quantification of $NO_2$ with these sensors.

As shown in FIGS. 6 and 9, the Resistive Response and Resistive Response (Circuit) of the $Ti^f$-SWCNT sensor was higher than those of the $Ti^{f\&c}$-SWCNT sensor and $TiH_w^f$-SWCNT sensor as well as that of the Starting SWCNT sensor for $NO_2$ concentration in the range of 0 ppm to 250 ppm. Also, the Resistive Response and Resistive Response (Circuit) of the Starting SWCNT sensor were higher than those of the $Ti^{f\&c}$-SWCNT sensor and the $TiH_w^f$-SWCNT sensor.

These results indicated that the $Ti^f$-SWCNT sensor, $Ti^{f\&c}$-SWCNT sensor or $TiH_w^f$-SWCNT sensor together with the Resistive Response analysis unit or Resistive Response (Circuit) analysis unit can detect and quantify $NO_x$ gases. They are thereby within the scope of one preferred embodiment of this invention. In another preferred embodiment, the sensor devices comprising a $Ti^f$-SWCNT sensor and a Resistive Response analysis unit or Resistive Response (Circuit) analysis unit are used to detect or quantify $NO_x$ gases.

Figure 13:
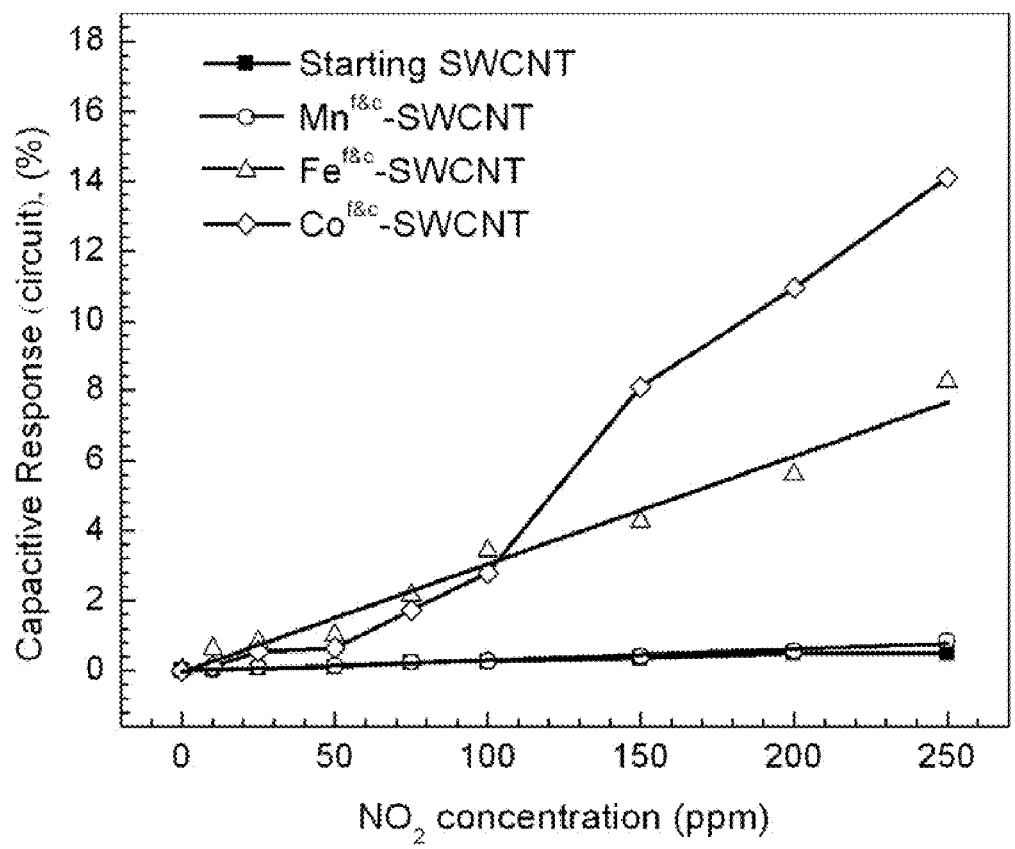
FIG. 13 shows the Capacitive Response (Circuit) of the $Mn^{f\&c}$-SWCNT, $Fe^{f\&c}$-SWCNT, $Co^{f\&c}$-SWCNT and Starting SWCNT sensors as a function of $NO_2$ gas concentration.
Figure 14:
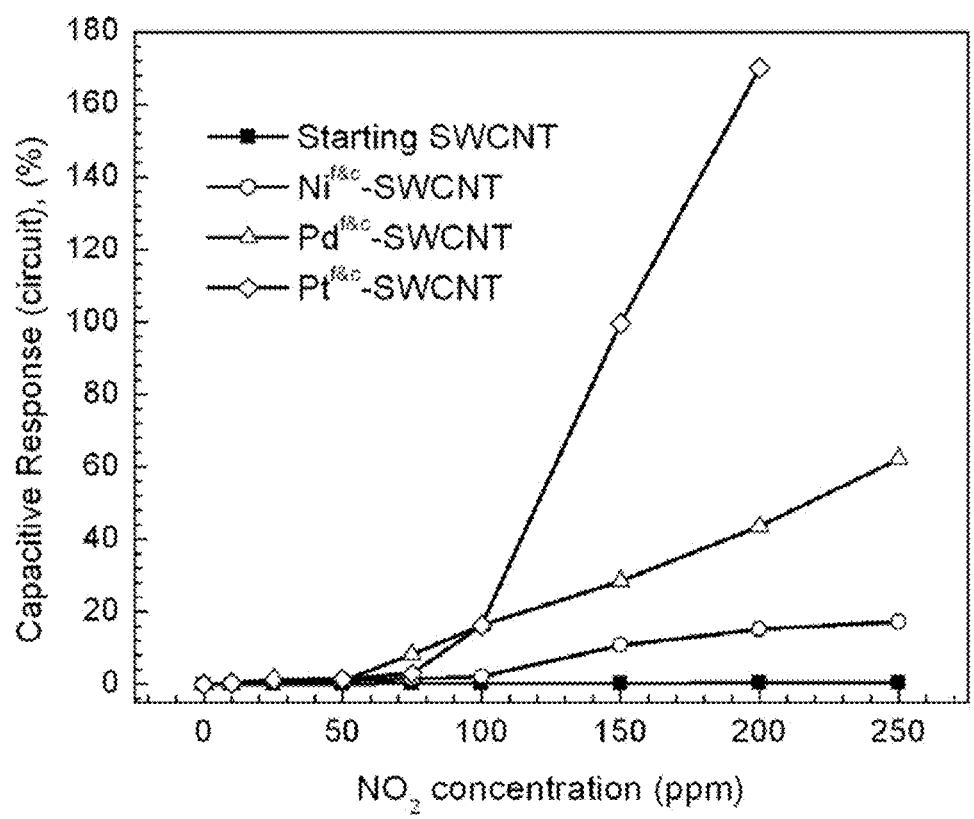
FIG. 14 shows the Capacitive Response (Circuit) of the $Ni^{f\&c}$-SWCNT, $Pd^{f\&c}$-SWCNT, $Pt^{f\&c}$-SWCNT and Starting SWCNT sensors as a function of $NO_2$ gas concentration.

The variation of the Capacitive Response (Circuit) of the sensors as a function of $NO_2$ gas concentration is shown in FIGS. 12 to 14. As shown in FIG. 12, the slope of the $TiH_w^f$-SWCNT sensor increased as compared to the $Ti^f$-SWCNT sensor and the $Ti^{f\&c}$-SWCNT sensor, indicating that it had a better Capacitive Response (Circuit). This result further indicated that the sensors comprising hydrides of non-carbon materials such as hydrides of Zr, Hf, V, Cr, Mn, Fe, Co, Ni, Pd, Pt, or mixtures of such non-carbon materials may have improved Capacitive Responses (circuit) as compared to those sensors comprising non-hydride non-carbon materials.

As shown in FIGS. 7, 8, 10 and 11, the Resistive Responses and the Resistive Responses (Circuit) of the $Fe^{f\&c}$-SWCNT, $Co^{f\&c}$-SWCNT and $Ni^{f\&c}$-SWCNT sensors were higher than that of the Starting SWCNT sensor, particularly for $NO_2$ concentrations higher than 50 ppm. $Mn^{f\&c}$-SWCNT sensor showed higher Resistive Response and Resistive Response (Circuit) as compared to the Starting SWCNT sensor for $NO_2$ concentrations at about 50 ppm or below. $Pd^{f\&c}$-SWCNT and $Pt^{f\&c}$-SWCNT sensors showed lower Resistive Response and Resistive Responses (Circuit) as compared to the Starting SWCNT sensor.

These results indicated that the $Fe^{f\&c}$-SWCNT, $Co^{f\&c}$-SWCNT, $Ni^{f\&c}$-SWCNT, $Mn^{f\&c}$-SWCNT, $Pd^{f\&c}$-SWCNT or $Pt^{f\&c}$-SWCNT sensor together with the Resistive Response analysis unit or Resistive Response (Circuit) analysis unit can detect and quantify $NO_x$ gases. They are thereby within the scope of one preferred embodiment of this invention. In another preferred embodiment, the sensor devices comprising $Fe^{f\&c}$-SWCNT sensor, $Co^{f\&c}$-SWCNT sensor or $Ni^{f\&c}$-SWCNT sensors and the Resistive Response analysis unit or Resistive Response (Circuit) analysis unit are used to detect or quantify $NO_x$ gases.

As shown in FIGS. 13 and 14, the $Fe^{f\&c}$-SWCNT sensor, the $Co^{f\&c}$-SWCNT sensor, the $Ni^{f\&c}$-SWCNT sensor, the $Pd^{f\&c}$-SWCNT sensor and the $Pt^{f\&c}$-SWCNT sensor had an increased Capacitive Response (circuit) to varying $NO_2$ concentration, whereas the response of the Starting SWCNT sensor and the $Mn^{f\&c}$-SWCNT sensor was very low. Furthermore, the slope (i.e. sensitivity) for some of these sensors considerably increased above a threshold $NO_2$ concentration, indicating that these sensors may be used for selective identification of $NO_x$ gases in gas mixtures as well as determination of their concentration. This threshold value varied with the sensor type. For example, the $Co^{f\&c}$-SWCNT sensor showed considerably increased response above about 50 ppm $NO_2$, the $Ni^{f\&c}$-SWCNT sensor above about 100 ppm $NO_2$, the $Pd^{f\&c}$-SWCNT sensor above about 50 ppm $NO_2$ and the $Pt^{f\&c}$-SWCNT sensor above about 75 ppm $NO_2$.

These results indicated that the $Fe^{f\&c}$-SWCNT, $Co^{f\&c}$-SWCNT, $Ni^{f\&c}$-SWCNT, $Pd^{f\&c}$-SWCNT or $Pt^{f\&c}$-SWCNT sensor together with the Capacitive Response (Circuit) analysis unit can detect and quantify $NO_x$ gases. They are thereby within the scope of one preferred embodiment of this invention.

The Capacitive Response (Circuit) of the Starting SWCNT was very low, less than 0.26% at the $NO_2$ concentrations ranging from 1 to 100 ppm. This result indicated that a sensor device comprising only one Starting SWCNT sensor and a Capacitive Response (Circuit) analysis unit cannot be used for detection or quantification of $NO_x$ gases. However, this sensor can be used together with other sensors in a device comprising a sensor array to detect or quantify analyte gas(es).

Similarly, the Capacitive Response (Circuit) of the $Mn^{f\&c}$-SWCNT was very low. This sensor had Capacitive Responses (Circuit) of 0.034%, 0.102%, 0.135%, 0.237%, and 0.270% at $NO_2$ concentrations of 10, 25, 50, 75, and 100 ppm respectively. Thus, the average Capacitive Response (Circuit) for this sensor was 0.156% at the $NO_2$ concentrations ranging from 1 to 100 ppm. This result indicated that a sensor device comprising only one $Mn^{f\&c}$-SWCNT sensor and a Capacitive Response (Circuit) analysis unit cannot be used for detection or quantification of $NO_x$ gases. However, this sensor can be used together with other sensors in a device comprising a sensor array to detect or quantify analyte gas(es).

Sensor sensitivities are calculated from the slopes of the Electronic Property Response (Resistive Response (Circuit) or the Capacitive Response (Circuit)) vs. the analyte concentration, for example, by using the following formulae:

Resistive Sensitivity(Circuit)=ΔResistive Response (Circuit)/Δppm

Capacitive Sensitivity(Circuit)=ΔCapacitive Response (Circuit)/Δppm

These sensitivities were calculated at two analyte concentration ranges, (a) 0 ppm to 10 ppm (i.e. Δppm=10–0) and (b) 100 ppm to 250 ppm (i.e. Δppm=250–100). The first analyte concentration range for the $Ti^{f\&c}$-SWCNT sensor was 0 ppm to 100 ppm. At these concentration ranges, the response curves were relatively linear. These calculated sensitivities are summarized in Tables 1 to 4.

The results showed that the sensitivities varied from sensor to sensor for each concentration range. Such sensitivity variations may be used in detection or quantification of more than one analyte gas by constructing a sensor array comprising at least two sensors where each sensor comprises a non-carbon material that is different than that of the other. In such an array, one sensor may also comprise only a carbon nanotube, since, as shown in this Example, the Starting CNT sensor had a sensitivity value distinctly different than that of the others.

From these sensitivity values, the sensor enhancement factor for the $NO_2$ detection may be determined by dividing the sensitivity of a sensor comprising filled or filled and coated SWCNT by that of a sensor comprising the starting SWCNT. The enhancement factor quantifies the degree of improvement or attenuation in the sensor's response to $NO_2$ due to incorporation of one or more non-carbon materials to a carbon nanotube over the range of various concentrations. The enhancement factors are shown in Tables 1 to 4.

Figure 15:
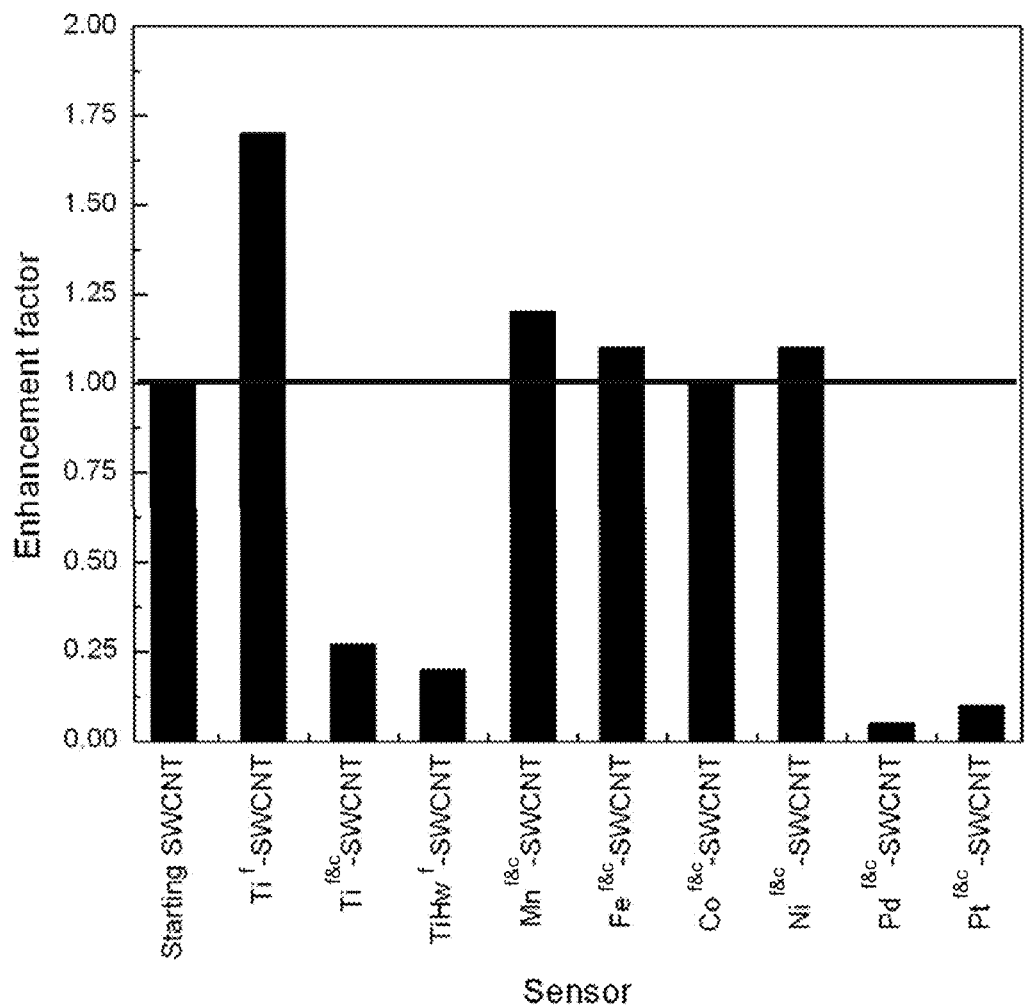
FIG. 15 shows the sensor enhancement factors calculated from Resistive Response (Circuit) of the sensors in the $NO_2$ concentration range of 0 ppm-10 ppm. (The enhancement factor of the $Ti^{f\&c}$-SWCNT sensor was calculated in the concentration range of 0 ppm to 100 ppm.).
Figure 16:
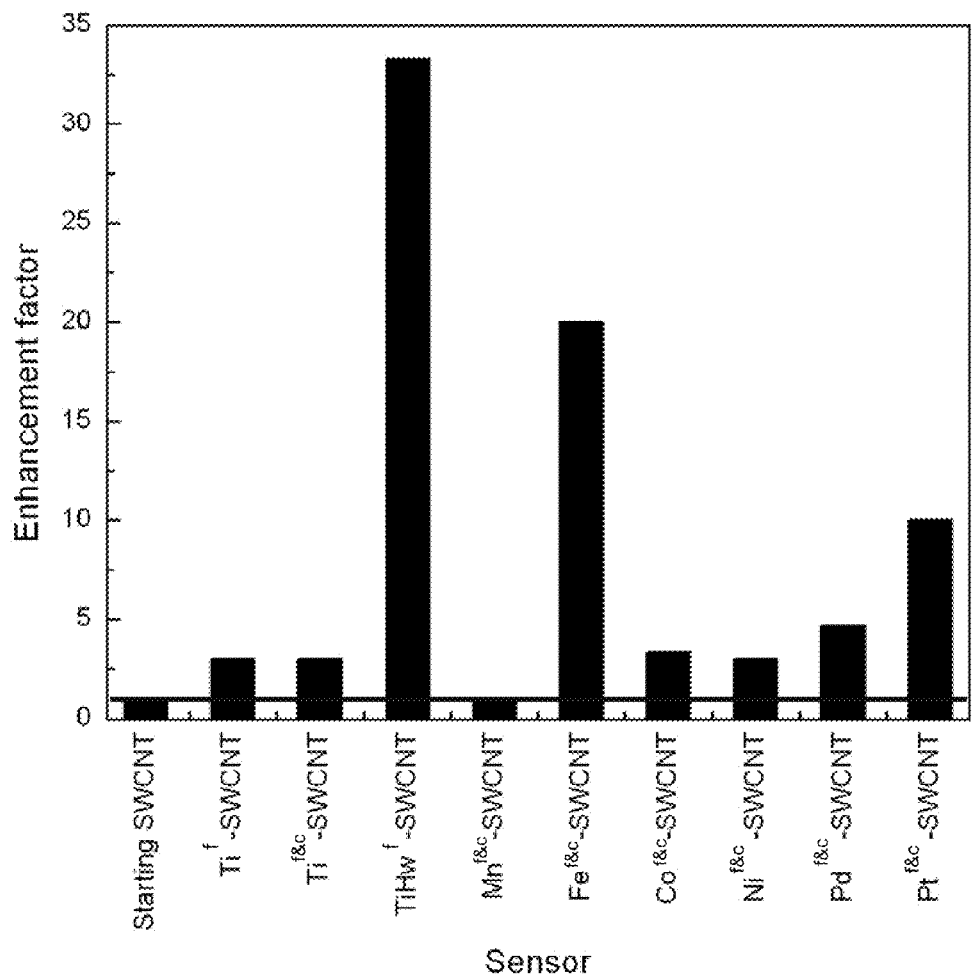
FIG. 16 shows the sensor enhancement factors calculated from Capacitive Response (Circuit) of the sensors in the $NO_2$ concentration range of 0 ppm-10 ppm. (The enhancement factor of the $Ti^{f\&c}$-SWCNT sensor was calculated in the concentration range of 0 ppm to 100 ppm.).

These enhancement factors may also be used, instead of the sensor sensitivity, in detection or quantification of more than one analyte gas by constructing a sensor array device. Since each sensor may respond to each analyte in a unique manner, providing a unique enhancement factor; the array device comprising these sensors produces a unique smell-print for each analyte. For example, a smell-print for $NO_2$ gas is schematically shown in FIG. 15 and numerically on Table 1. Such smell-prints may be used for detection or quantification purposes. Lu et al., in "A carbon nanotube sensor array for sensitive gas discrimination using principal component analysis", J. Electrochem. Chem., (2006), volume 593, at section starting on page 108, left column-last paragraph and ending on page 109, right column-first paragraph disclose how to use such smell-prints for detection or quantification in detail.

TABLE 1

Resistive Sensitivities (Circuit) of the sensors in the concentration range of 0 ppm-10 ppm $NO_2$. (The sensitivity of the $Ti^{f\&c}$-SWCNT sensor was calculated in the concentration range of 0 ppm to 100 ppm.)

| Sensor | Resistive Sensitivity (Circuit) (% ppm$^{-1}$) | Enhancement factor | Minimum detection limit (ppm) |
| --- | --- | --- | --- |
| $Ti^{f}$-SWCNT | 3.4 | 1.70 | $4.7 \times 10^{-4}$ |
| $Mn^{f\&c}$-SWCNT | 2.4 | 1.20 | $2.4 \times 10^{-5}$ |
| $Fe^{f\&c}$-SWCNT | 2.2 | 1.10 | $1.4 \times 10^{-3}$ |
| $Ni^{f\&c}$-SWCNT | 2.1 | 1.05 | $6.5 \times 10^{-3}$ |
| Starting SWCNT | 2.0 | 1.00 | $4.3 \times 10^{-5}$ |
| $Co^{f\&c}$-SWCNT | 1.7 | 0.85 | $6.9 \times 10^{-3}$ |
| $TiH_w^{f}$-SWCNT | 0.4 | 0.20 | $2.0 \times 10^{-1}$ |
| $Pt^{f\&c}$-SWCNT | 0.2 | 0.10 | $7.1 \times 10^{-1}$ |
| $Ti^{f\&c}$-SWCNT | 0.17 | 0.28 | $7.0 \times 10^{-3}$ |
| $Pd^{f\&c}$-SWCNT | 0.1 | 0.05 | $5.0 \times 10^{-1}$ |

TABLE 2

Resistive Sensitivities (Circuit) of the sensors in the concentration range of 100 ppm to 250 ppm $NO_2$.

| Sensor | Resistive Sensitivity (Circuit) (% ppm$^{-1}$) | Enhancement factor |
| --- | --- | --- |
| $Pt^{f\&c}$-SWCNT | 0.25 | 2.72 |
| $Ti^{f\&c}$-SWCNT | 0.18 | 2.57 |
| $Pd^{f\&c}$-SWCNT | 0.16 | 1.74 |
| $TiH_w^{f}$-SWCNT | 0.15 | 1.63 |
| $Co^{f\&c}$-SWCNT | 0.095 | 1.03 |
| $Ni^{f\&c}$-SWCNT | 0.095 | 1.03 |
| Starting SWCNT | 0.092 | 1.00 |
| $Ti^{f}$-SWCNT | 0.08 | 0.87 |
| $Fe^{f\&c}$-SWCNT | 0.07 | 0.76 |
| $Mn^{f\&c}$-SWCNT | 0.012 | 0.13 |

TABLE 3

Capacitive Sensitivities (Circuit) of the sensors in the concentration range of 0 ppm-10 ppm $NO_2$. (The sensitivity of the $Ti^{f\&c}$-SWCNT sensor was calculated in the concentration range of 0 ppm to 100 ppm.)

| Sensor | Capacitive Sensitivity (Circuit) (% ppm$^{-1}$) | Enhancement factor | Minimum detection limit (ppm) |
| --- | --- | --- | --- |
| $TiH_w^{f}$-SWCNT | 0.100 | 33.3 | 0.06 |
| $Fe^{f\&c}$-SWCNT | 0.060 | 20.0 | 0.05 |
| $Pt^{f\&c}$-SWCNT | 0.030 | 10.0 | 0.17 |
| $Pd^{f\&c}$-SWCNT | 0.014 | 4.7 | 0.25 |
| $Co^{f\&c}$-SWCNT | 0.010 | 3.3 | 0.25 |
| $Ni^{f\&c}$-SWCNT | 0.009 | 3.0 | 0.34 |
| $Ti^{f}$-SWCNT | 0.009 | 3.0 | 0.33 |
| $Ti^{f\&c}$-SWCNT | 0.009 | 3.0 | 1.11 |
| $Mn^{f\&c}$-SWCNT | 0.003 | 1.0 | 0.99 |
| Starting SWCNT | 0.003 | 1.0 | 1.00 |

TABLE 4

Capacitive Sensitivities (Circuit) of the sensors in the concentration range of 100 ppm to 250 ppm $NO_2$.

| Sensor | Capacitive Sensitivity (Circuit) (% ppm$^{-1}$) | Enhancement factor |
| --- | --- | --- |
| $Pt^{f\&c}$-SWCNT | 1.54 | 770 |
| $Pd^{f\&c}$-SWCNT | 0.310 | 155 |
| $Ni^{f\&c}$-SWCNT | 0.100 | 50 |
| $TiH_w^{f}$-SWCNT | 0.084 | 42 |
| $Co^{f\&c}$-SWCNT | 0.075 | 38 |
| $Fe^{f\&c}$-SWCNT | 0.030 | 15 |
| $Ti^{f\&c}$-SWCNT | 0.022 | 11 |
| $Ti^{f}$-SWCNT | 0.004 | 2 |
| $Mn^{f\&c}$-SWCNT | 0.004 | 2 |
| Starting SWCNT | 0.002 | 1 |

The minimum detection limits of the sensors were calculated by using the Nyquist plots as follows. First, the sensor resistance was measured for the background gas (i.e. nitrogen). Then, the sensor resistance was measured for the 10 ppm $NO_2$—$N_2$ gas mixture. The variation of the real part (Z') of the impedance curve obtained from these measurements was $\Delta Z' = Z'_b - Z'_{mix}$. This variation was caused by 10 ppm increase in $NO_2$ concentration. The lowest resolution of the impedance analyzer was about 1 ohm for analysis with these sensors. Therefore, the minimum detection limit was 1 ohm×

10 ppm/$\Delta Z'$. For example, the detection limit for the $Ti^f$-SWCNT sensor was calculated as follows. $Z'_b$ for this sensor in $N_2$ was about 70,100 ohm and $Z'_{mix}$ in about 10 ppm $NO_2$—$N_2$ mixture was about 48,900 ohm. Then, $\Delta Z'$=70,100-48,900=21,200 ohm. Therefore, the detection limit of this sensor for $NO_2$ corresponded to 1 ohm×10 ppm/21,200 ohm=4.7×$10^{-4}$ ppm or 0.47 ppb.

As shown in Tables 1 and 2, the minimum detection level of $NO_2$ concentration varied from sensor to sensor. For example, the minimum detectable concentration for the $Ti^f$-SWCNT sensor, as determined by the Resistive Response (Circuit), was 0.47 parts-per-billion (ppb) $NO_2$. It was 500 ppb $NO_2$ for the $Pd^{f\&c}$-SWCNT sensor. The results also demonstrated that some of the sensors may measure $NO_2$ concentrations down to ppb levels.

The minimum detection level depends on the resolution provided by the impedance analyzer when the sensors are analyzed for the electronic property variation. Thus, with analyzers that offer better resolutions than that of the Novocontrol analyzer, the minimum detection level may further be decreased below the levels discussed above. Therefore, these detection limits are for illustration purpose and do not limit the scope of the instant invention.

Above results indicated that the SWCNT sensors comprising Ti, titanium hydrides, Fe, Co, Ni, Pd, Pt or combinations thereof may be suitable for detection or quantification of $NO_2$ above the minimum detection limits of these sensors. These results further indicated that a device comprising the $Mn^{f\&c}$-SWCNT sensor, and the Resistive Response analysis unit or the Resistive Response (Circuit) analysis unit may also be suitable for detection or quantification of $NO_2$ above the minimum detection limits of these sensors.

Example 13

Sensor Comprising Ti Filled SWCNT Article for Detection or Quantification of Ethanol Vapor In this example, the sensors were prepared and analyzed in the same manner as described in above examples, except the following. The analyte gas was ethanol vapor.

For sensor impedance measurements in ethanol vapor as a test gas, the parent ethanol vapor (about 1000 ppm in nitrogen) was diluted with the ultra-high purity $N_2$ to yield concentrations of ethanol vapor varying in the range of 0 ppm to 250 ppm. The flow rate of the diluted test gas was controlled at about 100 milliliter per minute by means of an MKS multi-gas controller (Model 647C). Each concentration of ethanol-nitrogen mixture was allowed to flow over the assembled sensor for about 10 minutes prior to acquiring the frequency dependent impedance values.

This sensor was then analyzed by modeling the impedance using an equivalent circuit method shown in FIG. 3. The total impedance (Z) was resolved into a real part (Z') and an imaginary part (Z") and a semicircular Nyquist plot was obtained, which was modeled to intersect the Z' axis at two points. The difference between these two intersection points yielded the real part of the resistance.

It was found that $R_1$, the uncompensated ohmic resistance of the sensor, did not show any dependence to the ethanol vapor concentration. That is, the contribution of $R_1$ to the Resistive Response (Circuit) was less than 0.03% when the response was averaged in the ethanol concentration range of 1 ppm to 100 ppm. Likewise, the parameter $C_2$, representing the capacitance of the sensor, did not exhibit any meaningful dependence on adsorbed ethanol concentration. That is, in the concentrations ranging from 1 to 100 ppm, the average Capacitive Response (Circuit) was less than 1%. It was thereby concluded that the Electronic Property Responses, $R_1$ and $C_2$ are not suitable for detection or quantification of the ethanol vapor with $Ti^f$-SWCNT sensor.

Figure 17:
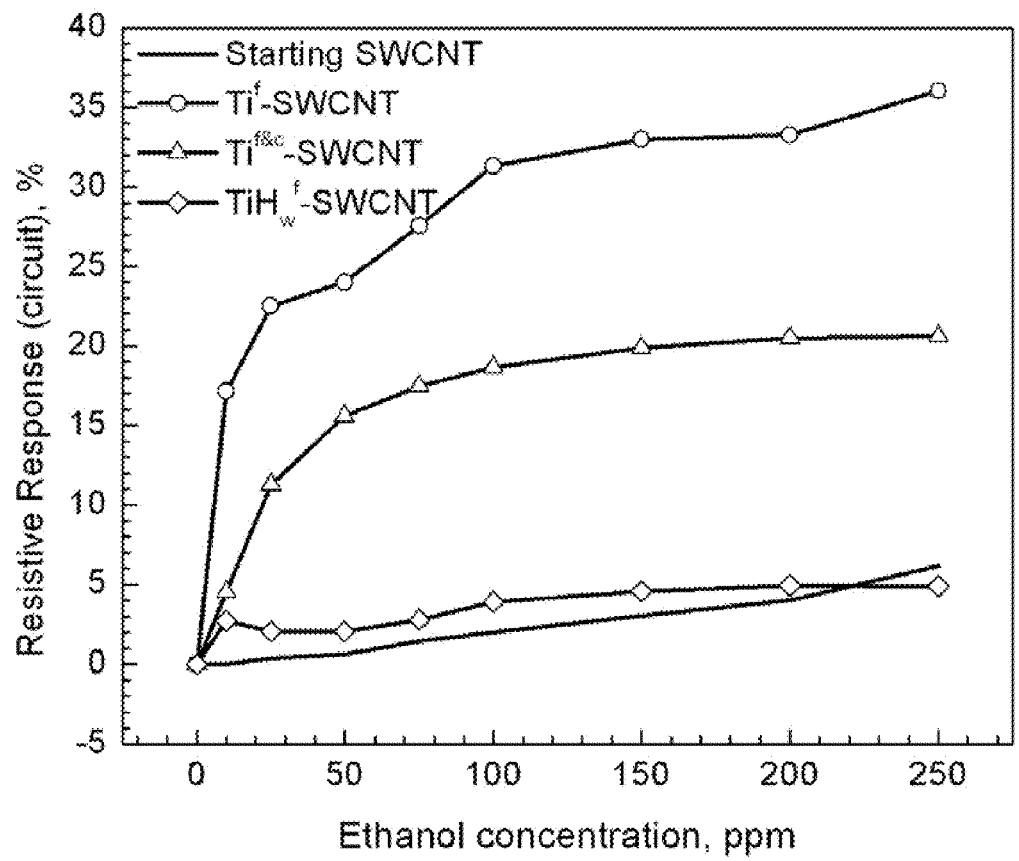
FIG. 17 shows the Resistive Response (Circuit) of the $Ti^f$-SWCNT sensor, $TiH_w^f$-SWCNT sensor, $Ti^{f\&c}$-SWCNT sensor and the Starting SWCNT sensor as a function of ethanol vapor concentration.

The other circuit parameter $R_2$, showing the only observable response, decreased in the presence of ethanol vapor. The variation of the Resistive Response (Circuit) of the sensor as a function of ethanol vapor concentration is shown in FIG. 17. Same impedance measurements were repeated for the Starting SWCNT sensor.

As shown in FIG. 17, the Resistive Response of the Starting SWCNT sensor increased with increasing ethanol vapor concentration, attaining about 5% at about 250 ppm ethanol vapor concentration. This result indicated that the Starting SWCNT sensor is not very sensitive, particularly at low ethanol concentrations.

As compared, the $Ti^f$-SWCNT sensor showed considerably higher response. These results indicated that the incorporation of non-carbon material to the carbon not only significantly improved the response of the sensor, but also made such sensors viable alternatives to commercially existing sensors.

Example 14

Sensors for Detection and Quantification of Ethanol Vapor

In this example, the sensors were prepared and analyzed in the same manner as described in above examples, except the following. The analyte gas was ethanol vapor.

It was found that $R_1$, the uncompensated ohmic resistance of these sensors, did not show any dependence to the ethanol vapor concentration. That is, the contribution of $R_1$ to the Resistive Response (Circuit) was less than 0.03% when the response was averaged in the ethanol concentration range of 1 ppm to 100 ppm. Likewise, the parameter $C_2$, representing the capacitance of the sensor, did not exhibit any meaningful dependence on adsorbed ethanol concentration. That is, in the concentrations ranging from 1 to 100 ppm, the average Capacitive Response (Circuit) was less than 1%. It was thereby concluded that the Electronic Property Responses, $R_1$ and $C_2$, are not suitable for detection or quantification of the ethanol vapor with these sensors.

Figure 18:
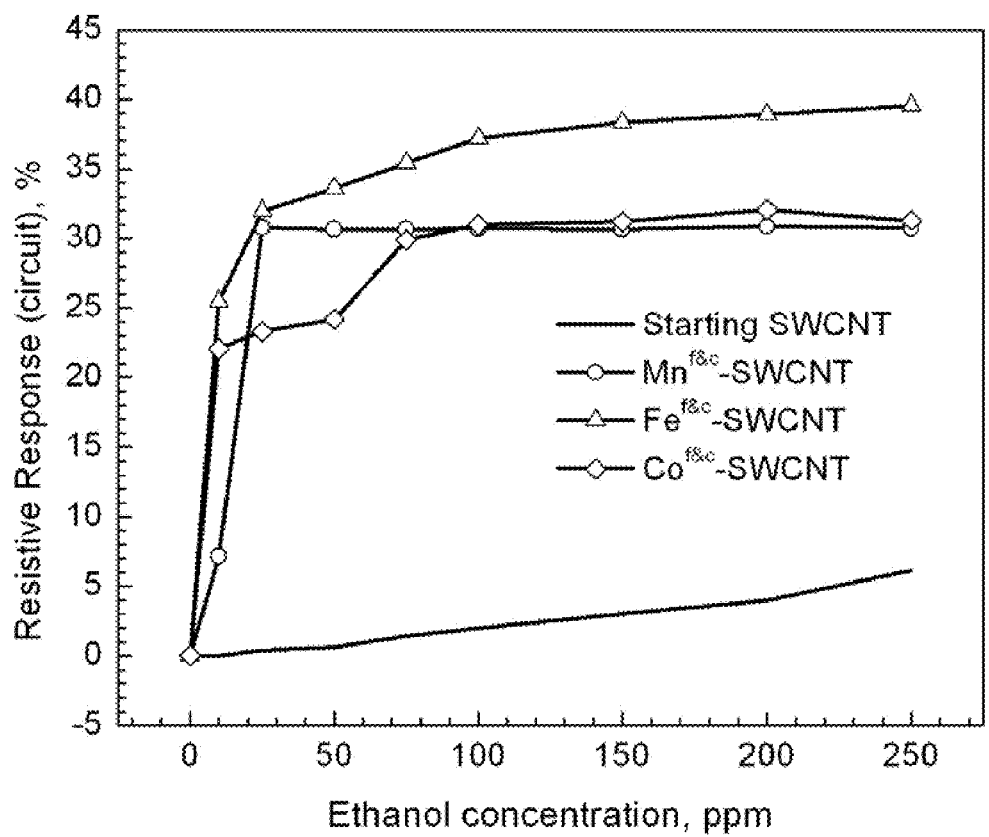
FIG. 18 shows the Resistive Response (Circuit) of the $Mn^{f\&c}$-SWCNT, $Fe^{f\&c}$-SWCNT, $Co^{f\&c}$-SWCNT and the Starting SWCNT sensor as a function of ethanol vapor concentration.
Figure 19:
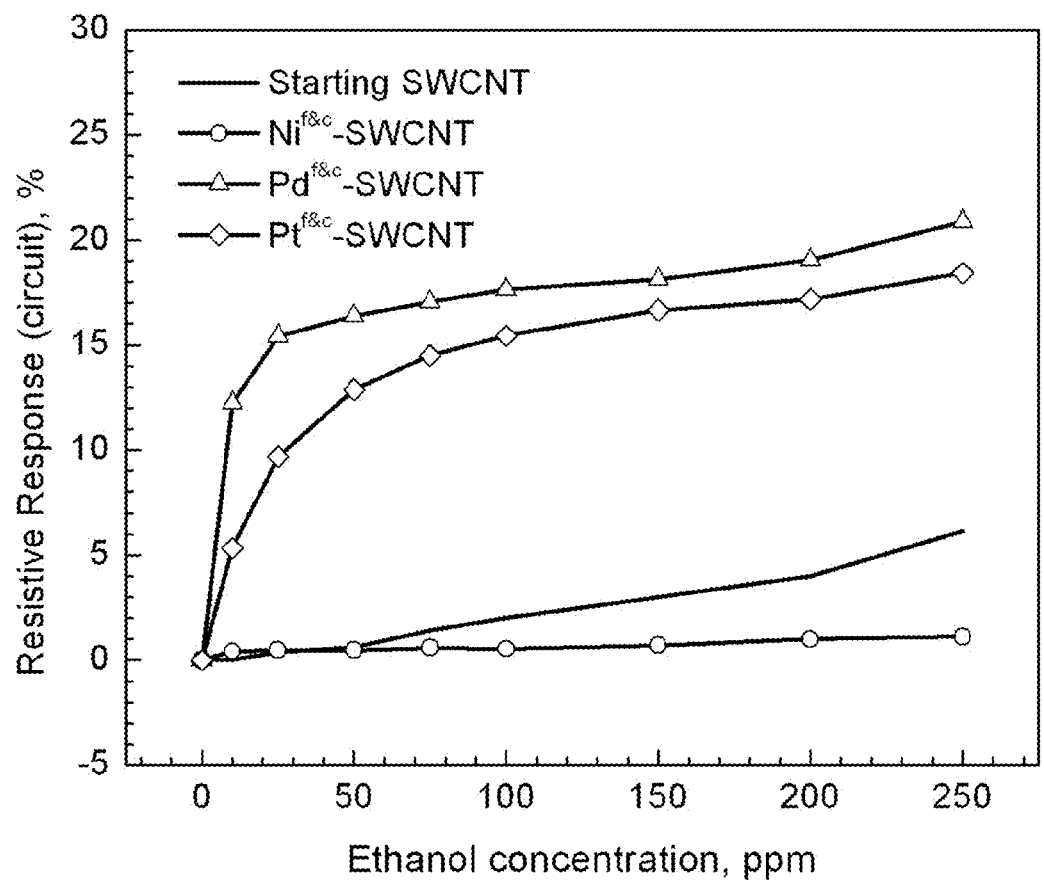
FIG. 19 shows the Resistive Response (Circuit) of the $Pd^{f\&c}$-SWCNT, $Pt^{f\&c}$-SWCNT, $Ni^{f\&c}$-SWCNT and the Starting SWCNT sensor as a function of ethanol vapor concentration.

The variation of the Resistive Response (Circuit) of these sensors as a function of ethanol vapor concentration is shown in FIGS. 17 to 19. All sensors showed higher resistive responses than the Starting SWCNT sensor for ethanol concentrations lower than 10 ppm. The $Fe^{f\&c}$-SWCNT, $Co^{f\&c}$-SWCNT, $Ti^f$-SWCNT, $Pd^{f\&c}$-SWCNT, $Mn^{f\&c}$-SWCNT, $Ti^{f\&c}$-SWCNT and $Pt^{f\&c}$-SWCNT sensors showed significantly higher resistive responses than the Starting SWCNT sensor for all ethanol concentrations investigated. The $TiH_w^f$-SWCNT sensor did not show significant resistive response increase for ethanol concentrations above 10 ppm. This sensor may be suitable for detection of ethanol vapors for concentrations lower than 10 ppm.

The average Resistive Response (Circuit) of the $Ni^{f\&c}$-SWCNT was very low, less than 0.53% at the ethanol vapor concentrations ranging from 1 to 100 ppm. This result indicated that a sensor device comprising only one $Ni^{f\&c}$-SWCNT sensor and a Resistive Response (Circuit) analysis unit cannot be used for detection or quantification of ethanol vapor. However, this sensor can be used together with other sensors in a device comprising a sensor array to detect or quantify analyte gas(es).

Figure 20:
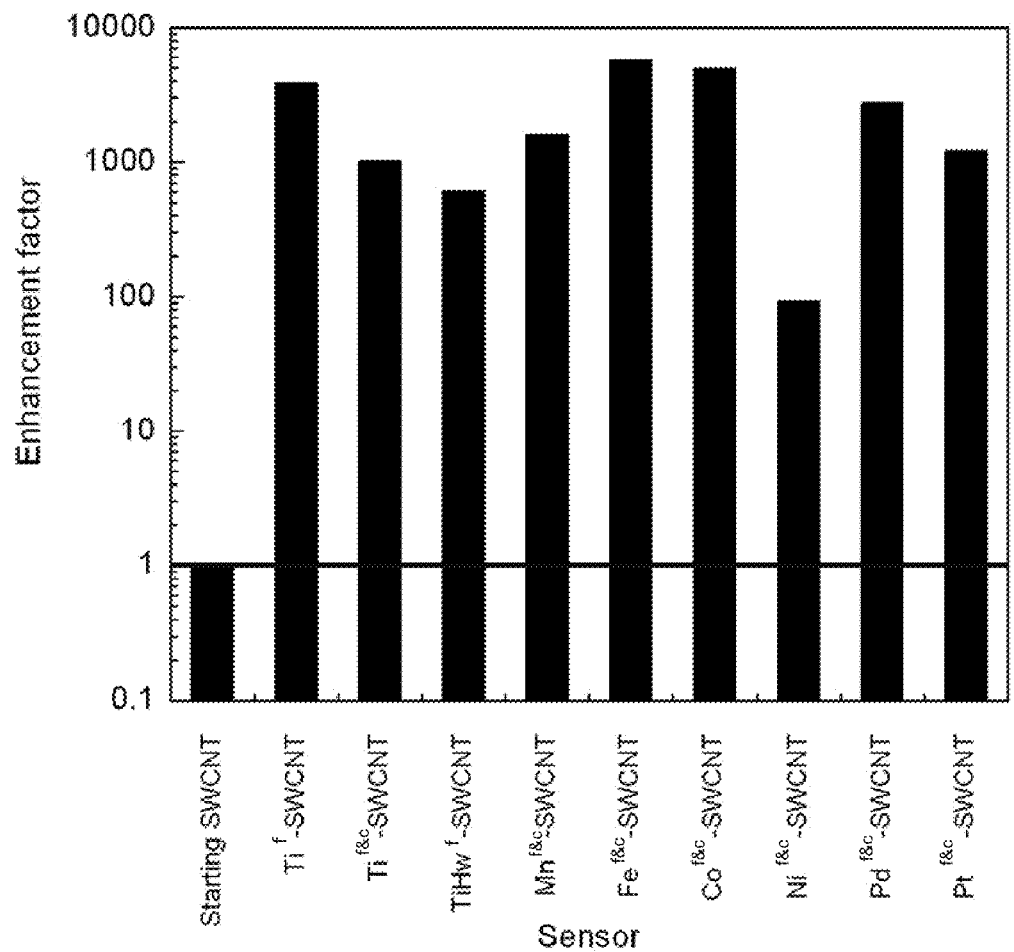
FIG. 20 shows the sensor enhancement factors calculated from Resistive Response (Circuit) of the sensors in the ethanol concentration range of 0 ppm to 10 ppm.

The sensor sensitivities to ethanol vapor were calculated from the slope of each sensor's response curve in the range of 0 ppm to 10 ppm ethanol concentration. These calculated sensitivities are summarized in Table 5. The results showed that all the sensors had sensitivities significantly higher than that of the Starting SWCNT sensor for ethanol concentrations at about or below 10 ppm. As shown in FIG. 20, all sensors comprising the organized assemblies of this invention exhibited at least about one order of magnitude enhancement in sensitivity to ethanol detection versus the Starting SWCNT sensor.

TABLE 5

Resistive Sensitivities (Circuit) of the sensors in the concentration range of 0 ppm to 10 ppm ethanol.

| Sensor | Resistive Sensitivity (Circuit) (% ppm$^{-1}$) | Minimum detection limit (ppb) |
|---|---|---|
| Fe$^{f\&c}$-SWCNT | 2.5 | 0.23 |
| Co$^{f\&c}$-SWCNT | 2.2 | 31 |
| Ti$^f$-SWCNT | 1.7 | 0.35 |
| Pd$^{f\&c}$-SWCNT | 1.2 | 14 |
| Mn$^{f\&c}$-SWCNT | 0.7 | 29 |
| Ti$^{f\&c}$-SWCNT | 0.5 | 14 |
| Pt$^{f\&c}$-SWCNT | 0.5 | 91 |
| TiH$_w^f$-SWCNT | 0.3 | 1000 |
| Ni$^{f\&c}$-SWCNT | 0.04 | 1000 |
| Starting SWCNT | 0.00045 | 500 |

As shown in Table 5, minimum detection level varied from sensor to sensor. For example, minimum detectable signal for the Fe$^{f\&c}$-SWCNT sensor was 0.23 parts-per-billion (ppb) of ethanol at about 1 ohm. While the Starting SWCNT sensor produced a minimum detection limit at about 500 ppb of ethanol, all other sensors, with the exception of the TiH$_w^f$-SWCNT and Ni$^{f\&c}$-SWCNT sensors, showed much lower minimum detection limits. The minimum detection limits of the Fe$^{f\&c}$-SWCNT, Co$^{f\&c}$-SWCNT, Ti$^f$-SWCNT, Pd$^{f\&c}$-SWCNT, Mn$^{f\&c}$-SWCNT, Ti$^{f\&c}$-SWCNT and Pt$^{f\&c}$-SWCNT sensors were lower than 100 ppb. Two of the metal-CNT hybrid sensors, Fe$^{f\&c}$-SWCNT and Ti$^f$-SWCNT, were capable of detecting ethanol down to the parts-per-trillion (ppt) level.

Above results indicated that the SWCNT sensors comprising Fe, Co, Ti, Pd, Mn, Pt, or mixtures (or alloys) thereof may particularly be suitable for detection of ethanol at concentrations above the minimum detection limits of these sensors. As for the TiH$_w^f$-SWCNT sensor, the minimum detection limit is 1,000 ppb (i.e. 1 ppm). Therefore, this sensor may be suitable for detecting ethanol vapor at concentrations in the range of 1 ppm to 10 ppm.

Example 15

Sensor Comprising Pt Filled and Coated SWCNT Article for Detection or Quantification of Hydrogen Gas A Pt$^{f\&c}$-SWCNT sensor and a Starting SWCNT sensor were prepared and analyzed in the same manner as described in above examples, except the following. The analyte gas in this example was hydrogen.

For sensor impedance measurements in hydrogen as an analyte gas, the parent hydrogen (about 5% in nitrogen) was diluted with the ultra-high purity N$_2$ to yield concentrations of hydrogen varying in the range of 0% to 3%.

Figure 21:
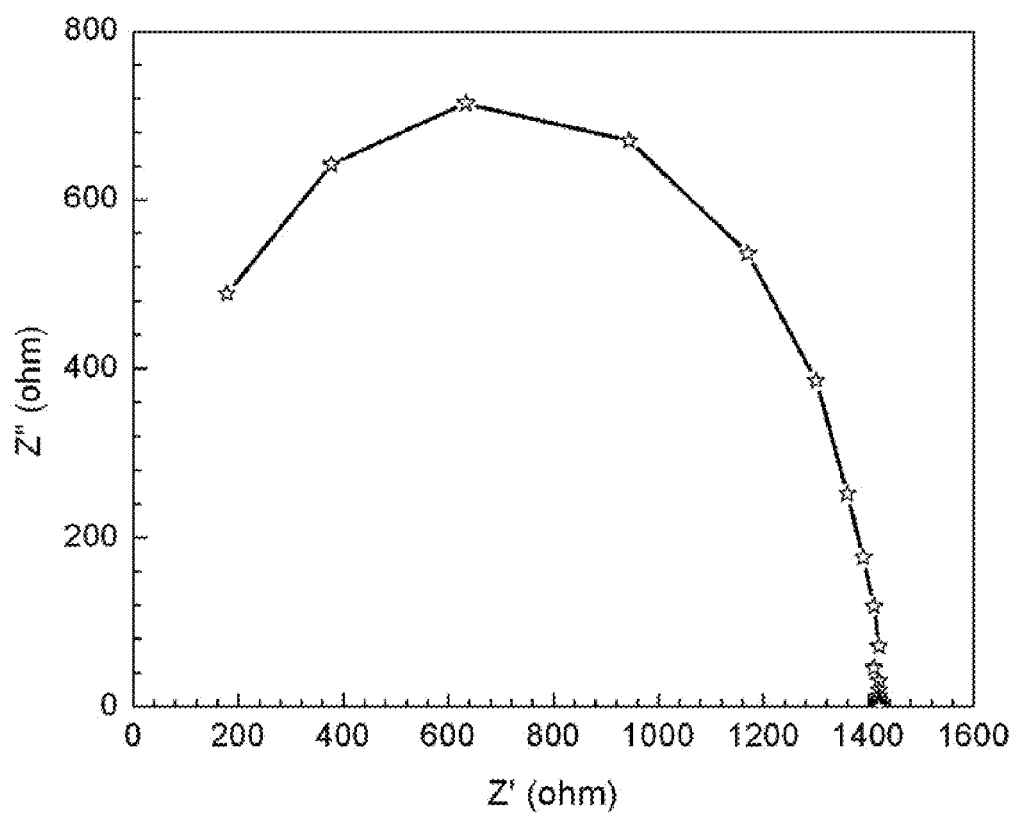
FIG. 21 shows the Nyquist plot for the $Pt^{f\&c}$-SWCNT sensor responding at room temperature to about 1% hydrogen and nitrogen mixture.
Figure 22:
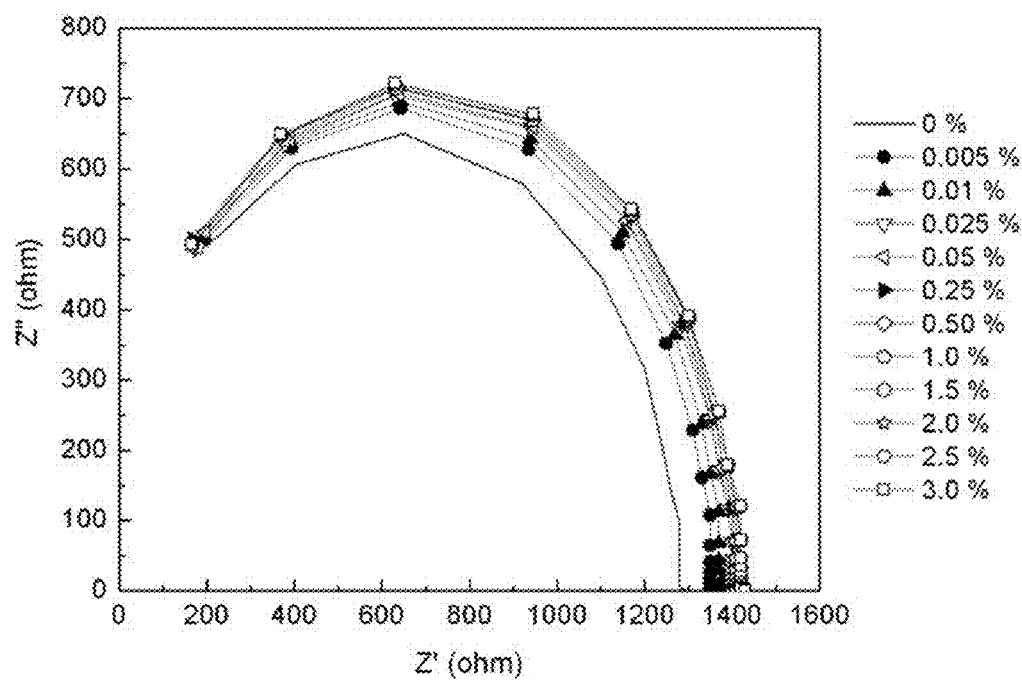
FIG. 22 shows the Nyquist plots for the $Pt^{f\&c}$-SWCNT sensor responding at room temperature to hydrogen and nitrogen mixtures in the range of 0% to 3%.

This sensor was then analyzed by modeling the impedance using an equivalent circuit method, shown in FIG. 3. The total impedance (Z) was resolved into a real part (Z') and an imaginary part (Z") and a semicircular Nyquist plot was obtained. This plot was shown in FIG. 21 for about 1% hydrogen concentration. This plot was modeled to intersect the Z' axis at two points. The difference between these two intersection points yielded the real part of the resistance. For example, the real resistance was about 1,420 ohms for the Pt$^{f\&c}$-SWCNT sensor at about 1% hydrogen concentration. Same measurements were repeated at various hydrogen concentrations to determine the sensor response as a function of the concentration. The same measurement was also repeated for UHP N$_2$ to determine the response of the sensor to the background gas. The measurement results are shown in FIGS. 22.

It was found that R$_1$, the uncompensated ohmic resistance of the sensor, did not show any dependence to the hydrogen concentration. That is, the contribution of R$_1$ to the Resistive Response (Circuit) was less than 0.03% when the response was averaged in the hydrogen concentration range of 1 ppm to 100 ppm. Likewise, the parameter C$_2$, representing the capacitance of the sensor, did not exhibit any meaningful dependence on adsorbed hydrogen concentration. That is, in the concentrations ranging from 1 to 100 ppm, the average Capacitive Response (Circuit) was less than 1%. It was thereby concluded that the Electronic Property Responses, R$_1$ and C$_2$, are not suitable for detection or quantification of hydrogen with the Pt$^{f\&c}$-SWCNT sensor.

Figure 23:
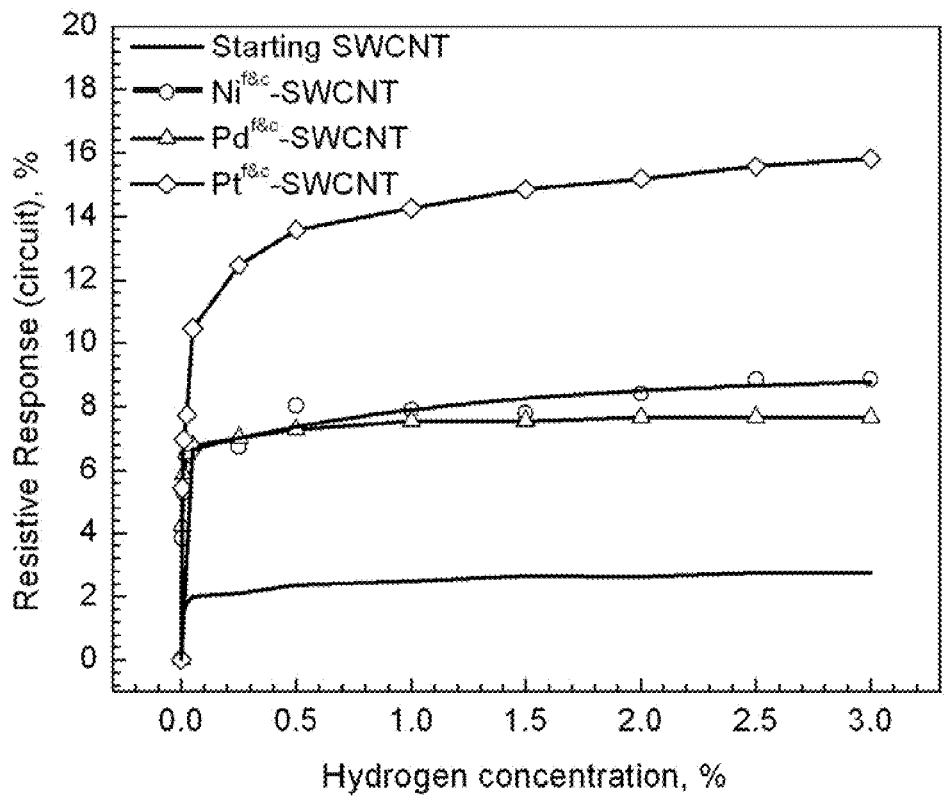
FIG. 23 shows the Resistive Response (Circuit) of the $Ni^{f\&c}$-SWCNT sensor, $Pd^{f\&c}$-SWCNT sensor, $Pt^{f\&c}$-SWCNT sensor and the Starting SWCNT sensor as a function of hydrogen concentration.
Figure 24:
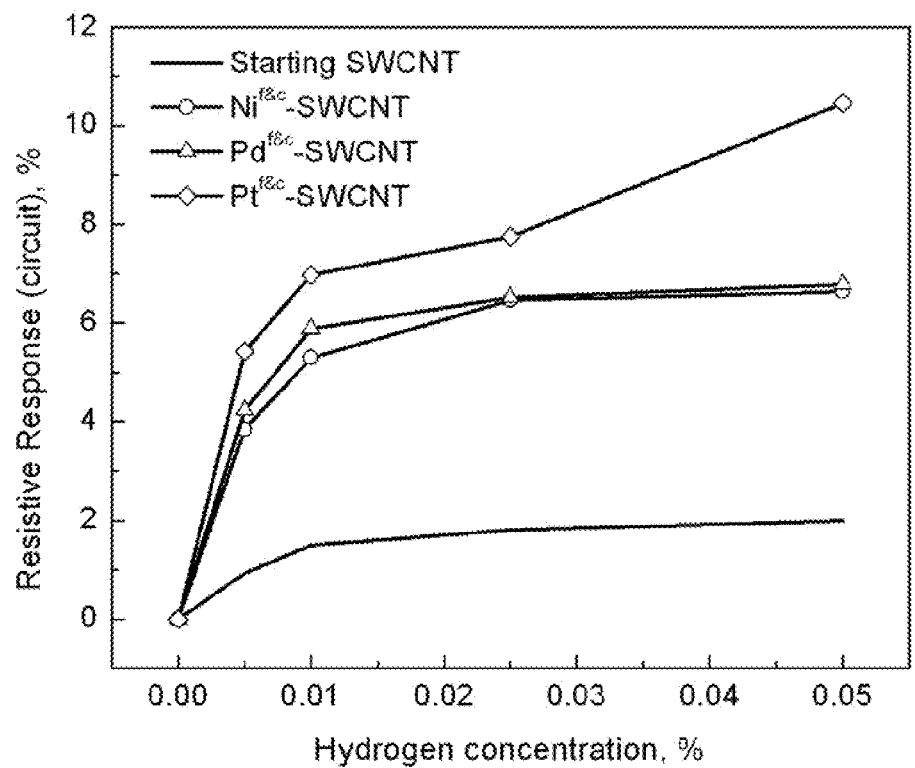
FIG. 24 shows the Resistive Response (Circuit) of the $Ni^{f\&c}$-SWCNT sensor, $Pd^{f\&c}$-SWCNT sensor, $Pt^{f\&c}$-SWCNT sensor and the Starting SWCNT sensor as a function of hydrogen concentration in the range of 0% to 0.05%.
Figure 25:
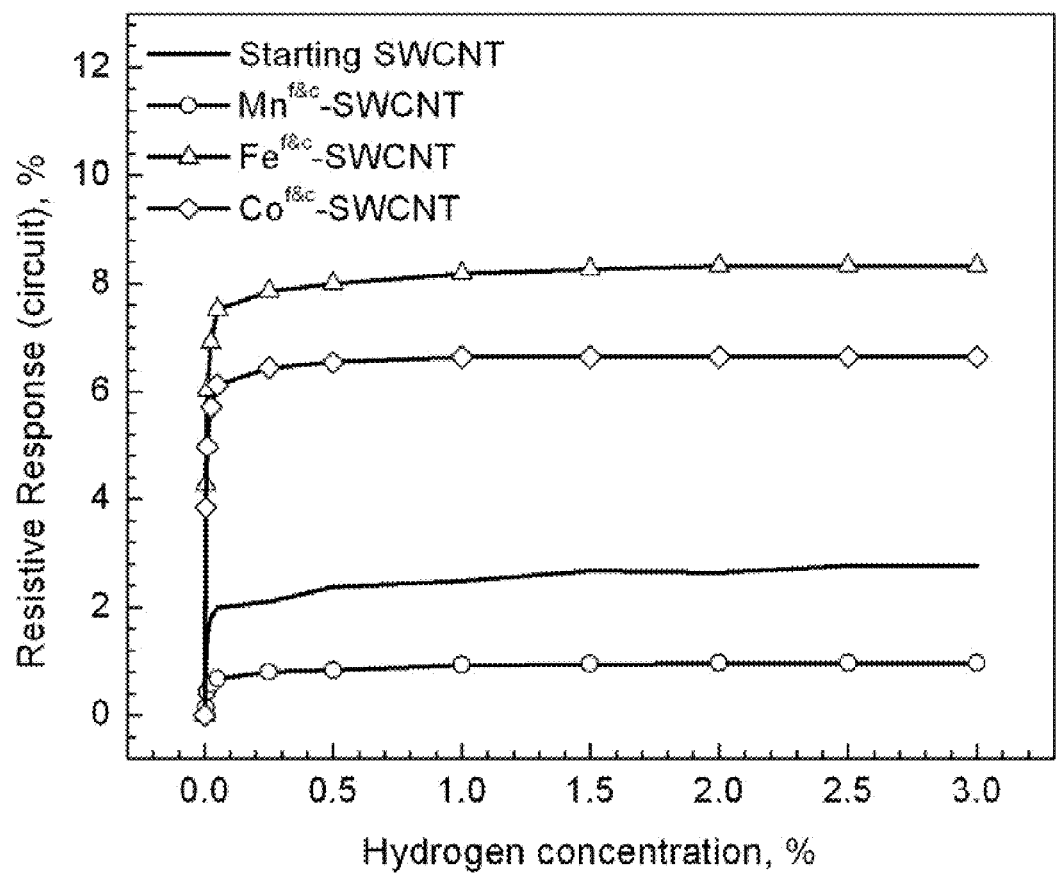
FIG. 25 shows the Resistive Response (Circuit) of the $Mn^{f\&c}$-SWCNT, $Fe^{f\&c}$-SWCNT, $Co^{f\&c}$-SWCNT and the Starting SWCNT sensor as a function of hydrogen concentration.
Figure 26:
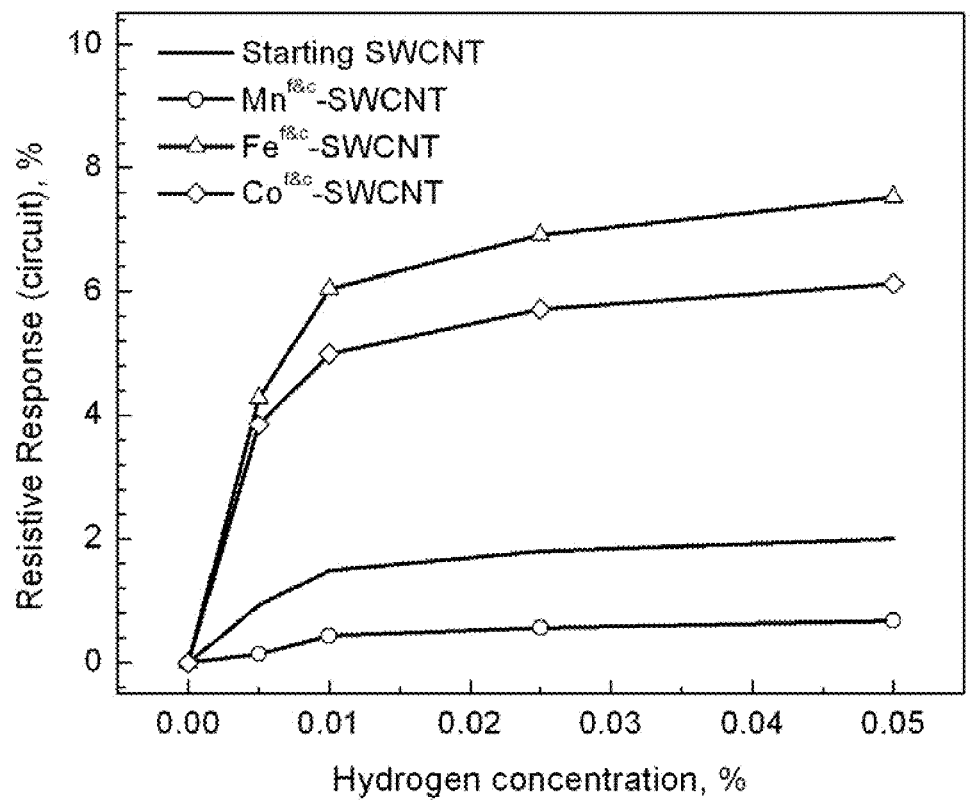
FIG. 26 shows the Resistive Response (Circuit) of the $Mn^{f\&c}$-SWCNT, $Fe^{f\&c}$-SWCNT, $Co^{f\&c}$-SWCNT and the Starting SWCNT sensor as a function of hydrogen concentration in the range of 0% to 0.05%.
Figure 27:
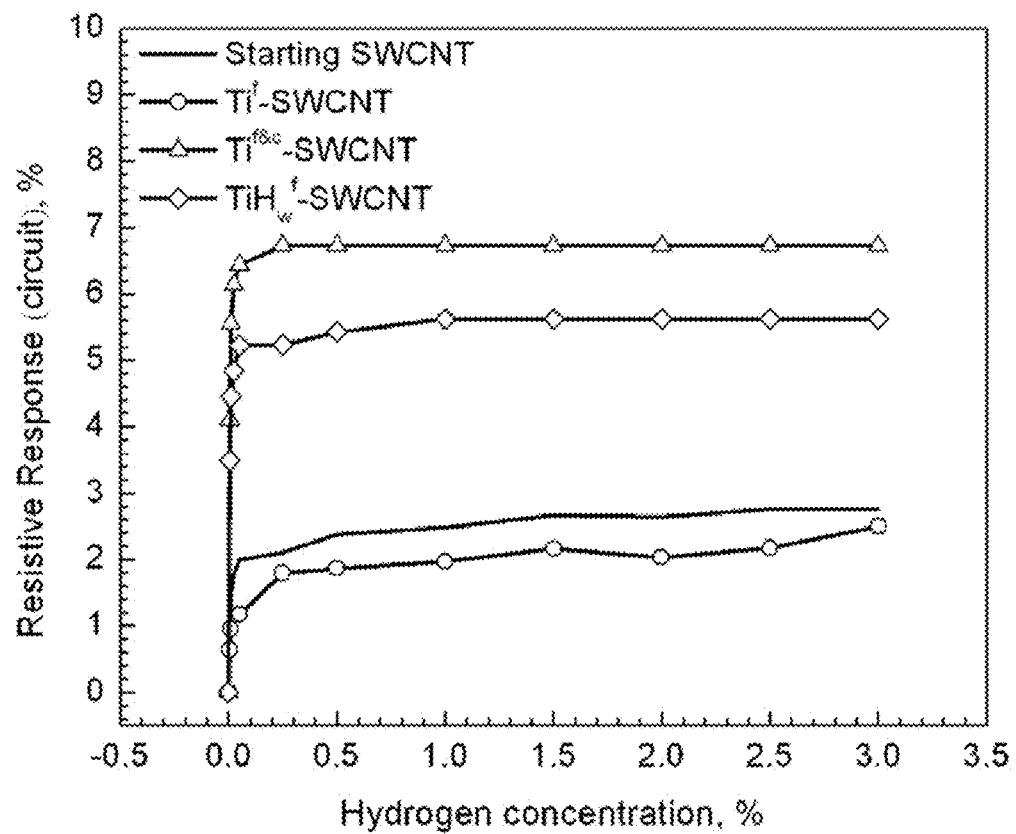
FIG. 27 shows the Resistive Response (Circuit) of the $Ti^f$-SWCNT sensor, $Ti^{f\&c}$-SWCNT sensor, $TiH_w^f$-SWCNT sensor and the Starting SWCNT sensor as a function of hydrogen concentration.
Figure 28:
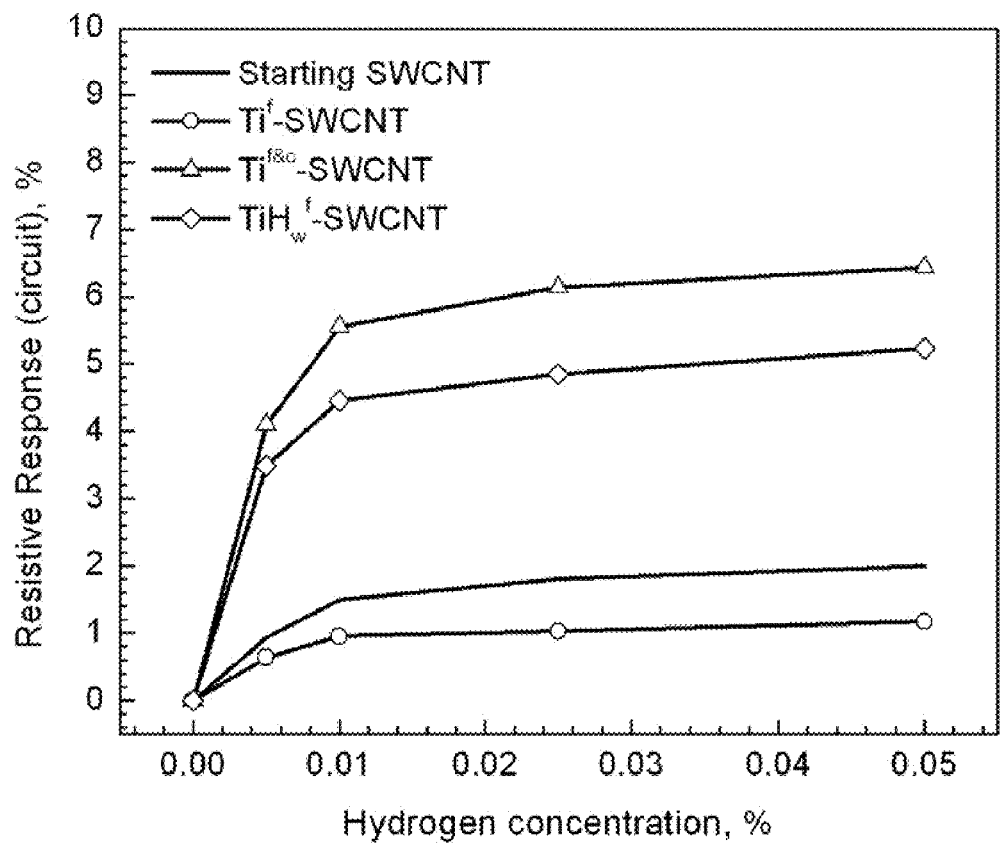
FIG. 28 shows the Resistive Response (Circuit) of the $Ti^f$-SWCNT sensor, $Ti^{f\&c}$-SWCNT sensor, $TiH_w^f$-SWCNT sensor and the Starting SWCNT sensor as a function of hydrogen concentration in the range of 0% to 0.05%.

The other circuit parameter R$_2$, showing the only observable response, increased in the presence of hydrogen. The variation of the Resistive Response (Circuit) of the sensor derived from R$_2$ as a function of hydrogen concentration is shown in FIGS. 23 and 24. Same impedance measurements were repeated for the Starting SWCNT sensor.

As shown in FIG. 23, the normalized resistive response of the Starting SWCNT sensor was less than 3% for all hydrogen concentrations.

As compared to this sensor, the Pt$^{f\&c}$-SWCNT sensor showed considerably higher responses to all hydrogen concentrations. These results indicated that the incorporation of non-carbon material to the carbon significantly improved the response of the sensor, thus it made such sensors viable alternatives to commercially existing sensors.

Example 16

Sensors for Detection and Quantification of Hydrogen Gas

Various sensors were prepared and analyzed in the same manner as described in above examples, except the following. The analyte gas was hydrogen.

It was found that R$_1$, the uncompensated ohmic resistance of these sensors, did not show any dependence to the hydrogen concentration. That is, the contribution of R$_1$ to the Resistive Response (Circuit) was less than 0.03% when the response was averaged in the hydrogen concentration range of 1 ppm to 100 ppm. Likewise, the parameter C$_2$, representing the capacitance of the sensor, did not exhibit any meaningful dependence on adsorbed hydrogen concentration. That is, in the concentrations ranging from 1 to 100 ppm, the average Capacitive Response (Circuit) was less than 1%. It was thereby concluded that the Electronic Property Responses, R$_1$ and C$_2$ are not suitable for detection or quantification of hydrogen with these sensors.

The other circuit parameter R$_2$, showing the only observable response, increased in the presence of hydrogen for some sensors. The variation of the Resistive Response (Circuit) of these sensors as a function of hydrogen concentration derived from $R_2$ is shown in FIGS. 23 to 28. The $Pt^{f\&c}$-SWCNT, $Fe^{f\&c}$-SWCNT, $Pd^{f\&c}$-SWCNT, $Ti^{f\&c}$-SWCNT, $Ni^{f\&c}$-SWCNT, $Co^{f\&c}$-SWCNT and $TiH_w^f$-SWCNT sensors showed higher resistive responses than the Starting SWCNT sensor for all hydrogen concentrations investigated.

However, the $Ti^f$-SWCNT sensor and the $Mn^{f\&c}$-SWCNT sensor had average Resistive Responses (Circuit) less than 1% and 0.45% respectively in the concentrations ranging from 1 to 100 ppm. It was thereby concluded that the Resistive Response (Circuit) derived from $R_2$ is not suitable for detection or quantification of the hydrogen with the $Ti^f$-SWCNT sensor and the $Mn^{f\&c}$-SWCNT sensor.

The calculated sensitivities for these sensors are summarized in Table 6. The results showed that the $Pt^{f\&c}$-SWCNT, $Fe^{f\&c}$-SWCNT, $Pd^{f\&c}$-SWCNT, $Ti^{f\&c}$-SWCNT, $Ni^{f\&c}$-SWCNT, $Co^{f\&c}$-SWCNT and $TiH_w^f$-SWCNT sensors had sensitivities higher than that of the Starting SWCNT sensor for hydrogen concentrations at about or below 50 ppm.

Figure 29:
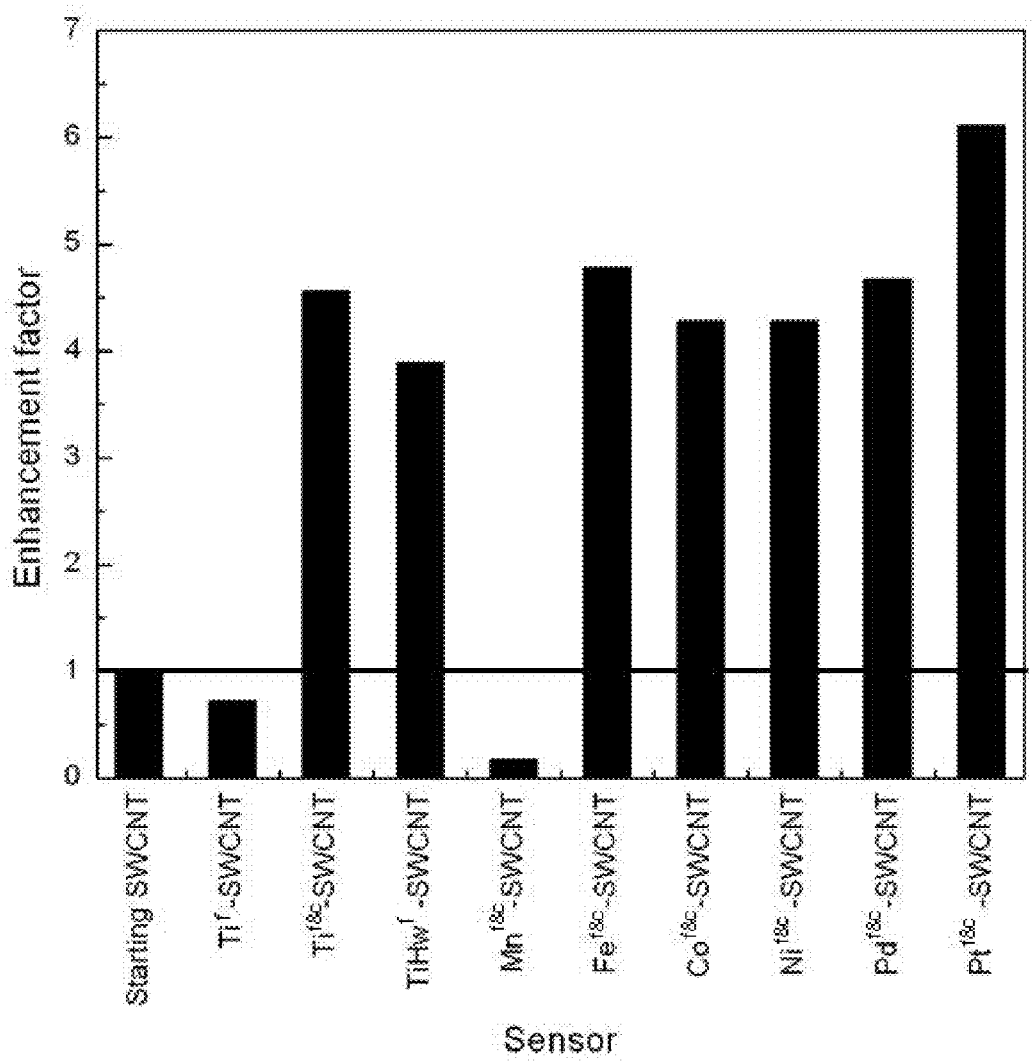
FIG. 29 shows the sensor enhancement factors calculated from Resistive Response (Circuit) of the sensors in the hydrogen concentration range of 0 ppm to 50 ppm (0% to 0.005%).

As shown in FIG. 29, the $Pt^{f\&c}$-SWCNT, $Fe^{f\&c}$-SWCNT, $Pd^{f\&c}$-SWCNT, $Ti^{f\&c}$-SWCNT, $Ni^{f\&c}$-SWCNT, $Co^{f\&c}$-SWCNT and $TiH_w^f$-SWCNT sensors exhibited at least about three-fold enhancement in sensitivity to hydrogen detection over that of the Starting SWCNT sensor.

The minimum detection limits, as shown in Table 6, varied from sensor to sensor. For example, the minimum detection limit for the $Fe^{f\&c}$-SWCNT sensor was about 0.159 ppm of hydrogen at about 1 ohm. While the Starting SWCNT sensor produced a minimum detection limit at about 1.61 ppm of hydrogen, the minimum detection limits of the $Fe^{f\&c}$-SWCNT and $Pt^{f\&c}$-SWCNT sensors were lower than 1 ppm.

TABLE 6

Resistive Sensitivities (Circuit) of the sensors at two different hydrogen concentration ranges.

| Sensor | Resistive Sensitivity (Circuit) (% ppm$^{-1}$) | | Minimum detection limit (ppm) |
|---|---|---|---|
| | Low Concentration Range (0-50 ppm hydrogen) | High Concentration Range (1-3% hydrogen) | |
| $Pt^{f\&c}$ SWCNT | 0.110 | 7.9 × 10$^{-5}$ | 0.714 |
| $Fe^{f\&c}$ SWCNT | 0.086 | 2.0 × 10$^{-6}$ | 0.159 |
| $Pd^{f\&c}$ SWCNT | 0.084 | 8.7 × 10$^{-6}$ | 3.03 |
| $Ti^{f\&c}$ SWCNT | 0.082 | 3.0 × 10$^{-6}$ | 3.57 |
| $Ni^{f\&c}$ SWCNT | 0.077 | 4.1 × 10$^{-5}$ | 3.33 |
| $Co^{f\&c}$ SWCNT | 0.077 | 4.0 × 10$^{-6}$ | 2.70 |
| $TiH_w^f$ SWCNT | 0.070 | 1.6 × 10$^{-6}$ | 2.78 |
| $Ti^f$ SWCNT | 0.013 | 2.6 × 10$^{-5}$ | 1.43 |
| $Mn^{f\&c}$ SWCNT | 0.003 | 1.8 × 10$^{-6}$ | 5.56 |
| Starting SWCNT | 0.018 | 1.4 × 10$^{-5}$ | 1.61 |

Above results indicated that the SWCNT sensors comprising Pt, Fe, Pd, Ti, Co, Ni, or mixtures (or alloys) thereof, with the exception of the $Ti^f$-SWCNT sensor, may particularly be suitable for detection and quantification of hydrogen at concentrations above the minimum detection limits of these sensors.

Example 17

Sensor Comprising Pt Filled and Coated SWCNT Article for Detection or Quantification of Carbon Dioxide A $Pt^{f\&c}$-SWCNT sensor and a Starting SWCNT sensor were prepared and analyzed in the same manner as described in above examples, except the following. The analyte gas in this example was carbon dioxide.

For sensor impedance measurements in carbon dioxide as an analyte gas, the parent carbon dioxide (about 1000 ppm in nitrogen) was diluted with the ultra-high purity $N_2$ to yield concentrations of carbon dioxide varying in the range of 1 ppm to 1000 ppm.

It was found that $R_1$, the uncompensated ohmic resistance of the sensor, did not show any dependence to the carbon dioxide concentration. That is, the contribution of $R_1$ to the Resistive Response (Circuit) was less than 0.03% when the response was averaged in the carbon dioxide concentration range of 1 ppm to 100 ppm. Likewise, the parameter $C_2$, representing the capacitance of the sensor, did not exhibit any meaningful dependence on adsorbed carbon dioxide concentration. That is, in the concentrations ranging from 1 to 100 ppm, the average Capacitive Response (Circuit) was less than 1%. It was thereby concluded that the Electronic Property Responses, $R_1$ and $C_2$ are not suitable for detection or quantification of the carbon dioxide with the $Pt^{f\&c}$-SWCNT sensor.

Figure 30:
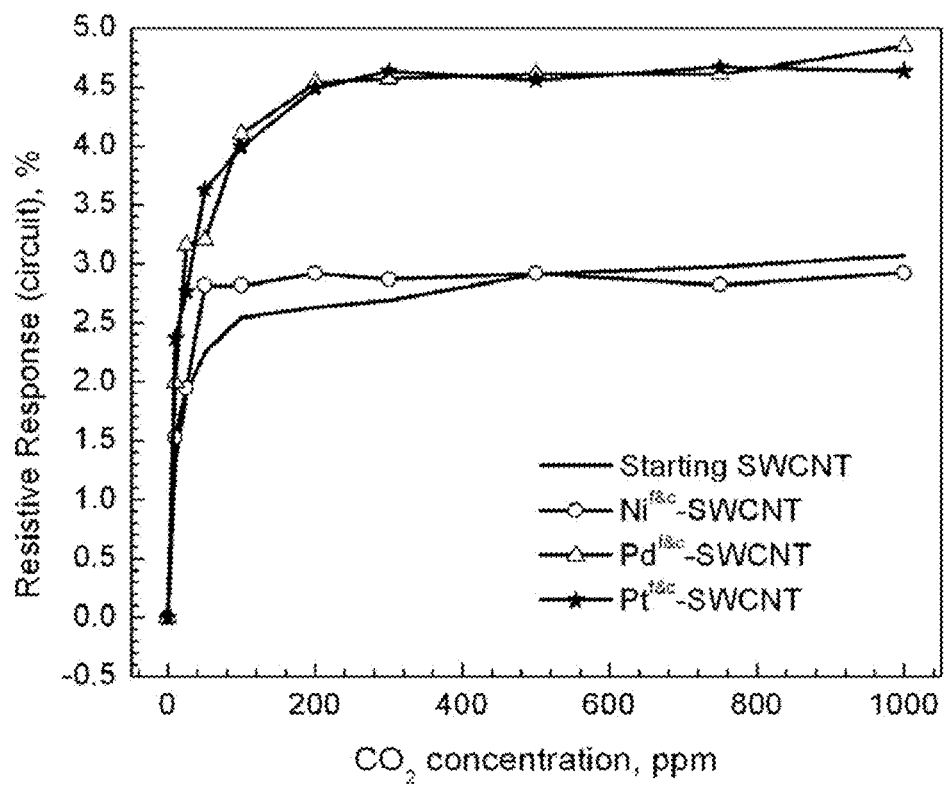
FIG. 30 shows the Resistive Response (Circuit) of the $Ni^{f\&c}$-SWCNT sensor, $Pd^{f\&c}$-SWCNT sensor, $Pt^{f\&c}$-SWCNT sensor and the Starting SWCNT sensor as a function of carbon dioxide concentration.
Figure 31:
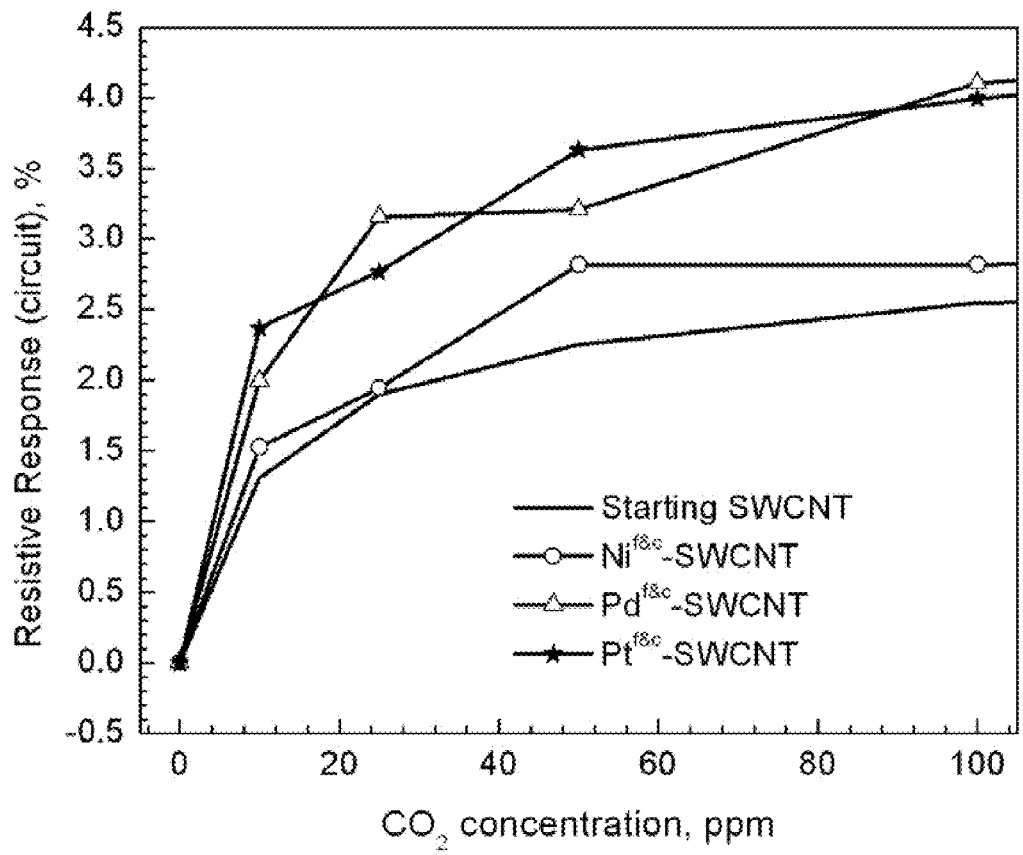
FIG. 31 shows the Resistive Response (Circuit) of the $Ni^{f\&c}$-SWCNT sensor, $Pd^{f\&c}$-SWCNT sensor, $Pt^{f\&c}$-SWCNT sensor and the Starting SWCNT sensor as a function of carbon dioxide concentration in the range of 0 ppm to 100 ppm.
Figure 32:
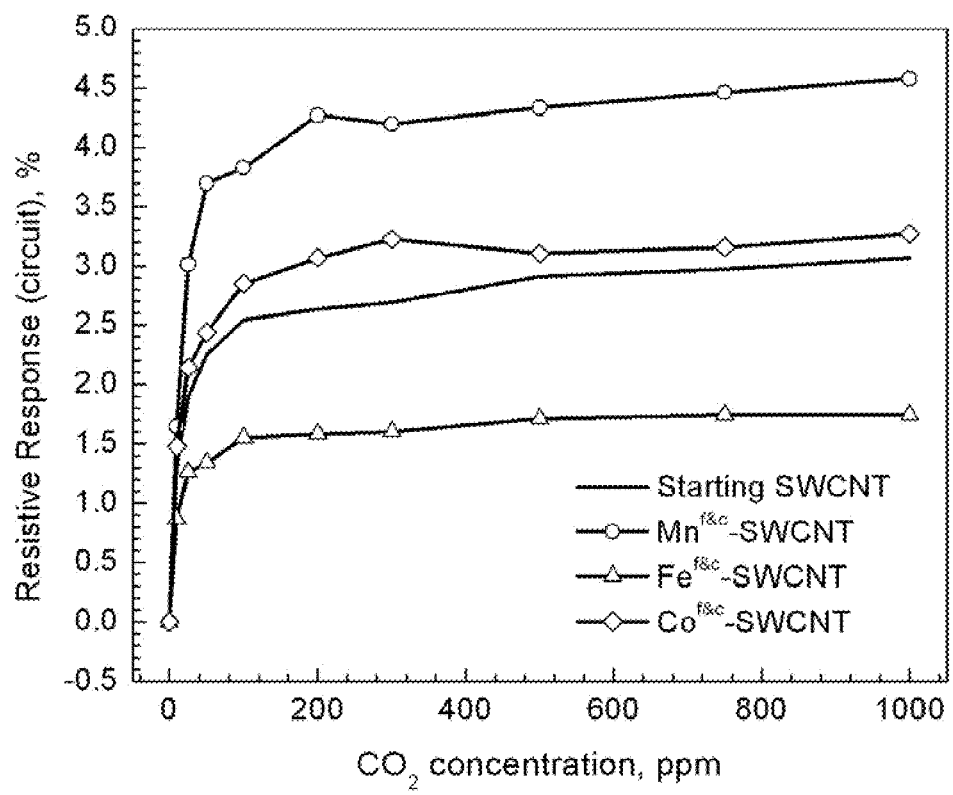
FIG. 32 shows the Resistive Response (Circuit) of the $Mn^{f\&c}$-SWCNT, $Fe^{f\&c}$-SWCNT, $Co^{f\&c}$-SWCNT and the Starting SWCNT sensor as a function of carbon dioxide concentration.
Figure 33:
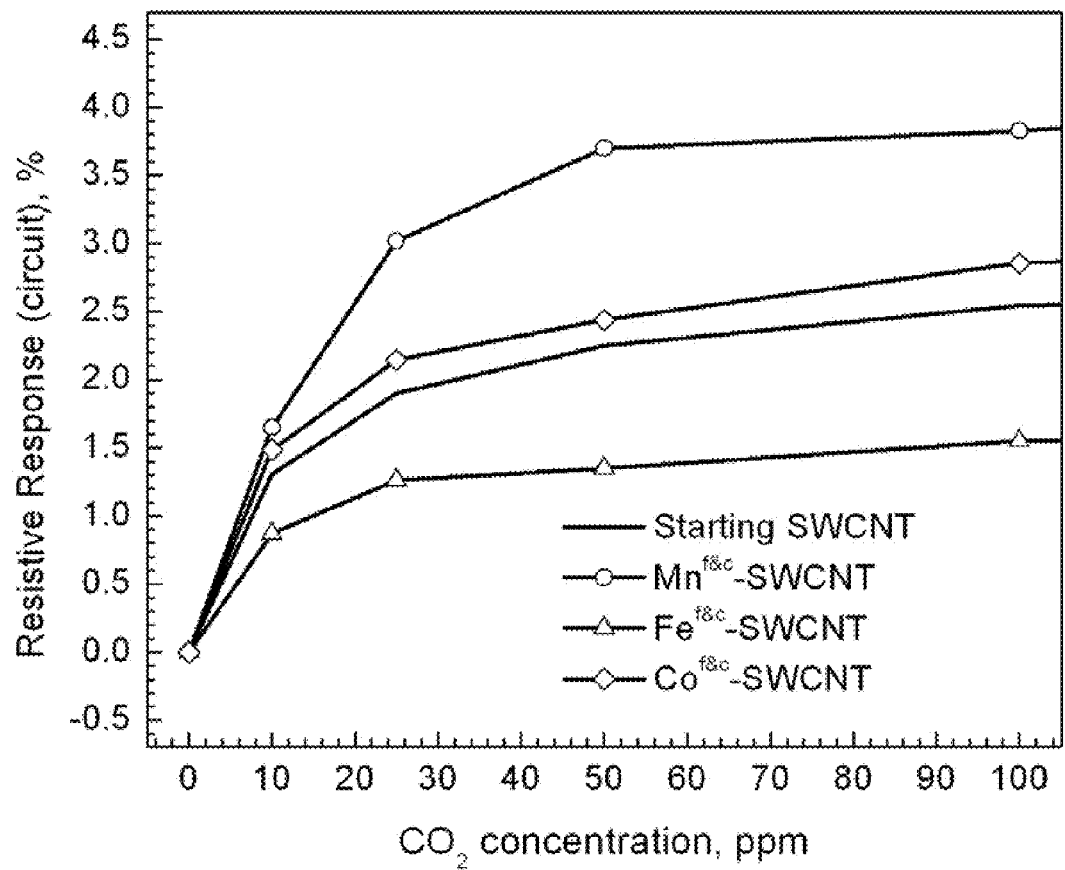
FIG. 33 shows the Resistive Response (Circuit) of the $Mn^{f\&c}$-SWCNT, $Fe^{f\&c}$-SWCNT, $Co^{f\&c}$-SWCNT and the Starting SWCNT sensor as a function of carbon dioxide concentration in the range of 0 ppm to 100 ppm.
Figure 34:
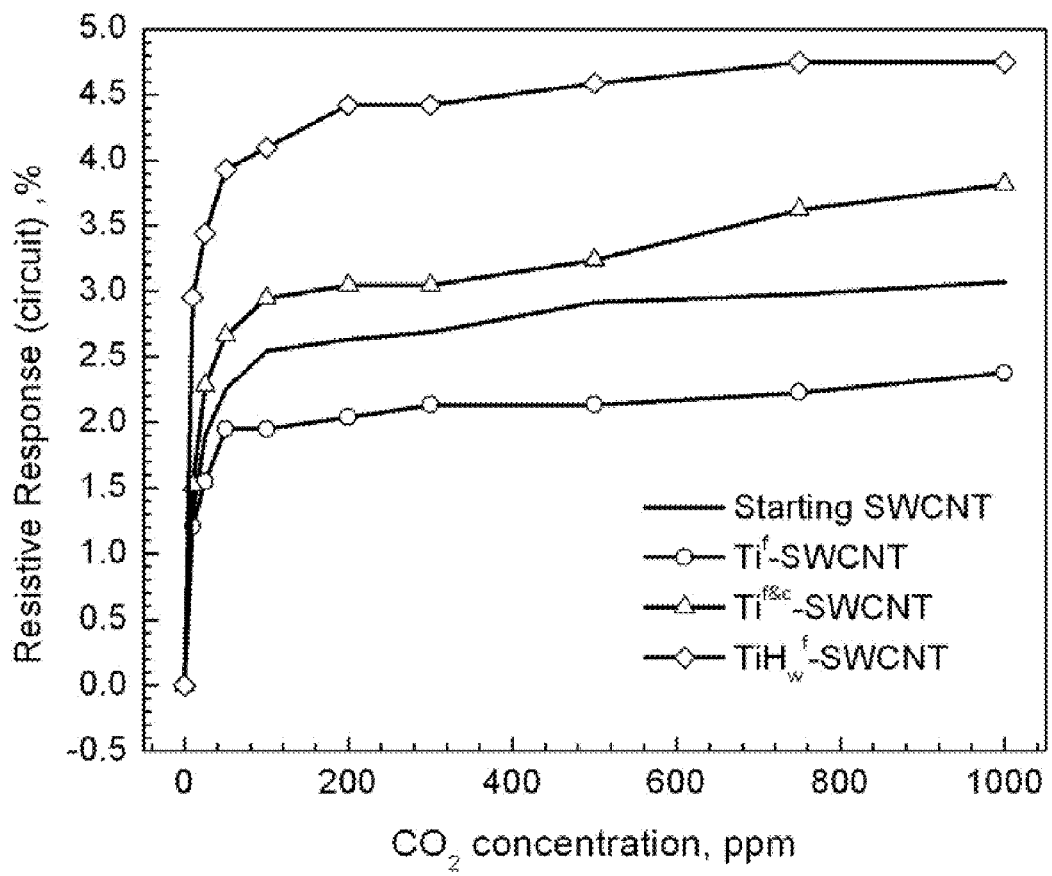
FIG. 34 shows the Resistive Response (Circuit) of the $Ti^f$-SWCNT sensor, $Ti^{f\&c}$-SWCNT sensor, $TiH_w^f$-SWCNT sensor and the Starting SWCNT sensor as a function of carbon dioxide concentration.
Figure 35:
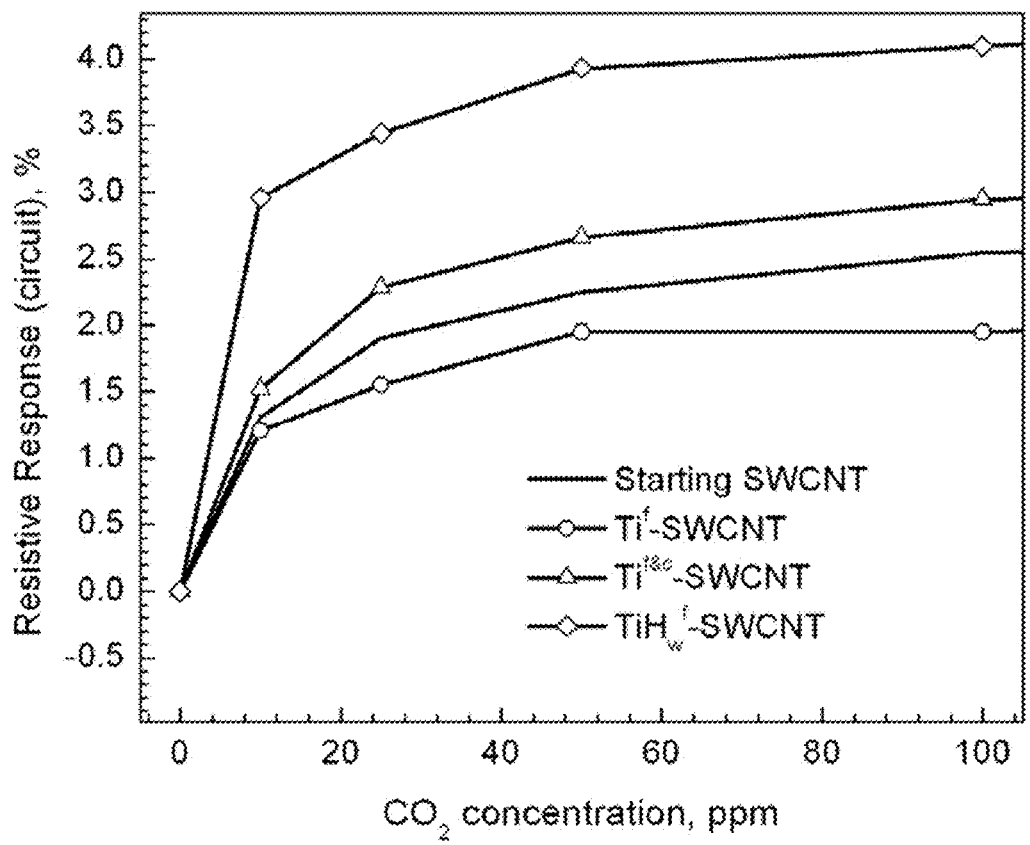
FIG. 35 shows the Resistive Response (Circuit) of the $Ti^f$-SWCNT sensor, $Ti^{f\&c}$-SWCNT sensor, $TiH_w^f$-SWCNT sensor and the Starting SWCNT sensor as a function of carbon dioxide concentration in the range of 0 ppm to 100 ppm.

The other circuit parameter $R_2$, showing the only observable response, increased in the presence of increasing carbon dioxide. The variation of the Resistive Response (Circuit) of the sensor as a function of carbon dioxide concentration, derived from $R_2$, is shown in FIGS. 30 and 31.

Same impedance measurements were repeated for the Starting SWCNT sensor. As shown in FIG. 30, the Resistive Response of the Starting SWCNT sensor was less than 3.2% for all carbon dioxide concentrations.

As compared to this sensor, the $Pt^{f\&c}$-SWCNT sensor showed considerably higher responses to all carbon dioxide concentrations. These results indicated that the incorporation of a non-carbon material to the carbon not only significantly improved the response of the sensor, but also made such sensors viable alternatives to commercially existing sensors.

Example 18

Sensors for Detection and Quantification of Carbon Dioxide

Various sensors were prepared and analyzed in the same manner as described in above examples, except the following. The analyte gas was carbon dioxide.

It was found that $R_1$, the uncompensated ohmic resistance of these sensors, did not show any dependence to the carbon dioxide concentration. That is, the contribution of $R_1$ to the Resistive Response (Circuit) was less than 0.03% when the response was averaged in the carbon dioxide concentration range of 1 ppm to 100 ppm. Likewise, the parameter $C_2$, representing the capacitance of the sensor, did not exhibit any meaningful dependence on adsorbed carbon dioxide concentration, except for the $Ti^{f\&c}$-SWCNT sensor. That is, in the concentration range of 1 ppm to 100 ppm, the Capacitive Response (Circuit) was less than 1% when the response was averaged for this concentration range. It was thereby concluded that the Electronic Property Responses, $R_1$ and $C_2$ are not suitable for detection or quantification of the carbon dioxide with these sensors, except with the $Ti^{f\&c}$-SWCNT sensor.

The other circuit parameter $R_2$, showing the only observable response, increased in the presence of increasing carbon dioxide for some sensors. The variation of the Resistive Response (Circuit) of these sensors, derived from $R_2$, as a function of carbon dioxide concentration is shown in FIGS. 30 to 35. The $Pt^{f\&c}$-SWCNT, $Pd^{f\&c}$-SWCNT, $Mn^{f\&c}$-SWCNT, $Co^{f\&c}$-SWCNT, $Ti^{f\&c}$-SWCNT, and $TiH_w^f$-

SWCNT sensors showed higher Resistive Responses than that of the Starting SWCNT sensor for all carbon dioxide concentrations investigated. The $Ni^{f\&c}$-SWCNT sensor showed higher Resistive Responses than that of the Starting SWCNT sensor up to about 400 ppm carbon dioxide concentration. However, the $Ti^f$-SWCNT and $Fe^{f\&c}$-SWCNT sensors showed lower Resistive Responses than that of the Starting SWCNT sensor.

Figure 36:
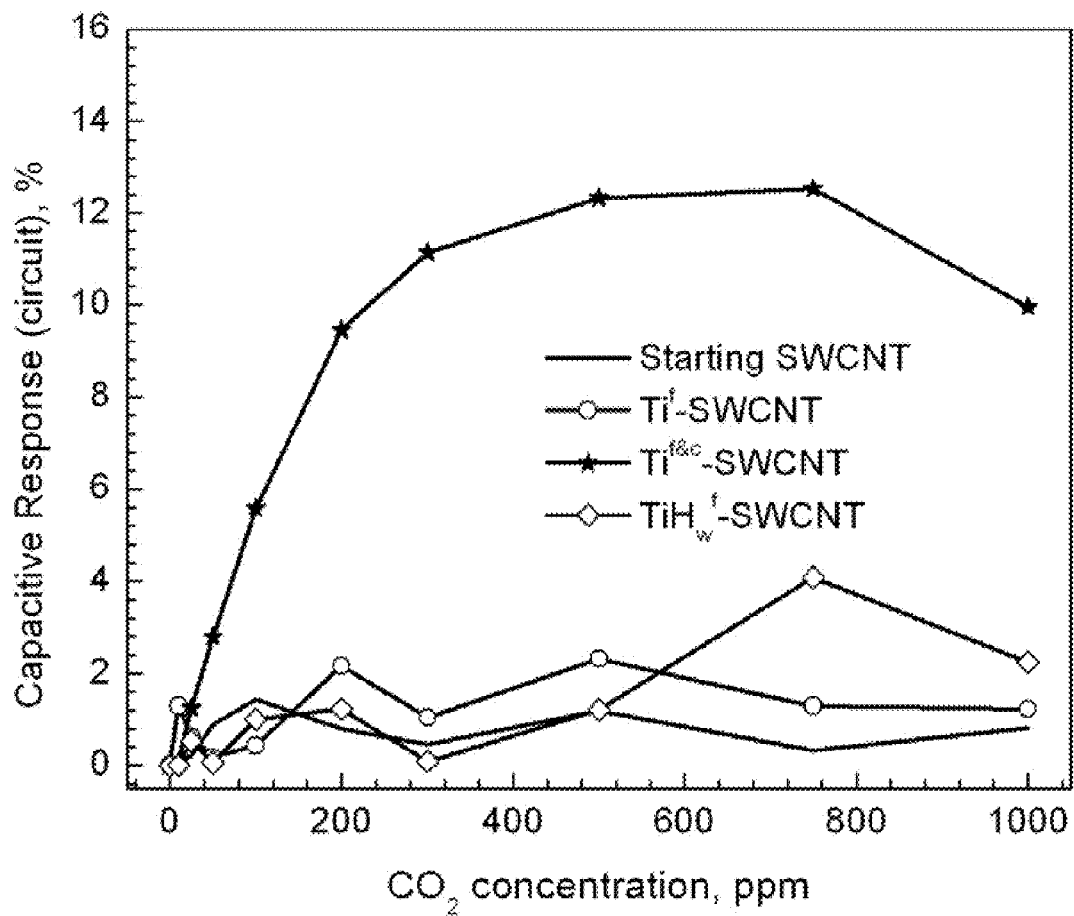
FIG. 36 shows the Capacitive Response (Circuit) of the $Ti^f$-SWCNT sensor, $Ti^{f\&c}$-SWCNT sensor, $TiH_w^f$-SWCNT sensor and the Starting SWCNT sensor as a function of carbon dioxide concentration.

Moreover, the $Ti^{f\&c}$-SWCNT sensor, as shown in FIG. 36, had an observable $C_2$ response, i.e. Capacitive Response (Circuit). It reached as high as 12.5%. Therefore, a device comprising the $Ti^{f\&c}$-SWCNT sensor and the analysis unit that measures the Capacitive Response (Circuit) are within the scope of this invention for detection or quantification of the carbon dioxide.

The calculated sensitivities, derived from $R_2$, are summarized in Table 7. The results showed that the $Pt^{f\&c}$-SWCNT, $Pd^{f\&c}$-SWCNT, $Mn^{f\&c}$-SWCNT, $Ni^{f\&c}$-SWCNT, $Co^{f\&c}$-SWCNT, $Ti^{f\&c}$-SWCNT, and $TiH_w^f$-SWCNT sensors had sensitivities higher than that of the Starting SWCNT sensor for carbon dioxide concentrations at about or below 10 ppm. These results, however, further showed that the $Ti^f$-SWCNT and $Fe^{f\&c}$-SWCNT sensors had lower sensitivities than the Starting SWCNT sensor.

TABLE 7

Resistive Sensitivities (Circuit) of the sensors at two different carbon dioxide concentration ranges.

| Sensor | Resistive Sensitivity (Circuit) (% ppm$^{-1}$) | | Minimum detection limit (ppm) |
|---|---|---|---|
| | Low Concentration Range (0-10 ppm $CO_2$) | High Concentration Range (100-1000 ppm $CO_2$) | |
| $TiH_w^f$ SWCNT | 0.30 | 7.0 × 10$^{-4}$ | 1.10 |
| $Pt^{f\&c}$ SWCNT | 0.24 | 7.0 × 10$^{-4}$ | 0.31 |
| $Pd^{f\&c}$ SWCNT | 0.20 | 8.0 × 10$^{-4}$ | 0.39 |
| $Mn^{f\&c}$ SWCNT | 0.17 | 8.0 × 10$^{-4}$ | 1.18 |
| $Ti^{f\&c}$ SWCNT | 0.15 | 1.0 × 10$^{-3}$ | 2.50 |
| $Ni^{f\&c}$ SWCNT | 0.15 | 1.0 × 10$^{-4}$ | 0.66 |
| $Co^{f\&c}$ SWCNT | 0.14 | 5.0 × 10$^{-4}$ | 0.87 |
| $Ti^f$ SWCNT | 0.12 | 5.0 × 10$^{-4}$ | 1.50 |
| $Fe^{f\&c}$ SWCNT | 0.08 | 2.0 × 10$^{-4}$ | 0.05 |
| Starting SWCNT | 0.13 | 6.0 × 10$^{-4}$ | 0.90 |

Figure 37:
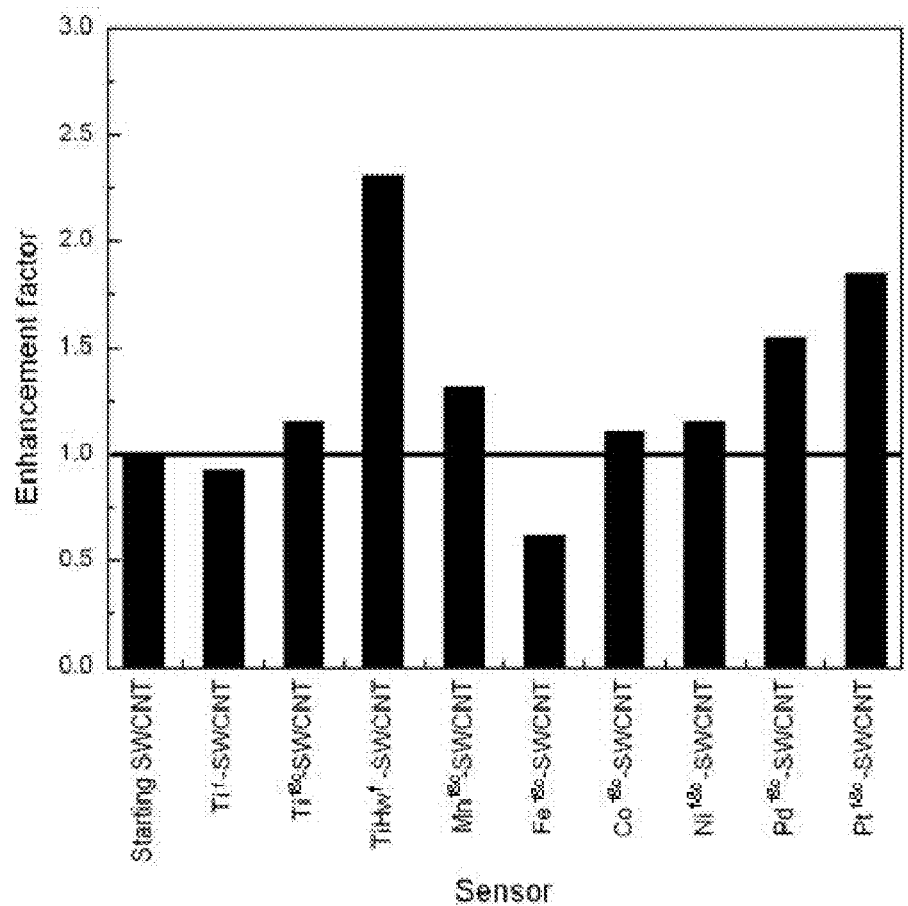
FIG. 37 shows the sensor enhancement factors calculated from Resistive Response (Circuit) sensitivities in the carbon dioxide concentration range of 0 ppm to 10 ppm.

As shown in FIG. 37, the $Pt^{f\&c}$-SWCNT, $Pd^{f\&c}$-SWCNT, $Mn^{f\&c}$-SWCNT, $Ni^{f\&c}$-SWCNT, $Co^{f\&c}$-SWCNT, $Ti^{f\&c}$-SWCNT, and $TiH_w^f$-SWCNT sensors exhibited enhanced sensitivity to carbon dioxide detection over that of the Starting SWCNT sensor.

The minimum detection limits, as shown in Table 7, varied from sensor to sensor. For example, the minimum detectable signal for the $Fe^{f\&c}$-SWCNT sensor was about 0.05 ppm of carbon dioxide at about 1 ohm. While the Starting SWCNT sensor produced a minimum detectable signal at about 0.90 ppm of carbon dioxide, the detection limits of the $Fe^{f\&c}$-SWCNT, $Pd^{f\&c}$SWCNT, $Ni^{f\&c}$SWCNT, $Co^{f\&c}$SWCNT and $Pt^{f\&c}$-SWCNT sensors were lower than 0.90 ppm.

The above results indicated that the SWCNT sensors comprising Pt, Pd, Ti, Co, Ni, Mn, or mixtures (or alloys) thereof, with the exception of the $Ti^f$-SWCNT and $Fe^{f\&c}$-SWCNT sensors, may particularly be suitable for detection and quantification of carbon dioxide at concentrations above the minimum detection limits of these sensors.

Example 19

Sensor Comprising Pt Filled and Coated SWCNT Article for Detection or Quantification of Oxygen A $Pt^{f\&c}$-SWCNT sensor and a Starting SWCNT sensor were prepared and analyzed in the same manner as described in above examples, except the following. The analyte gas in this example was oxygen.

For sensor impedance measurements in oxygen as an analyte gas, the parent oxygen (about 1000 ppm in nitrogen) was diluted with the ultra-high purity $N_2$ to yield concentrations of oxygen varying in the range of 1 ppm to 1000 ppm.

It was found that $R_1$, the uncompensated ohmic resistance of the sensor, did not show any dependence to the oxygen concentration. That is, the contribution of $R_1$ to the Resistive Response (Circuit) was less than 0.03% when the response was averaged in the oxygen concentration range of 1 ppm to 100 ppm. It was thereby concluded that the Electronic Property Response $R_1$ is not suitable for detection or quantification of the oxygen with the $Pt^{f\&c}$-SWCNT sensor.

Figure 38:
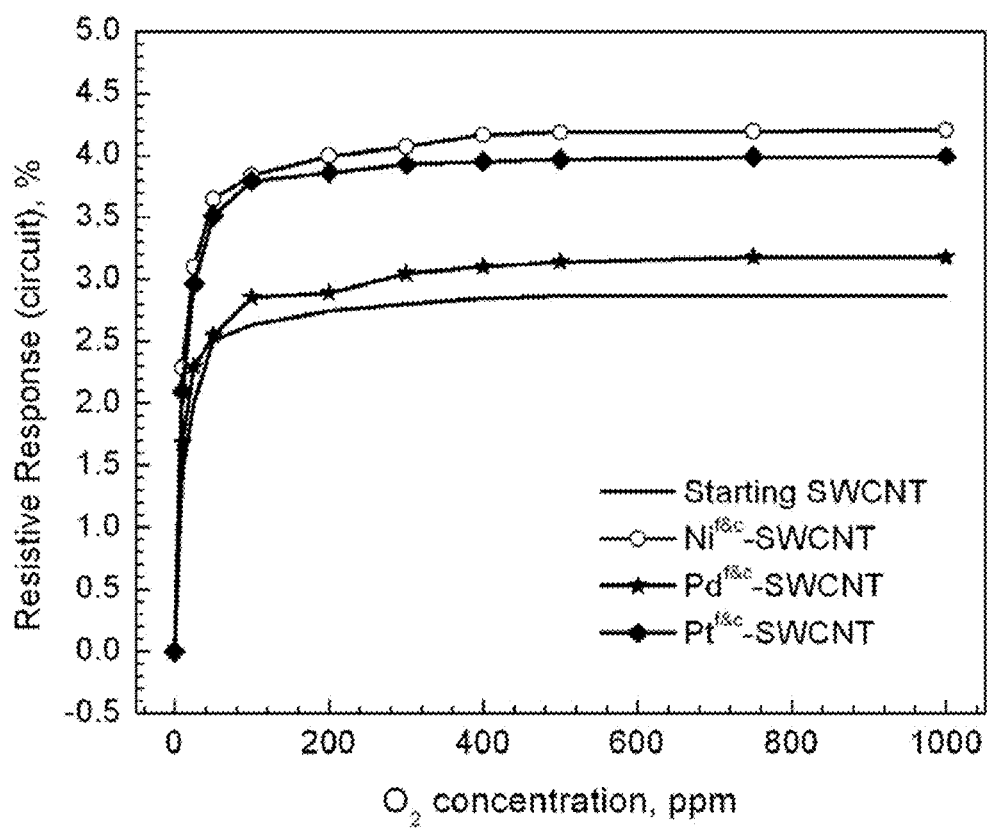
FIG. 38 shows the Resistive Response (Circuit) of the $Ni^{f\&c}$-SWCNT sensor, $Pd^{f\&c}$-SWCNT sensor, $Pt^{f\&c}$-SWCNT sensor and the Starting SWCNT sensor as a function of oxygen concentration.
Figure 39:
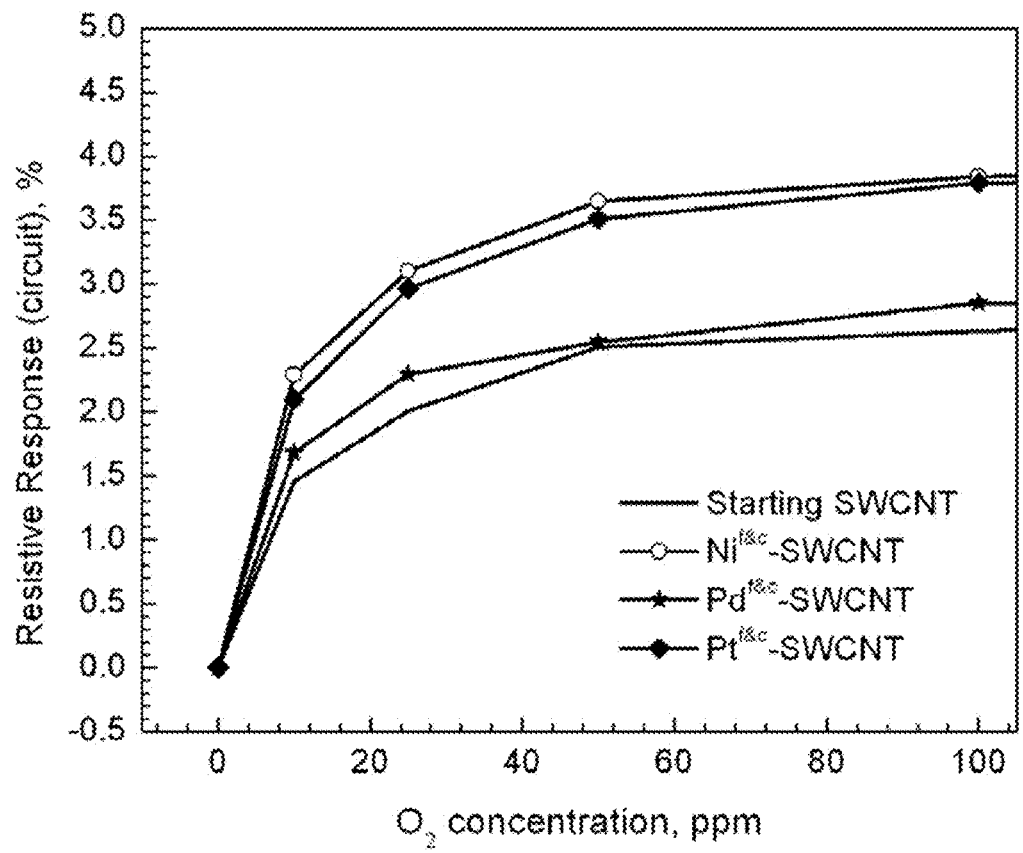
FIG. 39 shows the Resistive Response (Circuit) of the $Ni^{f\&c}$-SWCNT sensor, $Pd^{f\&c}$-SWCNT sensor, $Pt^{f\&c}$-SWCNT sensor and the Starting SWCNT sensor as a function of oxygen concentration in the range of 0 ppm to 100 ppm.
Figure 40:
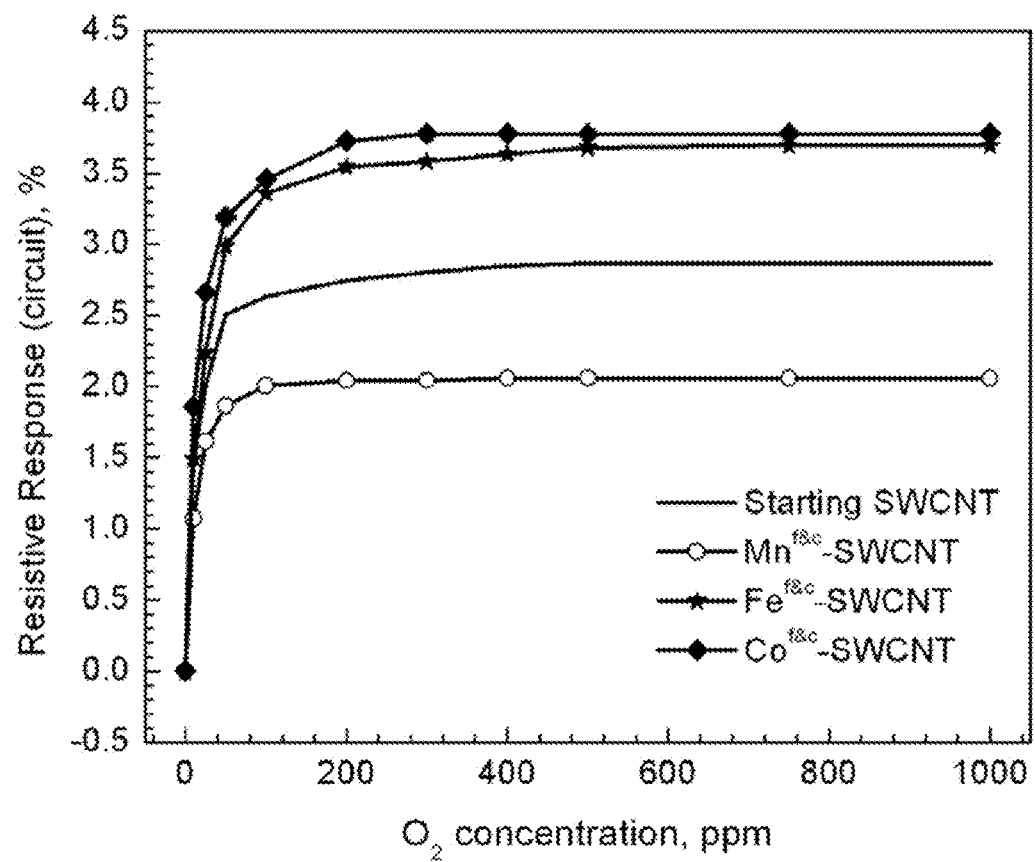
FIG. 40 shows the Resistive Response (Circuit) of the $Mn^{f\&c}$-SWCNT, $Fe^{f\&c}$-SWCNT, $Co^{f\&c}$-SWCNT and the Starting SWCNT sensor as a function of oxygen concentration.
Figure 41:
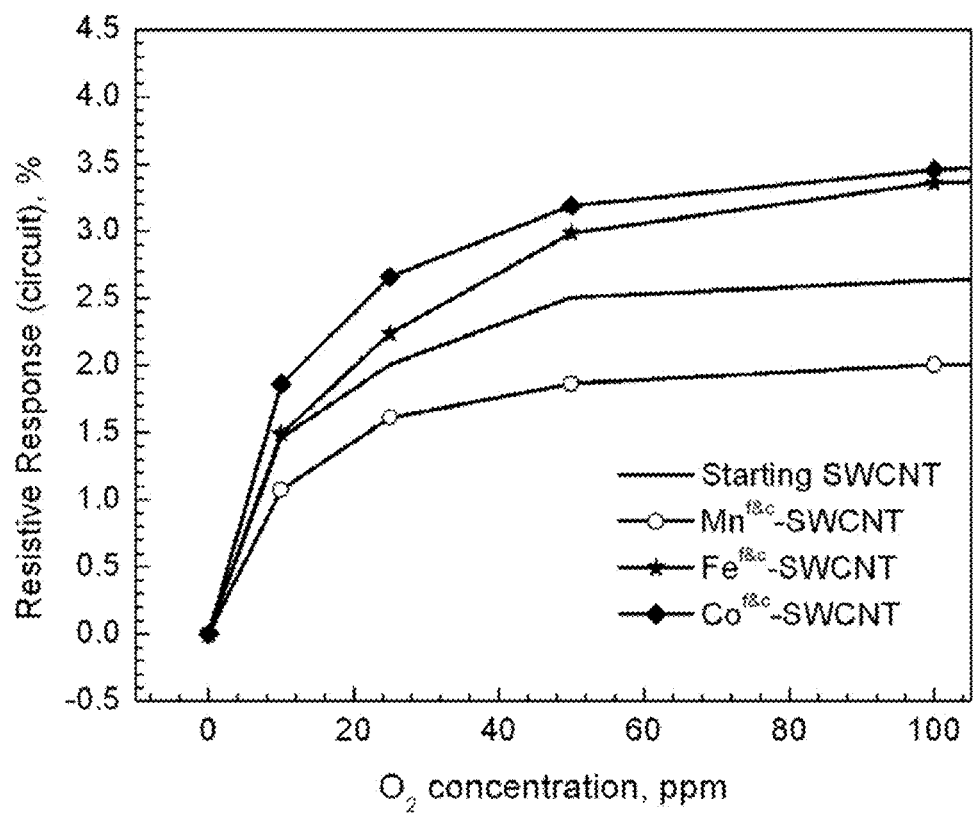
FIG. 41 shows the Resistive Response (Circuit) of the $Mn^{f\&c}$-SWCNT, $Fe^{f\&c}$-SWCNT, $Co^{f\&c}$-SWCNT and the Starting SWCNT sensor as a function of oxygen concentration in the range of 0 ppm to 100 ppm.
Figure 42:
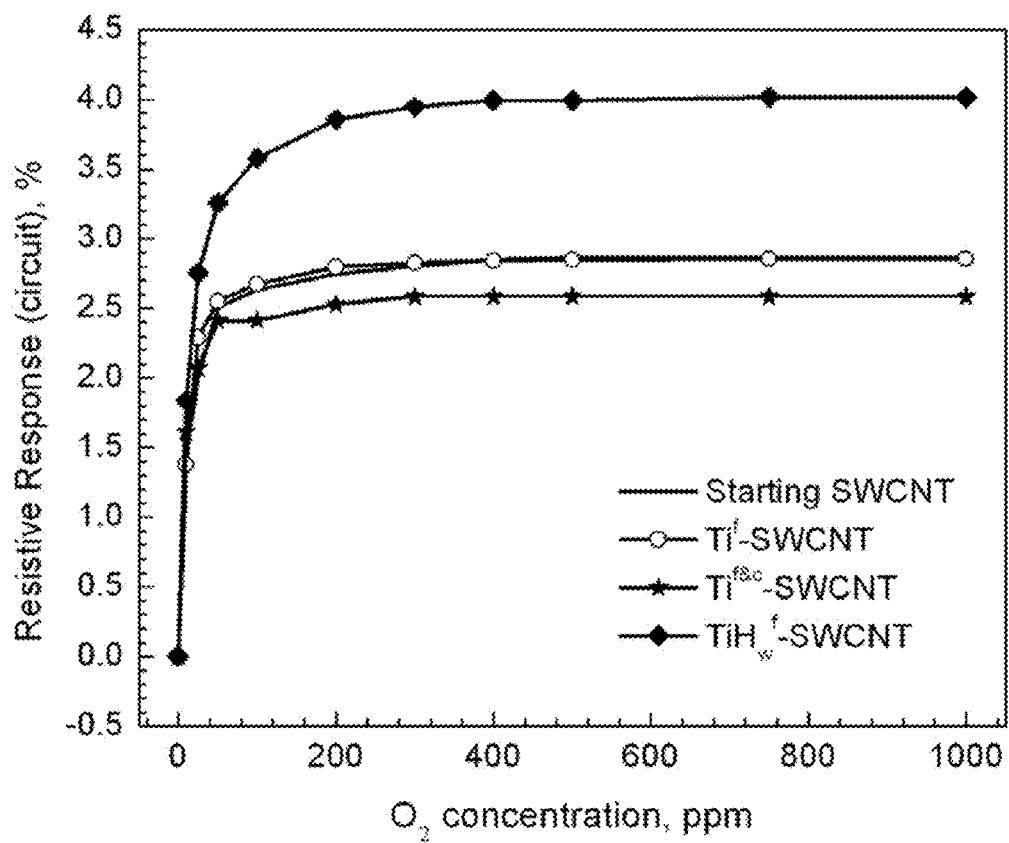
FIG. 42 shows the Resistive Response (Circuit) of the $Ti^f$-SWCNT sensor, $Ti^{f\&c}$-SWCNT sensor, $TiH_w^f$-SWCNT sensor and the Starting SWCNT sensor as a function of oxygen concentration.
Figure 43:
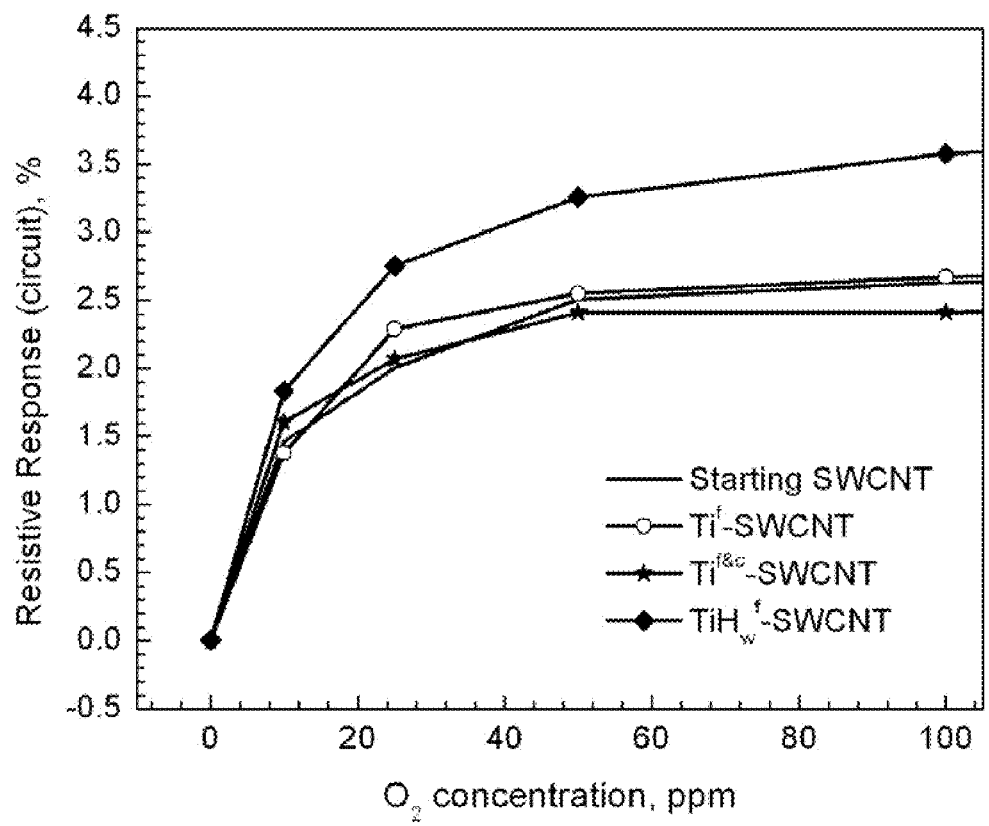
FIG. 43 shows the Resistive Response (Circuit) of the $Ti^f$-SWCNT sensor, $Ti^{f\&c}$-SWCNT sensor, $TiH_w^f$-SWCNT sensor and the Starting SWCNT sensor as a function of oxygen concentration in the range of 0 ppm to 100 ppm.

The other circuit parameters $R_2$ and $C_2$ increased in the presence of oxygen. The variation of the Resistive Response (Circuit) of the sensor, derived from $R_2$, as a function of oxygen concentration is shown in FIGS. 38 and 39.

Same impedance measurements were repeated for the Starting SWCNT sensor. As shown in FIG. 38, the Resistive Response of the Starting SWCNT sensor was less than 3.0% for all oxygen concentrations. As compared to this sensor, the $Pt^{f\&c}$-SWCNT sensor showed considerably higher responses to all oxygen concentrations.

Figure 44:
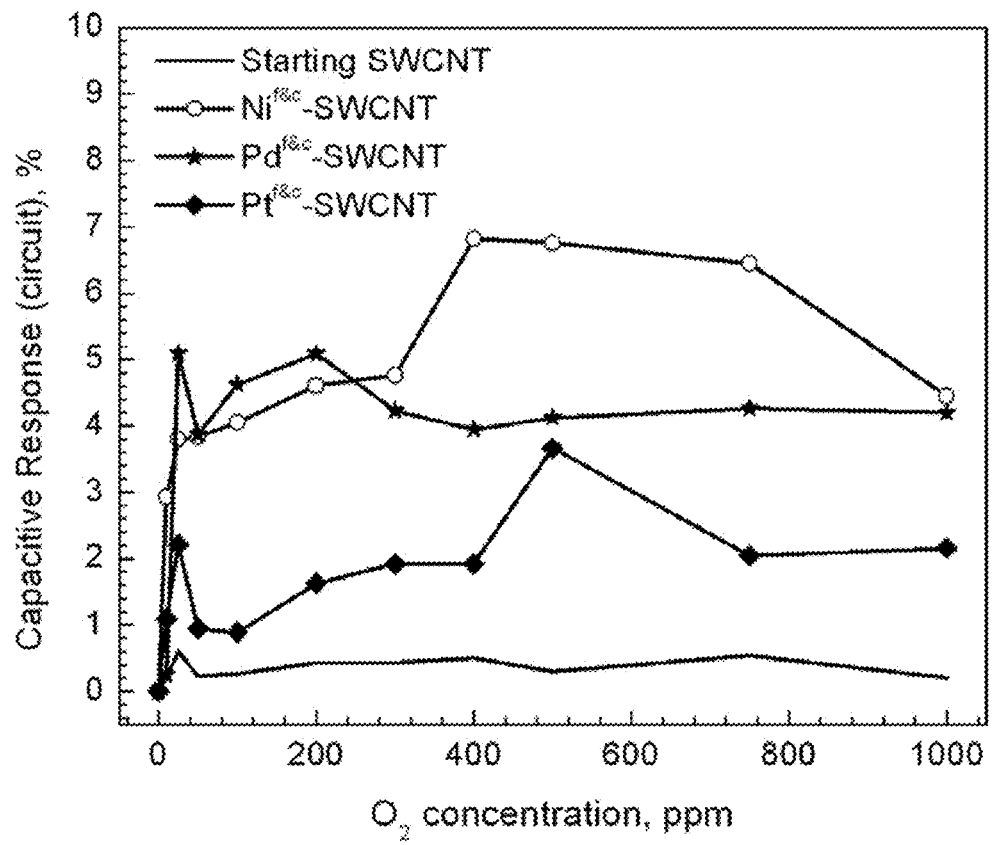
FIG. 44 shows the Capacitive Response (Circuit) of the $Ni^{f\&c}$-SWCNT sensor, $Pd^{f\&c}$-SWCNT sensor, $Pt^{f\&c}$-SWCNT sensor and the Starting SWCNT sensor as a function of oxygen concentration.

The variation of the Capacitive Response (Circuit) of the sensor as a function of oxygen concentration is shown in FIG. 44. Same impedance measurements were repeated for the Starting SWCNT sensor. As shown in FIG. 44, the Capacitive Response of the Starting SWCNT sensor was less than 0.5% for all oxygen concentrations. As compared to this sensor, the $Pt^{f\&c}$-SWCNT sensor showed considerably higher responses to all oxygen concentrations.

These results indicated that the incorporation of a non-carbon material to the carbon not only significantly improved the response of the sensor, but also made such sensors viable alternatives to commercially existing sensors.

Example 20

Sensors for Detection and Quantification of Oxygen

Various sensors were prepared and analyzed in the same manner as described in above examples, except the following. The analyte gas was oxygen.

It was found that $R_1$, the uncompensated ohmic resistance of these sensors, did not show any dependence to the oxygen concentration. That is, the contribution of $R_1$ to the Resistive Response (Circuit) was less than 0.03% when the response was averaged in the oxygen concentration range of 1 ppm to 100 ppm. It was thereby concluded that the Electronic Property Response $R_1$ is not suitable for detection or quantification of the oxygen with these sensors.

The variation of the Resistive Response (Circuit) of these sensors, derived from $R_2$, as a function of oxygen concentration is shown in FIGS. 38 to 43. The $Pt^{f\&c}$-SWCNT, $Pd^{f\&c}$-SWCNT, $Ni^{f\&c}$-SWCNT, $Fe^{f\&c}$-SWCNT, $Co^{f\&c}$-SWCNT, and $TiH_w^f$-SWCNT sensors showed higher resistive responses than the Starting SWCNT sensor for all oxygen concentrations investigated. The $Ti^f$-SWCNT sensor showed similar Resistive Responses to that of the Starting SWCNT sensor over all oxygen concentrations. However, the $Ti^{f\&c}$-SWCNT and $Mn^{f\&c}$-SWCNT sensors showed lower Resistive Responses than that of the Starting SWCNT sensor.

Figure 45:
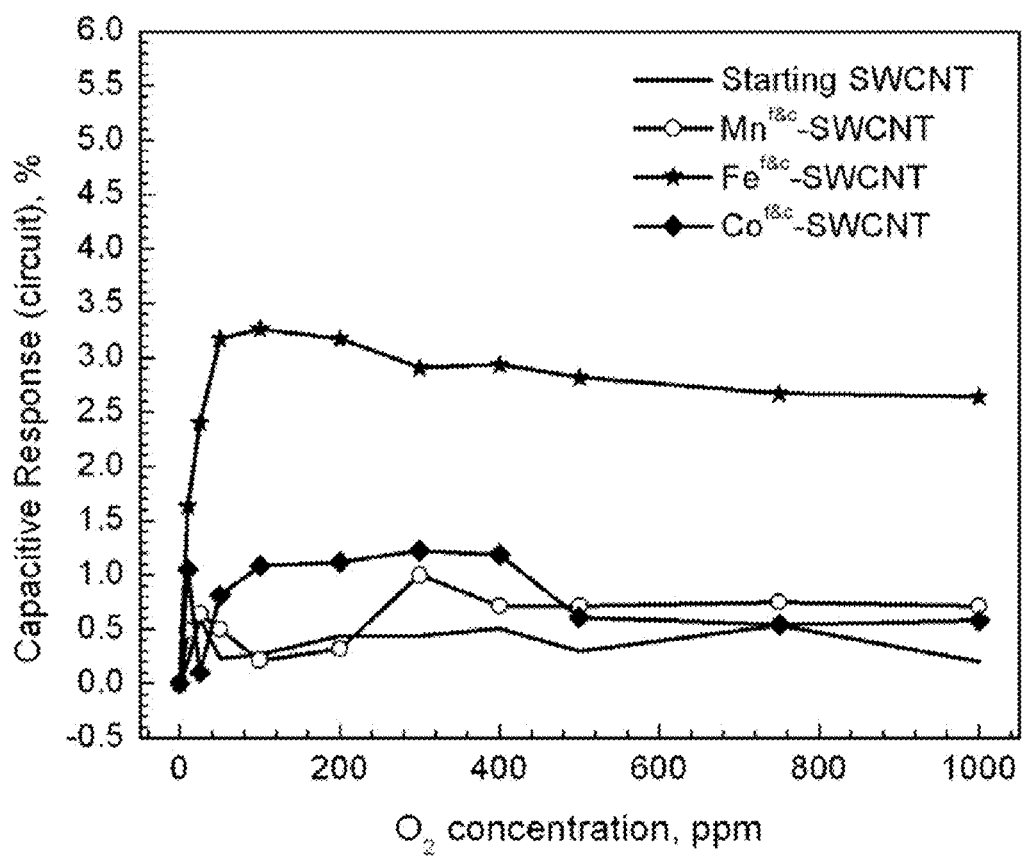
FIG. 45 shows the Capacitive Response (Circuit) of the $Mn^{f\&c}$-SWCNT, $Fe^{f\&c}$-SWCNT, $Co^{f\&c}$-SWCNT and the Starting SWCNT sensor as a function of oxygen concentration.
Figure 46:
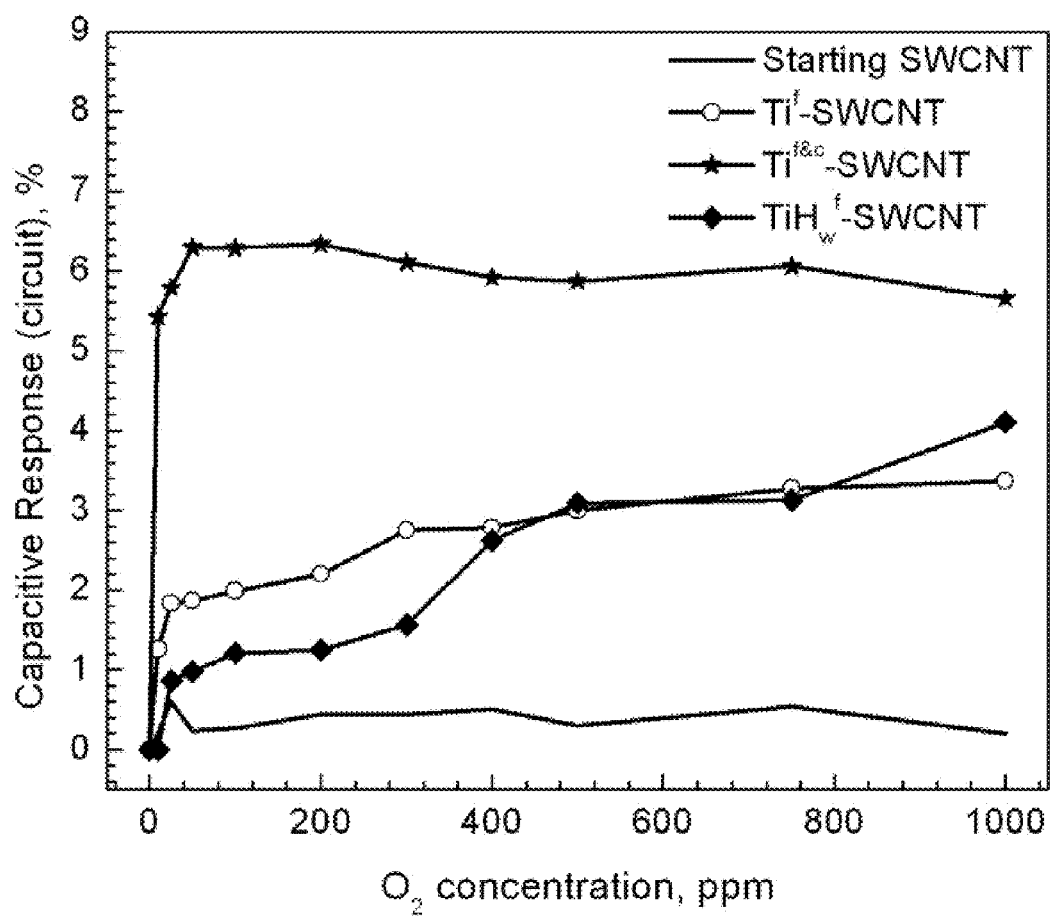
FIG. 46 shows the Capacitive Response (Circuit) of the $Ti^f$-SWCNT sensor, $Ti^{f\&c}$-SWCNT sensor, $TiH_w^f$-SWCNT sensor and the Starting SWCNT sensor as a function of oxygen concentration.

The variation of the Capacitive Response (Circuit) of the sensors as a function of oxygen concentration is shown in FIGS. 44 to 46. All the sensors had an increased Capacitive Response (circuit) to varying oxygen concentration compared to the response of the Starting SWCNT sensor.

The calculated sensitivities, derived from $R_2$ and $C_2$, are summarized in Table 8. The results showed that all non-carbon containing SWCNT sensors had sensitivities higher than that of the Starting SWCNT sensor for oxygen concentrations at about or below 10 ppm.

Figure 47:
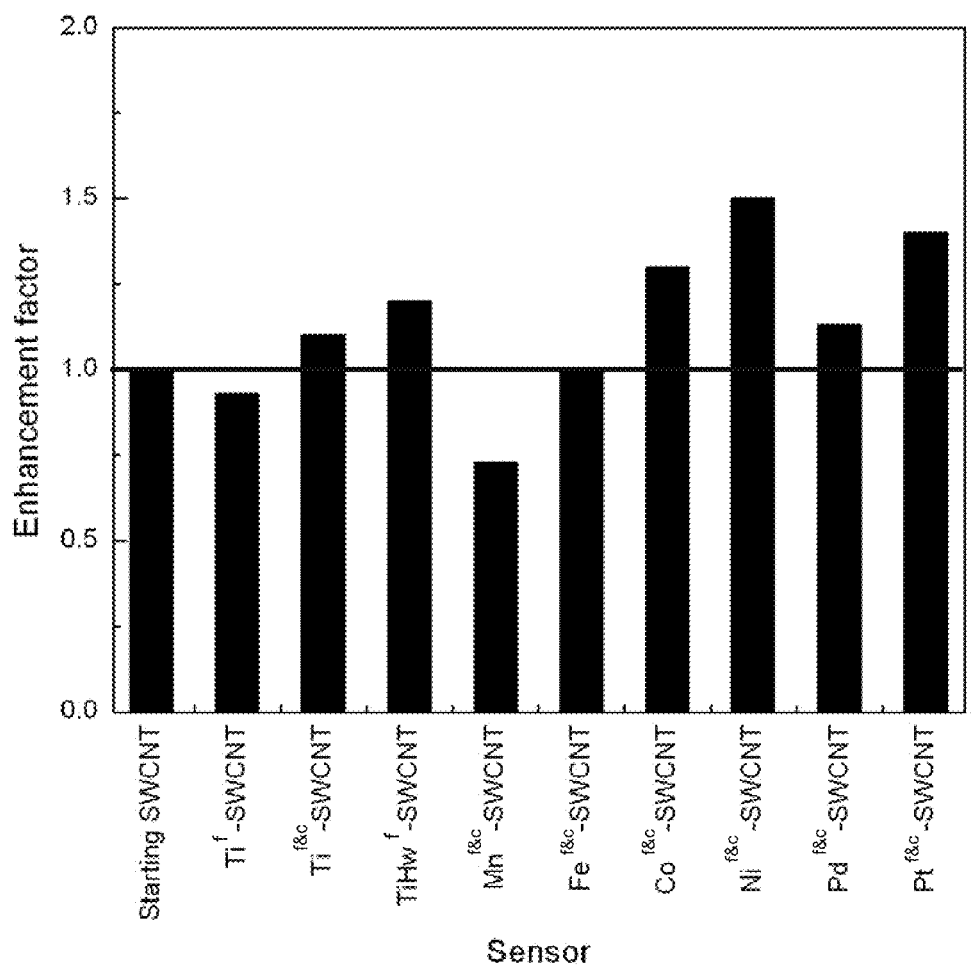
FIG. 47 shows the sensor enhancement factors derived from Resistive Response (Circuit) sensitivities in the oxygen concentration range of 0 ppm to 10 ppm.

The sensor enhancement factors calculated from $R_2$ sensitivities are shown in FIG. 47. The $Pt^{f\&c}$-SWCNT, $Pd^{f\&c}$-SWCNT, $Ni^{f\&c}$-SWCNT, $Co^{f\&c}$-SWCNT, $Ti^{f\&c}$-SWCNT, and $TiH_w^f$-SWCNT sensors exhibited enhanced resistive sensitivity to oxygen detection over that of the Starting SWCNT sensor.

TABLE 8

Resistive and Capacitive Sensitivities of the sensors for oxygen gas.

| Sensor | Resistive Sensitivity (Circuit), (% ppm$^{-1}$) | Capacitive Sensitivity (Circuit), (% ppm$^{-1}$) |
| --- | --- | --- |
| $Ti^f$-SWCNT | 0.14 | 0.12 |
| $Ti^{f\&c}$-SWCNT | 0.16 | 0.55 |
| $Mn^{f\&c}$-SWCNT | 0.18 | 0.05 |
| $Fe^{f\&c}$-SWCNT | 0.11 | 0.16 |
| $Co^{f\&c}$-SWCNT | 0.15 | 0.10 |
| $Ni^{f\&c}$-SWCNT | 0.19 | 0.30 |
| $TiH_w^f$-SWCNT | 0.23 | 0.03 |
| $Pd^{f\&c}$-SWCNT | 0.17 | 0.09 |
| $Pt^{f\&c}$-SWCNT | 0.21 | 0.10 |
| Starting SWCNT | 0.15 | 0.02 |

Table 9 summarizes results of Examples 11-20: the Electronic Property Responses of different sensors to different analyte gases. The $NO_2$ results are summarized from Examples 11-12. The ethanol vapor results are summarized from Examples 13-14. The $H_2$ results are summarized from Examples 15-16. The $CO_2$ results are summarized from Examples 17-18. The $O_2$ results are summarized from Examples 19-20.

TABLE 9

Electronic Property Responses of the sensors to different analytes, when this response is averaged at an analyte concentration range of 1 ppm to 100 ppm.

| Sensor | NO$_2$ Resistive Response | NO$_2$ Resistive Response (Circuit) | NO$_2$ Capacitive Response (Circuit) | Ethanol Vapor Resistive Response (Circuit) | H$_2$ Resistive Response (Circuit) | CO$_2$ Resistive Response (Circuit) | CO$_2$ Capacitive Response (Circuit) | O$_2$ Resistive Response (Circuit) | O$_2$ Capacitive Response (Circuit) |
| --- | --- | --- | --- | --- | --- | --- | --- | --- | --- |
| Starting-SWCNT | ✓ | ✓ | X | X | X | ✓ | X | ✓ | ✓ |
| $Ti^f$-SWCNT | ✓ | ✓ | ✓ | ✓ | X | ✓ | X | ✓ | ✓ |
| $Ti^{f\&c}$-SWCNT | ✓ | ✓ | ✓ | ✓ | ✓ | ✓ | ✓ | ✓ | ✓ |
| $TiH_w^f$-SWCNT | ✓ | ✓ | ✓ | ✓ | ✓ | ✓ | X | ✓ | ✓ |
| $Mn^{f\&c}$-SWCNT | ✓ | ✓ | X | ✓ | X | ✓ | X | ✓ | X |
| $Fe^{f\&c}$-SWCNT | ✓ | ✓ | ✓ | ✓ | ✓ | ✓ | X | ✓ | ✓ |
| $Co^{f\&c}$-SWCNT | ✓ | ✓ | ✓ | ✓ | ✓ | ✓ | X | ✓ | X |
| $Ni^{f\&c}$-SWCNT | ✓ | ✓ | ✓ | X | ✓ | ✓ | X | ✓ | ✓ |
| $Pd^{f\&c}$-SWCNT | ✓ | ✓ | ✓ | ✓ | ✓ | ✓ | X | ✓ | ✓ |
| $Pt^{f\&c}$-SWCNT | ✓ | ✓ | ✓ | ✓ | ✓ | ✓ | X | ✓ | ✓ |

Sensors denoted with the symbol "✓" have Electronic Property Responses equivalent to or higher than 1%.
Sensors denoted with the symbol "X" have Electronic Property Responses lower than 1%.

Example 21

Sensor Array Device for Detection or Quantification of a Gas Mixture Comprising Two Analytes, $NO_2$ and Ethanol Vapor In this example, an array device is constructed for detection or quantification of a gas mixture comprising two analytes, $NO_2$ and ethanol vapor. This device works in the concentration range of 0 ppm to 100 ppm range for each analyte gas. The background gas is nitrogen.

Figure 48:
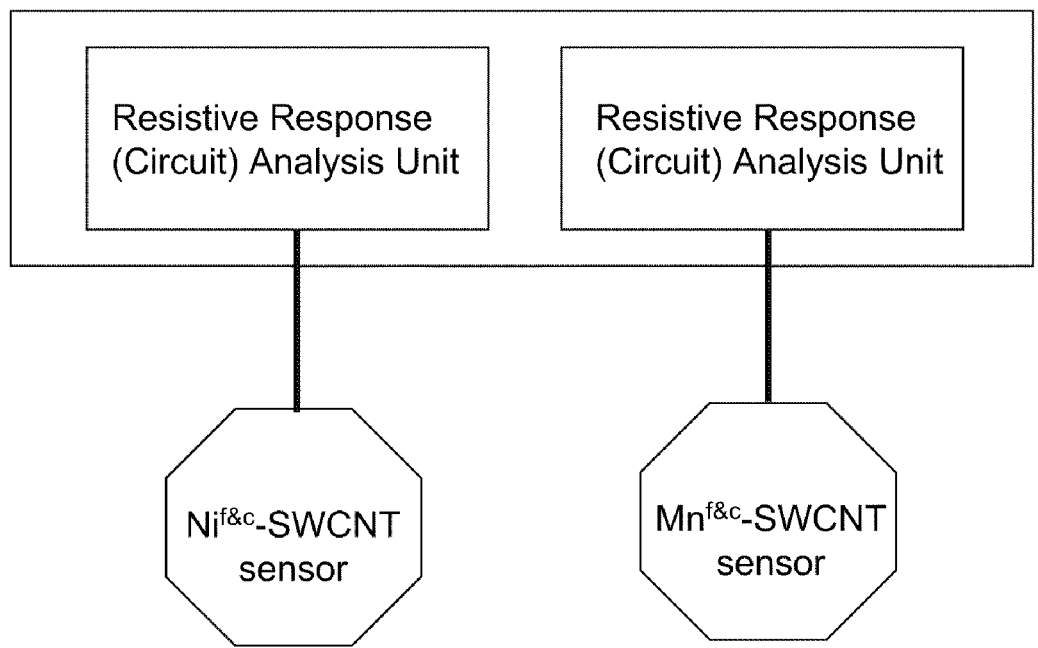
FIG. 48 schematically shows a device comprising a $Ni^{f\&c}$-SWCNT sensor connected to a Resistive Response (Circuit) analysis unit and a $Mn^{f\&c}$-SWCNT sensor connected to a Resistive Response (Circuit) analysis unit.

This array device comprises two sensors: one $Ni^{f\&c}$-SWCNT sensor connected to a Resistive Response (Circuit) analysis unit and one $Mn^{f\&c}$-SWCNT sensor connected to another Resistive Response (Circuit) analysis unit. The construction of such a device is schematically demonstrated in FIG. 48.

As disclosed in Example 12, the $Ni^{f\&c}$-SWCNT sensor had a Resistive Response (Circuit) to $NO_2$ gas. However, as disclosed in Example 14, the average Resistive Response (Circuit) of the $Ni^{f\&c}$-SWCNT sensor was very low, less than 0.53% in the ethanol concentrations ranging from 1 to 100 ppm. Thus, the response of this sensor to ethanol is negligible. Therefore, this sensor may only detect or quantify the $NO_2$ gas, but not the ethanol vapor. In other words, any response of this sensor is due to the $NO_2$ gas.

As disclosed in Example 14, the $Mn^{f\&c}$-SWCNT sensor had a Resistive Response (Circuit) to the ethanol vapor. As also disclosed in Example 12, this sensor also had a Resistive Response (Circuit) to the $NO_2$ gas.

The detection or quantification is carried out as follows. First, the $NO_2$—$N_2$ gas mixture is introduced at various known concentrations. Then, the $Ni^{f\&c}$-SWCNT sensor and the $Mn^{f\&c}$-SWCNT sensor are calibrated and their sensitivity is determined. After this step, the $Mn^{f\&c}$-SWCNT sensor is calibrated and its sensitivity is determined by introducing the ethanol—$N_2$ gas mixture at various known concentrations.

After these calibrations, the gas mixture with unknown analyte gas concentration is introduced. During the quantification, first the unknown concentration of $NO_2$ is determined by using the Resistive Response (Circuit) of the $Ni^{f\&c}$-SWCNT sensor. By using this measured amount, the Resistive Response (Circuit) of the $Mn^{f\&c}$-SWCNT sensor to $NO_2$ gas is calculated.

After this step, the Resistive Response (Circuit) of the $Mn^{f\&c}$-SWCNT sensor is measured. The calculated response of this sensor to $NO_2$ gas is then subtracted from this measurement to yield this sensor's response to the ethanol vapor. The unknown concentration of the ethanol vapor is thereby determined.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. A method for detecting ethanol vapor in a gas mixture, comprising:
   flowing a gas mixture over a sensor comprising a carbon nanotube filled with one or more non-carbon materials comprising titanium, a manganese compound, iron, cobalt, or any combination thereof;
   detecting and determining the concentration of ethanol vapor in the gas mixture by measuring the Electronic Property Response of the sensor due to the ethanol vapor using an analysis unit connected to the sensor.

2. The method according to claim 1, wherein the sensor provides higher Electronic Property Response than a sensor comprising an unfilled carbon nanotube provides.

3. The method according to claim 1, wherein said carbon nanotube is a single wall carbon nanotube or a multi wall carbon nanotube.

4. The method according to claim 3, wherein said carbon nanotube is a single wall carbon nanotube with an outer diameter varying in the range of 1.0 nm to 1.8 nm.

5. The method according to claim 1, wherein said Electronic Property Response is Resistive Response, Resistive Response derived from Circuit, or Capacitive Response derived from Circuit.

6. The method according to claim 1, wherein said non-carbon material comprises titanium.

7. The method according to claim 1, wherein said non-carbon material comprises manganese.

8. The method according to claim 1, wherein said non-carbon material comprises iron.

9. The method according to claim 1, wherein said non-carbon material comprises cobalt.

10. The method according to claim 1, wherein said carbon nanotube is further coated with a second non-carbon material comprising titanium, manganese, iron, platinum, palladium, or cobalt.

11. The method according to claim 2, wherein the sensor provides at least one order of magnitude enhancement in sensitivity compared to a sensor comprising an unfilled carbon nanotube.

12. The method according to claim 5, wherein said Electronic Property Response is Resistive Response derived from Circuit.

13. The method according to claim 1, which detects and determines the concentration of ethanol vapor at a minimum detection limit of 0.23-91 parts per billion.

14. A method for detecting ethanol vapor in a gas mixture, comprising:
   flowing a gas mixture over a sensor comprising a carbon nanotube filled with one or more non-carbon materials comprising titanium, a manganese compound, iron, cobalt, palladium, platinum, or any combination thereof;
   detecting and determining the concentration of ethanol vapor in the gas mixture by measuring the Electronic Property Response of the sensor due to the ethanol vapor using an analysis unit connected to the sensor, wherein said carbon nanotube is a single wall carbon nanotube with an outer diameter varying in the range of 1.0 nm to 1.8 nm.

15. The method according to claim 14, wherein the sensor provides higher Electronic Property Response than a sensor comprising an unfilled carbon nanotube provides.

16. The method according to claim 14, wherein said Electronic Property Response is Resistive Response, Resistive Response derived from Circuit, or Capacitive Response derived from Circuit.

17. The method according to claim 14, wherein said non-carbon material comprises titanium.

18. The method according to claim 14, wherein said non-carbon material comprises manganese.

19. The method according to claim 14, wherein said non-carbon material comprises iron.

20. The method according to claim 14, wherein said non-carbon material comprises cobalt.

21. The method according to claim 14, wherein said carbon nanotube is further coated with a second non-carbon material comprising titanium, manganese, iron, platinum, palladium, or cobalt.

22. The method according to claim 15, wherein the sensor provides at least one order of magnitude enhancement in sensitivity compared to a sensor comprising an unfilled carbon nanotube.

23. The method according to claim 16, wherein said Electronic Property Response is Resistive Response derived from Circuit.

24. The method according to claim 14, which detects and determines the concentration of ethanol vapor at a minimum detection limit of 0.23-91 parts per billion.

* * * * *